(12) United States Patent
Gerlach et al.

(10) Patent No.: US 9,006,226 B2
(45) Date of Patent: Apr. 14, 2015

(54) DIHYDROPTERIDINONES I

(71) Applicants: Kai Gerlach, Mittelbiberach (DE); Christian Eickmeier, Mittelbiberach (DE); Claudia Heine, Biberach an der Riss (DE); Niklas Heine, Biberach an der Riss (DE); Alexander Weber, Biberach an der Riss (DE)

(72) Inventors: Kai Gerlach, Mittelbiberach (DE); Christian Eickmeier, Mittelbiberach (DE); Claudia Heine, Biberach an der Riss (DE); Niklas Heine, Biberach an der Riss (DE); Alexander Weber, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 15 days.

(21) Appl. No.: 13/767,591

(22) Filed: Feb. 14, 2013

(65) Prior Publication Data

US 2013/0225549 A1    Aug. 29, 2013

(30) Foreign Application Priority Data

Feb. 23, 2012  (EP) .................................. 12156686

(51) Int. Cl.

| | | |
|---|---|---|
| C07D 475/12 | (2006.01) | |
| C07D 475/00 | (2006.01) | |
| C07D 403/14 | (2006.01) | |
| C07D 405/14 | (2006.01) | |
| C07D 413/14 | (2006.01) | |
| C07D 498/22 | (2006.01) | |
| C07D 487/14 | (2006.01) | |
| C07D 471/14 | (2006.01) | |
| C07D 498/14 | (2006.01) | |

(52) U.S. Cl.
CPC ............ *C07D 475/00* (2013.01); *C07D 487/14* (2013.01); *C07D 471/14* (2013.01); *C07D 498/14* (2013.01); *C07D 475/12* (2013.01)

(58) Field of Classification Search
CPC .. C07D 243/20; C07D 243/00; C07D 401/00; C07D 401/04; C07D 487/14; C07D 471/14; C07D 475/12; C07D 475/00; C07D 403/14; C07D 405/14; C07D 413/14; C07D 498/22
USPC ......................................................... 544/251
See application file for complete search history.

(56) References Cited

U.S. PATENT DOCUMENTS

| | | |
|---|---|---|
| 6,806,272 B2 | 10/2004 | Bauer et al. |
| 7,371,753 B2 | 5/2008 | Stadtmueller et al. |
| 2004/0029885 A1 | 2/2004 | Bauer et al. |
| 2004/0176380 A1 | 9/2004 | Hoffmann et al. |
| 2006/0046990 A1 | 3/2006 | Stadtmueller et al. |

FOREIGN PATENT DOCUMENTS

| | | |
|---|---|---|
| WO | 03020722 A1 | 3/2003 |
| WO | 2004076454 A1 | 9/2004 |
| WO | 2006021548 A1 | 3/2006 |
| WO | 2006091737 A1 | 8/2006 |
| WO | 2010053438 A1 | 5/2010 |
| WO | 2010132015 A1 | 11/2010 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Sheridan (J. Chem. Inf. Comput. Sci., 2002, vol. 42, pp. 103-108).*
International Search Report, form PCT/ISA/210, and Written Opinion, form PCT/ISA/237, for corresponding application PCT/EP/2013/053403, date of mailing Jun. 4, 2013.

* cited by examiner

*Primary Examiner* — Jeffrey S Lundgren
*Assistant Examiner* — Chris Simmons
(74) *Attorney, Agent, or Firm* — Michael P. Morris; Alan R. Stempel

(57) ABSTRACT

The present invention relates to dihydropteridinones, their use as modulators of γ-secretase and to pharmaceutical compositions containing said compounds. In particular, the present invention relates to compounds which interfere with γ-secretase and/or its substrate and therefore modulate the formation of Aβ peptides.

4 Claims, No Drawings

DIHYDROPTERIDINONES I

FIELD OF THE INVENTION

The present invention relates to dihydropteridinones, their use as modulators of γ-secretase and to pharmaceutical compositions containing said compounds. In particular, the present invention relates to compounds which interfere with γ-secretase and/or its substrate and therefore modulate the formation of Aβ peptides. Accordingly these compounds can be used for the treatment of Aβ-related pathologies.

In addition, the invention relates to processes for preparing pharmaceutical compositions as well as compounds according to the invention.

BACKGROUND OF THE INVENTION

Alzheimer's disease (AD) is the most prevalent form of dementia. This neurodegenerative disorder is characterized by two major pathologies, β-amyloid deposits and neurofibrillary tangles. Clinically, AD is characterized by the loss of memory, cognition, reasoning, judgement as well as orientation. As the disease progresses, further abilities are lost until a global impairment of multiple cognitive functions occur. These cognitive losses take place gradually, but typically lead to severe impairment and eventual death in 4-12 years.

β-amyloid deposits are predominantly formed from aggregated Aβ peptide. The Aβ peptide is formed from amyloid precursor protein (APP) through two independent proteolytic events involving β-secretase followed by γ-secretase. Variability in the site of proteolysis via γ-secretase results in Aβ species of variable length, the most predominant forms of which are Aβ38, Aβ40 and Aβ42. The secreted Aβ then aggregates into oligomeric species, which further aggregate to ultimately form the Aβ deposits detected in the brains of AD patients. The aggregated oligomeric species are widely believed to be the key neurotoxic agent responsible for the neurodegeneration detected in the brains of AD patients. Of the various Aβ species generated by γ-secretase, Aβ42 has been demonstrated to be the most aggregation prone as well as the most neurotoxic Aβ species. Furthermore, human genetics strongly supports a key role of Aβ42 as a key mediator of AD pathogenesis. More than 150 different mutations causing familial AD are known which result from either an increase in the ratio of Aβ42/Aβ40 peptides produced or increase the intrinsic aggregation propensity of Aβ. Based on this knowledge, therapeutic approaches aimed at lowering levels of Aβ42 are considered promising.

β-amyloid deposits and vascular amyloid angiopathy have also been characterized in the brains of patients with Trisomy 21 (Down's Syndrome), Hereditary Cerebral Hemorrhage with Amyloidosis of the Dutch-type (HCHWA-D), and other neurodegenerative disorders.

γ-Secretase inhibitors completely inhibit the cleavage of APP as well as all other substrates of γ-secretase. This inhibition leads to a simultaneous inhibition of the production of all Aβ species. As opposed to γ-secretase inhibitors, γ-secretase modulators preferentially block the production of the neurotoxic Aβ42 species while not inhibiting APP cleavage and thereby the generation of all Aβ species. Furthermore, γ-Secretase modulators do not inhibit the cleavage of other γ-secretase substrates, thereby diminishing the possibility of side effects.

WO 2010/132015 discloses compounds of the following core structures interfering with γ-secretase and/or its substrate

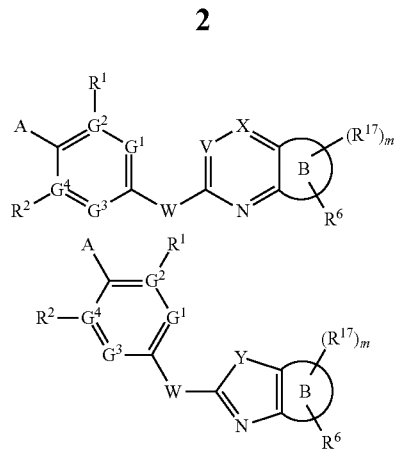

and their use as medicaments in the treatment of various diseases inter alia Alzheimer's disease.

WO 2011/014535 discloses compounds of the following core structure

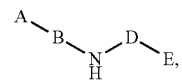

which modulate β-amyloid peptide production and their use in the treatment of Alzheimer's disease.

AIM OF THE INVENTION

It has now been found that compounds of the present invention according to general formula I are effective modulators of γ-secretase.

Accordingly, one aspect of the present invention relates to compounds according to formula I and salts thereof as modulators of γ-secretase.

A further aspect of the invention relates to the physiologically acceptable salts of the compounds of general formula I according to this invention with inorganic or organic acids.

In a further aspect this invention relates to pharmaceutical compositions, containing at least one compound according to formula I or a physiologically acceptable salt thereof, optionally together with one or more inert carriers and/or diluents.

A further aspect of the present invention relates to compounds according to formula I or a physiologically acceptable salt thereof or pharmaceutical compositions comprising compounds according to formula I or physiologically acceptable salts thereof for the use in the prevention and/or treatment of Aβ-related pathologies.

In a further aspect this invention relates to pharmaceutical compositions, containing at least one compound according to formula I or a physiologically acceptable salt thereof, optionally together with one or more inert carriers and/or diluents.

A further aspect of the present invention relates to compounds according to formula I or a physiologically acceptable salt thereof or pharmaceutical compositions comprising compounds according to formula I or physiologically acceptable salts thereof for the use in the prevention and/or treatment of diseases or conditions which can be influenced by modulating Aβ peptides, such as Aβ-related pathologies like Down's syndrome, Abeta-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, dementia associated with Parkinson's disease, progressive supranuclear palsy or cortical basal degeneration, the dry form of age-related macular degeneration and glaucoma.

Other aims of the present invention will become apparent to the skilled man directly from the foregoing and following remarks.

DETAILED DESCRIPTION

In a first aspect the present invention relates to compounds of general formula I

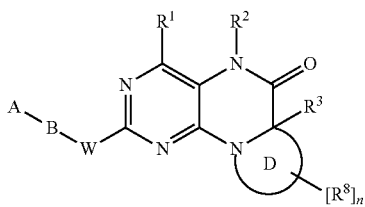

I wherein
A is selected from the group $A^a$ consisting of
  a heteroaryl group with 5 or 6 ring atoms containing one to three heteroatoms independently selected from N, O, S, wherein above mentioned heteroaryl groups may optionally be substituted with 1 or 2 substituents independently selected from the group consisting of halogen, cyano, $C_{1-6}$-alkyl- which is optionally fluorinated with 1 to 13 fluorine atoms, $HO-C_{1-3}$-alkyl-, $C_{3-6}$-cycloalkyl-, $C_{1-4}$-alkyl-O—$C_{1-3}$-alkyl-, $C_{1-4}$-alkyl-O— which is optionally fluorinated with 1 to 9 fluorine atoms and $(C_{1-4}$-alkyl$)_3$Si—;
B is selected from the group $B^a$ consisting of

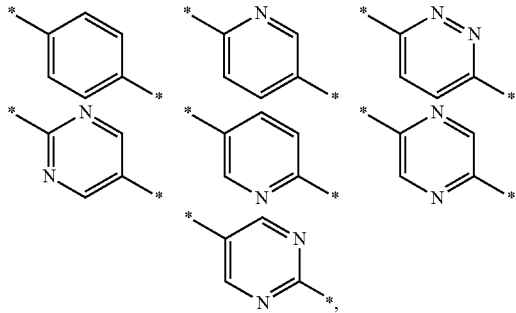

wherein above mentioned phenyl-, pyridinyl-, pyrimidinyl-, pyridazinyl and pyrazinyl groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms;
D is selected from the group $D^a$ consisting of
  a mono- or bicyclic heterocyclic group consisting, including the atoms to which ring D is attached to the core molecule, of 4 to 11 ring atoms, or a bicyclic heteroaryl group consisting, including the atoms to which ring D is attached to the core molecule, of 8 to 11 ring atoms, wherein the ring which is directly attached to the core molecule is not aromatic, and wherein above mentioned heterocyclic and heteroaryl groups, if they comprise a nitrogen atom, may optionally be substituted with $R^6$ at said nitrogen atom;
W is selected from the group $W^a$ consisting of
  —$(R^7)$N— and —O—;
$R^1$ is selected from the group $R^{1a}$ consisting of
  H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—$C_{1-3}$-alkyl-, $R^9O$—, $R^9S(O)_m$— with m=0, 1, 2,
    wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5S$—, $(C_{1-4}$-alkyl$)_3$Si—, nitro, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-, and
    wherein above mentioned $C_{1-4}$-alkyl-O—, $C_{3-6}$-cycloalkyl-O—, heterocyclyl-O—, $(C_{1-4}$-alkyl$)_2N$—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-groups may optionally be substituted with 1 to 13 fluorine atoms;
$R^2$ is selected from the group $R^{2a}$ consisting of
  H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—, $R^4R^5N$—$C_{1-3}$-alkyl-, and $R^9O$—,
    wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, $R^4R^5N$—$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5S$—, $(C_{1-4}$-alkyl$)_3$Si—, nitro, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl-. $C_{3-6}$-cycloalkyl- and $C_{1-6}$-alkyl-, and
    wherein above mentioned $C_{1-4}$-alkyl-O—, $C_{3-6}$-cycloalkyl-O—, heterocyclyl-O—, $(C_{1-4}$-alkyl$)_2N$—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl-, $C_{3-6}$-cycloalkyl- and $C_{1-6}$-alkyl-groups may optionally be substituted with 1 to 13 fluorine atoms;

$R^3$ is selected from the group $R^{3a}$ consisting of
  H, $C_{1-6}$-alkyl-, cyclopropyl- and cyclobutyl-,
    wherein the above mentioned $C_{1-6}$-alkyl-, cyclopropyl- and cyclobutyl-groups may optionally be substituted with 1 to 3 substituents independently selected from the group consisting of halogen, cyano, HO—, $C_{1-3}$-alkyl- and $C_{1-3}$-alkyl-O—, or
  $R^{3a}$ is part of the bicyclic heterocycle as defined for D.

$R^4$, $R^5$ are selected independently of each other from the group $R^{4a}/R^{5a}$ consisting of
  H, $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl-, heterocyclyl-O—$C_{2-4}$-alkyl-, aryl, aryl-$C_{1-3}$-alkyl-, aryl-O—$C_{2-3}$-alkyl-, heteroaryl, heteroaryl-$C_{1-3}$-alkyl- and heteroaryl-O—$C_{2-3}$-alkyl-,
    wherein above mentioned $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl- and heterocyclyl-O—$C_{2-4}$-alkyl-groups may optionally be substituted with 1 to 3 substituents independently selected from the group consisting of halogen, cyano, HO—, oxo, $C_{1-4}$-alkyl-O— which is optionally fluorinated with 1 to 9 fluorine atoms, $C_{1-4}$-alkyl-O—C(O)—, HO—$C_{1-4}$-alkyl-, $C_{1-4}$-alkyl-O—$C_{1-4}$-alkyl-, heterocyclyl, $(C_{1-4}$-alkyl$)_2$N—, $(C_{1-3}$-alkyl$)_2$N—C(O)—, and $C_{1-6}$-alkyl- which is optionally fluorinated with 1 to 13 fluorine atoms, and
    wherein above mentioned aryl-, aryl-$C_{1-3}$-alkyl-, aryl-O—$C_{2-3}$-alkyl-, heteroaryl-, heteroaryl-$C_{1-3}$-alkyl- and heteroaryl-O—$C_{2-3}$-alkyl-groups may optionally be substituted with 1 to 3 substituents independently selected from the group consisting of HO—, $C_{1-4}$-alkyl-O—, $F_3$CO—, $F_2$HCO—, $FH_2$CO—, heterocyclyl-O—, cyano, halogen, $F_5$S—, $(C_{1-4}$-alkyl$)_3$Si—, nitro, $(R^6)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms, or
  $R^{4a}$ and $R^{5a}$ form together with the nitrogen atom to which they are attached a 4-12-membered mono-, bicyclic or bridged ring system optionally containing one or two double bonds and/or one aromatic ring and optionally containing one or two additional heteroatoms selected from the group consisting of —O—, —S—, —S(O)—, —S(O)$_2$—, —N(R$^6$)—,
    wherein 2 geminal hydrogen atoms of the 4-12-membered mono- or bicyclic ring system may be replaced by a —(CH$_2$)$_{1-5}$— group and
      wherein one —(CH$_2$)— group of the —(CH$_2$)$_{1-5}$— group may be replaced by —O— or —N(R$^6$)— and
    wherein above mentioned 4-12-membered mono-, bicyclic or bridged ring system may optionally be substituted with 1 or 2 substituents independently selected from the group consisting of halogen, cyano, aryl, heteroaryl, aryl-$C_{1-3}$-alkyl-, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, $C_{1-4}$-alkyl-O—C(O)—, HO—$C_{1-4}$-alkyl-, $C_{1-4}$-alkyl-O—$C_{1-4}$-alkyl-, $C_{3-6}$-cycloalkyl-O—$C_{1-4}$-alkyl-, heterocyclyl-O—, heterocyclyl-O—$C_{1-4}$-alkyl-, aryl-O—, heteroaryl-O— and $(R^6)_2$N—,
      wherein the directly above mentioned aryl, aryl-$C_{1-3}$-alkyl-, aryl-O—, heteroaryl-O—, and heteroaryl groups may optionally be substituted with 1 to 3 substituents independently selected from the group consisting of HO—, $C_{1-4}$-alkyl-O—, $F_3$CO—, $F_2$HCO—, $FH_2$CO—, heterocyclyl-O—, cyano, halogen, $F_5$S—, $(C_{1-4}$-alkyl$)_3$Si—, nitro, amino, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms;

$R^6$ is selected independently of each other from the group $R^{6a}$ consisting of
  H, $C_{1-6}$-alkyl-, $C_{3-6}$-cycloalkyl, heterocyclyl, heteroaryl, HC(O)—, $C_{1-6}$-alkyl-C(O)—, $C_{3-6}$-cycloalkyl-C(O)—, aryl-C(O)—, heteroaryl-C(O)—, $C_{1-4}$-alkyl-O—C(O)— and $(C_{1-4}$-alkyl$)_2$N—C(O)—,
    wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms and
    wherein the above mentioned aryl-C(O)—, heteroaryl-C(O)— and heteroaryl groups may optionally be substituted with 1 to 3 substituents independently selected from the group consisting of HO—, $C_{1-4}$-alkyl-O—, $F_3$CO—, $F_2$HCO—, $FH_2$CO—, heterocyclyl-O—, cyano, halogen, $F_5$S—, $(C_{1-4}$-alkyl$)_3$Si—, nitro, amino, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms;

$R^7$ is selected independently of each other from the group $R^{7a}$ consisting of
  H, $C_{1-6}$-alkyl-, $C_{1-6}$-alkyl-C(O)— and $C_{1-6}$-alkyl-O—C(O)—;

$R^8$ is selected from the group $R^{8a}$ consisting of
  H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—, $R^4R^5N$—$C_{1-3}$-alkyl-, and $R^9O$—,
    wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5$S—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl-, and
    wherein above mentioned $C_{1-4}$-alkyl-O—, $C_{3-6}$-cycloalkyl-O—, heterocyclyl-O—, $(C_{1-4}$-alkyl$)_2$N—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl-groups may optionally be substituted with 1 to 13 fluorine atoms;

$R^9$ is selected from the group $R^{9a}$ consisting of
  H, $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl-, heterocyclyl-O—$C_{2-4}$-alkyl-, aryl, aryl-$C_{1-3}$-alkyl-, aryl-O—$C_{2-3}$-alkyl-, heteroaryl, heteroaryl-$C_{1-3}$-alkyl- and heteroaryl-O—$C_{2-3}$-alkyl-,
    wherein above mentioned $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl- and heterocyclyl-O—$C_{2-4}$-alkyl-groups may optionally be substituted with 1 to 3 substituents independently selected from the group consisting of halogen, cyano, HO—, oxo, $C_{1-4}$-alkyl-O— which is optionally fluorinated with 1 to 9 fluorine atoms, $C_{1-4}$-alkyl-O—C(O)—, HO—$C_{1-4}$-alkyl-, $C_{1-4}$-alkyl-O—$C_{1-4}$-alkyl-, heterocyclyl, $(C_{1-4}$-alkyl$)_2$N—, $(C_{1-3}$-alkyl$)_2$N—C(O)—, and $C_{1-6}$-alkyl- which is optionally fluorinated with 1 to 13 fluorine atoms, wherein above mentioned aryl-, aryl-$C_{1-3}$-alkyl-, aryl-O—$C_{2-3}$-alkyl-, heteroaryl-, heteroaryl-$C_{1-3}$-alkyl- and heteroaryl-O—$C_{2-3}$-alkyl-groups may optionally be substituted with 1 to 3 substituents independently selected from the group consisting of HO—, $C_{1-4}$-alkyl-O—, $F_3$CO—, $F_2$HCO—, $FH_2$CO—, heterocyclyl-O—, cyano, halogen, $F_5$S—, $(C_{1-4}$-alkyl$)_3$Si—, nitro, $(R^6)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms, n is 0, 1, 2, 3, 4 or 5;

the tautomers thereof, the stereoisomers thereof, the mixtures thereof and the salts thereof.

Unless otherwise stated, the groups, residues, and substituents, particularly $R^1$, $R^2$, $R^3$, $R^4$, $R^5$, $R^6$, $R^7$, $R^8$, $R^9$, A, B, D and W are defined as above and hereinafter. If residues, substituents, or groups occur several times in a compound they may have the same or different meanings. Some preferred meanings of groups and substituents of the compounds according to the invention will be given hereinafter.

In a further embodiment of the present invention

A is selected from the group $A^b$ consisting of

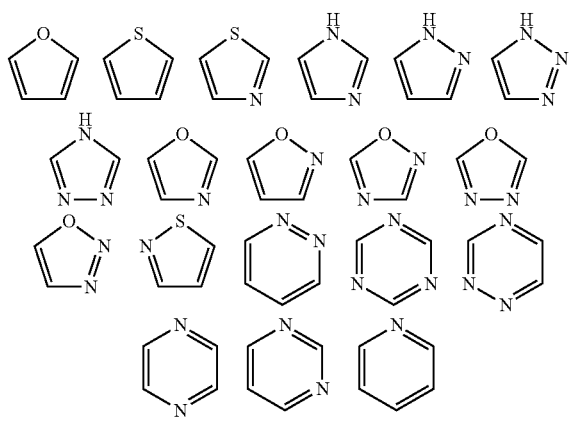

wherein above mentioned groups may optionally be substituted with 1 or 2 substituents independently selected from the group consisting of halogen, cyano, and $C_{1-6}$-alkyl- which is optionally fluorinated with 1 to 13 fluorine atoms.

In a further embodiment of the present invention

A is selected from the group $A^c$ consisting of

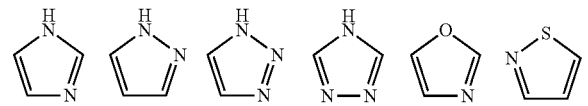

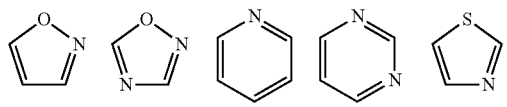

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention

A is selected from the group $A^d$ consisting of

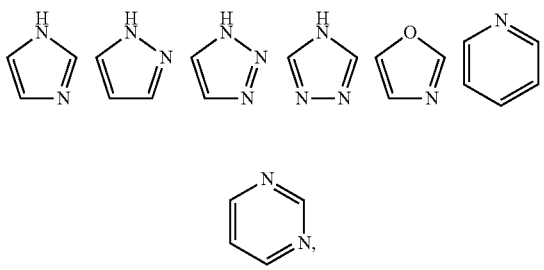

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention

A is selected from the group $A^e$ consisting of

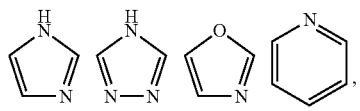

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention

B is selected from the group $B^b$ consisting of

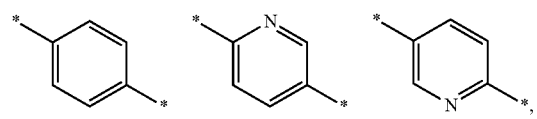

wherein above mentioned phenyl- and pyridinyl- groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms.

In a further embodiment of the present invention
B is selected from the group $B^c$ consisting of

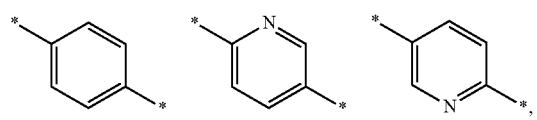

wherein above mentioned phenyl- and pyridinyl- groups may optionally be substituted with 1 or 2 substituents independently selected from the group consisting of halogen, cyano, $C_{1-3}$-alkyl-which is optionally fluorinated with 1 to 7 fluorine atoms, and $C_{1-3}$-alkyl-O— which is optionally fluorinated with 1 to 7 fluorine atoms.

In a further embodiment of the present invention
D is selected from the group $D^b$ consisting of
a mono- or bicyclic heterocycle consisting, including the atoms to which ring D is attached to the core molecule, of 4 to 11 ring atoms, and wherein above mentioned heterocyclic groups, if they comprise a nitrogen atom, may optionally be substituted with $R^6$ at said nitrogen atom.

In a further embodiment of the present invention
D is selected from the group $D^c$ consisting of
a monocyclic heterocycle consisting, including the atoms to which ring D is attached to the core molecule, of 4 to 7 ring atoms, and
wherein above mentioned heterocyclic groups, if they comprise a nitrogen atom, may optionally be substituted with $R^6$ at said nitrogen atom.

In a further embodiment of the present invention
D is selected from the group $D^d$ consisting of

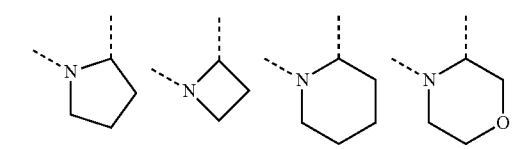
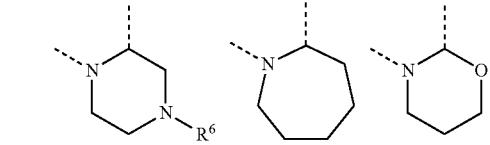
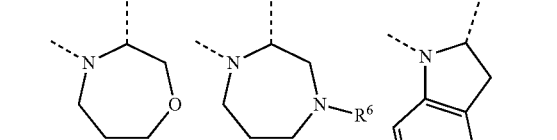
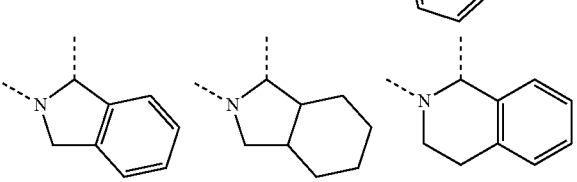

-continued

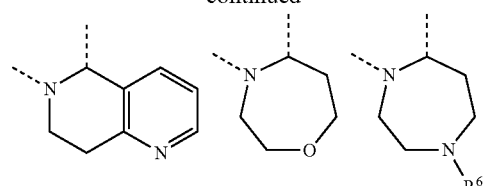
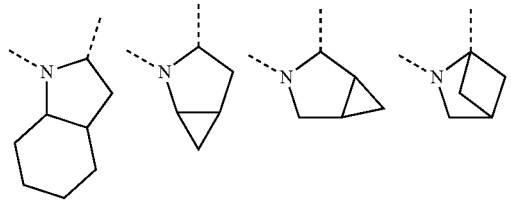
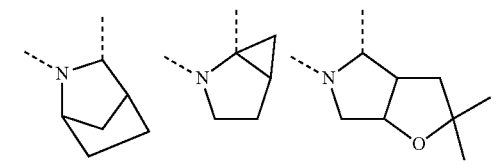
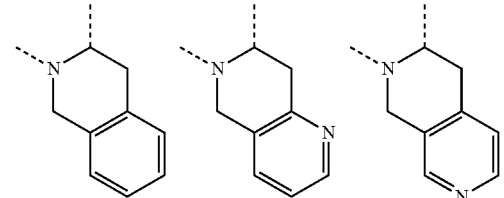
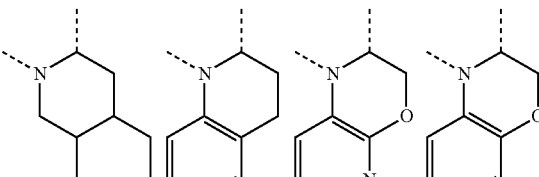
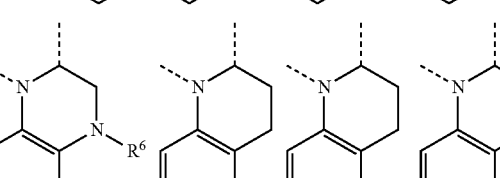
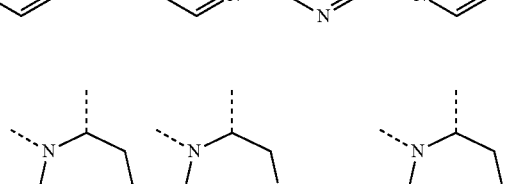
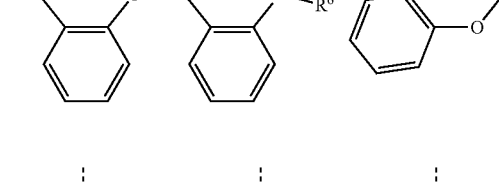
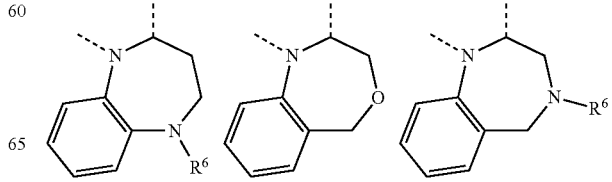
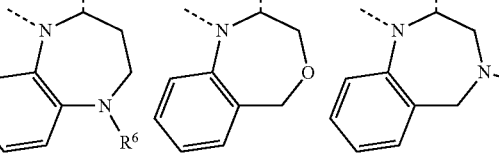

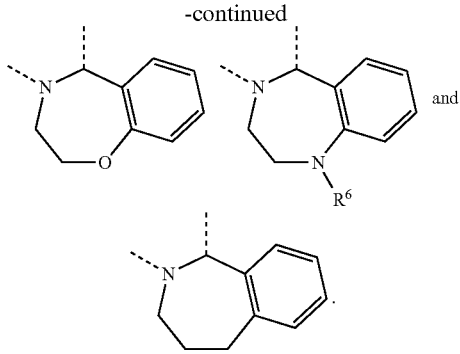

In a further embodiment of the present invention
D is selected from the group $D^e$ consisting of

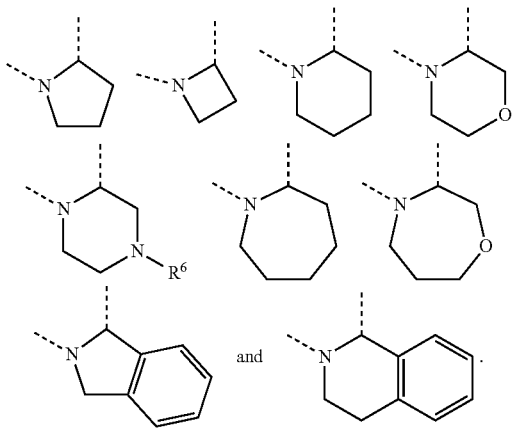

In a further embodiment of the present invention
D is selected from the group $D^e$ consisting of

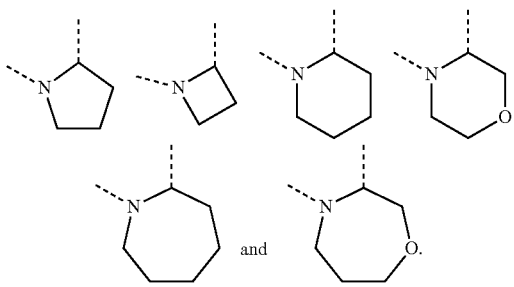

In a further embodiment of the present invention
W is selected from the group $W^b$ consisting of
—($R^7$)N—.

In a further embodiment of the present invention
$R^1$ is selected from the group $R^{1b}$ consisting of
 H, $C_{1-8}$-alkyl-, carbocyclyl, carbocyclyl-$C_{1-3}$-alkyl-, C-linked heterocyclyl, heterocyclyl-$C_{1-3}$-alkyl-, aryl-$C_{1-3}$-alkyl-, heteroaryl, heteroaryl-$C_{1-3}$-alkyl-, $R^4R^5$N—$C_{1-3}$-alkyl-, $R^9$O—, and $R^9$S(O)$_m$— with m=0, 1, 2
  wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, aryl-$C_{1-3}$-alkyl-, heteroaryl, heteroaryl-$C_{1-3}$-alkyl- and $R^4R^5$N—$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2$N—, ($C_{1-4}$-alkyl)$_2$N—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl-, and
  wherein above mentioned $C_{1-4}$-alkyl-O—, $C_{3-6}$-cycloalkyl-O—, heterocyclyl-O—, ($C_{1-4}$-alkyl)$_2$N—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl-groups may optionally be substituted with 1 to 13 fluorine atoms.

In a further embodiment of the present invention
$R^1$ is selected from the group $R^{1c}$ consisting of
 H, $C_{1-8}$-alkyl-, carbocyclyl, carbocyclyl-$C_{1-3}$-alkyl-, C-linked heterocyclyl, heterocyclyl-$C_{1-3}$-alkyl-, aryl-$C_{1-3}$-alkyl-, $R^9$O— and $R^9$S—,
  wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl- and aryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $C_{1-4}$-alkyl-O—$C_{1-4}$-alkyl- and $C_{1-6}$-alkyl-, and
  wherein above mentioned $C_{1-4}$-alkyl-O—, $C_{3-6}$-cycloalkyl-O—, heterocyclyl-O—, $C_{1-4}$-alkyl-O—$C_{1-4}$-alkyl- and $C_{1-6}$-alkyl-groups may optionally be substituted with 1 to 13 fluorine atoms.

In a further embodiment of the present invention
$R^1$ is selected from the group $R^{1d}$ consisting of
 H, $C_{1-8}$-alkyl-, $C_{3-6}$-cycloalkyl-, $C_{3-6}$-cycloalkyl-$C_{1-3}$-alkyl-, C-linked heterocyclyl, heterocyclyl-$C_{1-3}$-alkyl-, phenyl-$C_{1-3}$-alkyl-, and $R^9$S—,
  wherein above mentioned $C_{1-8}$-alkyl-, $C_{3-6}$-cycloalkyl-, $C_{3-6}$-cycloalkyl-$C_{1-3}$-alkyl-, C-linked heterocyclyl, heterocyclyl-$C_{1-3}$-alkyl-, phenyl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $C_{1-4}$-alkyl-O—$C_{1-4}$-alkyl- and $C_{1-6}$-alkyl-, and
  wherein above mentioned $C_{1-4}$-alkyl-O—, $C_{3-6}$-cycloalkyl-O—, heterocyclyl-O—, $C_{1-4}$-alkyl-O—$C_{1-4}$-alkyl- and $C_{1-6}$-alkyl-groups may optionally be substituted with 1 to 13 fluorine atoms.

In a further embodiment of the present invention
$R^1$ is selected from the group $R^{1e}$ consisting of
 H, $C_{1-6}$-alkyl-, $C_{3-6}$-cycloalkyl-, phenyl-$C_{1-3}$-alkyl- and $C_{1-3}$-alkyl-S—,
  wherein above mentioned $C_{1-6}$-alkyl-, $C_{3-6}$-cycloalkyl- and $C_{1-3}$-alkyl-S— groups may optionally be substituted with 1 to 13 fluorine atoms, wherein above mentioned phenyl-$C_{1-3}$-alkyl-group may optionally be substituted with 1 to 3 substituents independently selected from the group consisting of $C_{1-3}$-alkyl-O—, cyano, halogen, and $C_{1-3}$-alkyl- and
  wherein above mentioned $C_{1-3}$-alkyl-O— and $C_{1-3}$-alkyl-groups may optionally be substituted with 1 to 7 fluorine atoms.

In a further embodiment of the present invention
$R^1$ is selected from the group $R^{1f}$ consisting of
  H, $C_{1-4}$-alkyl-, $C_{3-6}$-cycloalkyl- and benzyl-,
    wherein above mentioned $C_{1-4}$-alkyl- and $C_{3-6}$-cycloalkyl-groups may optionally be substituted with 1 to 11 fluorine atoms,
    wherein above mentioned benzyl- group may optionally be substituted with 1 to 3 substituents independently selected from the group consisting of $C_{1-3}$-alkyl-O—, cyano, halogen, and $C_{1-3}$-alkyl-, and
      wherein above mentioned $C_{1-3}$-alkyl-O— and $C_{1-3}$-alkyl-groups may optionally be substituted with 1 to 7 fluorine atoms.

In a further embodiment of the present invention
$R^2$ is selected from the group $R^{2b}$ consisting of
  H, $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl- and $R^4R^5N$—$C_{2-3}$-alkyl-,
    wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, $R^4R^5N$—$C_{2-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, ($C_{1-4}$-alkyl)$_2$N—, ($H_2N$)—C(O)—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl-, and
      wherein above mentioned $C_{1-4}$-alkyl-O—, $C_{3-6}$-cycloalkyl-O—, heterocyclyl-O—, ($C_{1-4}$-alkyl)$_2$N—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl-groups may optionally be substituted with 1 to 13 fluorine atoms.

In a further embodiment of the present invention
$R^2$ is selected from the group $R^{2c}$ consisting of
  H, $C_{1-8}$-alkyl-, $C_3$-$C_6$-cycloalkyl-, $C_3$-$C_6$-cycloalkyl-$C_{1-3}$-alkyl-, phenyl, phenyl-$C_{1-3}$-alkyl-, C-linked heterocyclyl and heterocyclyl-$C_{1-3}$-alkyl-,
    wherein above mentioned $C_{1-8}$-alkyl-, $C_3$-$C_6$-cycloalkyl-, $C_3$-$C_6$-cycloalkyl-$C_{1-3}$-alkyl-, phenyl, phenyl-$C_{1-3}$-alkyl-, C-linked heterocyclyl and heterocyclyl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $C_{1-4}$-alkyl-O—$C_{1-4}$-alkyl- and $C_{1-6}$-alkyl-, and
      wherein above mentioned $C_{1-4}$-alkyl-O—, $C_{3-6}$-cycloalkyl-O—, heterocyclyl-O—, $C_{1-4}$-alkyl-O—$C_{1-4}$-alkyl- and $C_{1-6}$-alkyl-groups may optionally be substituted with 1 to 13 fluorine atoms.

In a further embodiment of the present invention
$R^2$ is selected from the group $R^{2d}$ consisting of
  H, phenyl, phenyl-$C_{1-3}$-alkyl-, $C_3$-$C_6$-cycloalkyl-, oxetanyl-, tetrahydrofuryl, tetrahydropyranyl- and $C_{1-5}$-alkyl-,
    wherein above mentioned $C_{1-5}$-alkyl-, $C_3$-$C_6$-cycloalkyl-, oxetanyl-, tetrahydrofuryl, and tetrahydropyranyl- groups may optionally be substituted with 1 to 3 substituents independently selected from the group consisting of HO— and $C_{1-3}$-alkyl-O—,
    wherein above mentioned phenyl and phenyl-$C_{1-3}$-alkyl-groups may optionally be substituted with 1 to 3 substituents independently selected from the group consisting of $C_{1-4}$-alkyl-O—, cyano, halogen, and $C_{1-6}$-alkyl-, and
      wherein above mentioned $C_{1-5}$-alkyl- and $C_{1-3}$-alkyl-O—, $C_{1-4}$-alkyl-O—, and $C_{1-6}$-alkyl-groups may optionally be substituted with 1 to 11 fluorine atoms.

$R^2$ is selected from the group $R^{2e}$ consisting of
  H, $C_{1-3}$-alkyl-O—$C_{1-3}$-alkyl- and $C_{1-3}$-alkyl-.

In a further embodiment of the present invention
$R^3$ is selected from the group $R^{3b}$ consisting of
  H, and $C_{1-3}$-alkyl-,
    wherein the above mentioned $C_{1-3}$-alkyl-group may optionally be substituted with 1 to 3 substituents independently selected from the group consisting of halogen and cyano.

In a further embodiment of the present invention
$R^3$ is selected from the group $R^{3c}$ consisting of
  H and $H_3C$—.

In a further embodiment of the present invention
$R^4$, $R^5$ are selected independently of each other from the group $R^{4b}/R^{5b}$ consisting of
  H, $C_{1-6}$-alkyl-, $C_{3-7}$-cycloalkyl, $C_{3-7}$-cycloalkyl-heterocyclyl, heterocyclyl-$C_{1-6}$-alkyl-, aryl, aryl-$C_{1-3}$-alkyl-, aryl-O—$C_{2-3}$-alkyl-, heteroaryl and heteroaryl-$C_{1-3}$-alkyl-,
    wherein above mentioned $C_{1-6}$-alkyl-, $C_{3-7}$-cycloalkyl-, $C_{3-7}$-cycloalkyl-$C_{1-3}$-alkyl-, $C_{3-7}$-cycloalkyl-O—$C_{2-4}$-alkyl-, heterocyclyl or heterocyclyl-$C_{1-6}$-alkyl-groups may optionally be substituted with 1 to 3 substituents independently selected from the group consisting of fluoro, HO—, oxo, $C_{1-4}$-alkyl-O— which is optionally fluorinated with 1 to 9 fluorine atoms, HO—$C_{1-4}$-alkyl-, $C_{1-4}$-alkyl-O—$C_{1-4}$-alkyl-, heterocyclyl, ($C_{1-3}$-alkyl)$_2$N—C(O)—, and $C_{1-6}$-alkyl- which is optionally fluorinated with 1 to 13 fluorine atoms,
    wherein above mentioned aryl-, aryl-$C_{1-3}$-alkyl-, aryl-O—$C_{2-3}$-alkyl-, heteroaryl- and heteroaryl-$C_{1-3}$-alkyl-groups may optionally be substituted with 1 to 3 substituents independently selected from the group consisting of $C_{1-4}$-alkyl-O—, $F_3CO$—, $F_2HCO$—, $FH_2CO$—, cyano, halogen, ($C_{1-4}$-alkyl)$_2$N—C(O)—, and $C_{1-6}$-alkyl- which is optionally fluorinated with 1 to 13 fluorine atoms, or
  $R^{4b}$ and $R^{5b}$ form together with the nitrogen atom to which they are attached a 4-12-membered mono-, bicyclic or bridged ring system optionally containing one double bond and/or one aromatic ring and optionally containing one additional heteroatom selected from the group consisting of —O—, —N($R^6$)—,
    wherein 2 geminal hydrogen atoms of the 4-12-membered mono- or bicyclic ring may be replaced by a —(CH$_2$)$_{1-5}$— group and
    wherein one —(CH$_2$)— group of the —(CH$_2$)$_{1-5}$— group may be replaced by —O— or —N($R^6$)— and
    wherein above mentioned 4-12-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, heterocyclyl-O— and ($R^6$)$_2$N—,
      wherein the directly above mentioned aryl and heteroaryl groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}$-alkyl$)_2N$—C(O)— and $C_{1-6}$-alkyl- which is optionally fluorinated with 1 to 13 fluorine atoms.

In a further embodiment of the present invention $R^4$, $R^5$ are selected independently of each other from the group $R^{4c}/R^{5c}$ consisting of H, $C_{1-6}$-alkyl-, $C_{3-7}$-cycloalkyl, $C_{3-7}$-cycloalkyl-$C_{1-3}$-alkyl-, $C_{3-7}$-cycloalkyl-azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-, phenyl, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, triazinyl-$C_{1-3}$-alkyl-, wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl, 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl- or oxazepanyl-$C_{1-3}$-alkyl-groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl-, morpholinyl, oxetanyl, tetrahydrofuryl, tetrahydropyranyl, $(C_{1-3}$-alkyl$)_2N$—C(O)—, and $C_{1-6}$-alkyl- which is optionally fluorinated with 1 to 13 fluorine atoms, wherein above mentioned phenyl-, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, Pyrimidinyl-$C_{1-3}$-alkyl-, and triazinyl-$C_{1-3}$-alkyl-groups may optionally be substituted with 1 to 3 substituents independently selected from the group consisting of $C_{1-3}$-alkyl-, $F_3C$—, $C_{1-4}$-alkyl-O—, $F_3CO$—, $F_2HCO$—, $FH_2CO$—, cyano and halogen, or $R^{4c}$ and $R^{5c}$ form together with the nitrogen atom to which they are attached a 4-11-membered mono-, bicyclic or bridged ring system optionally containing one aromatic ring and optionally one additional heteroatom selected from the group consisting of —O—, —N($R^6$)—, wherein 2 geminal hydrogen atoms of the 4-11-membered saturated mono- or bicyclic ring may be replaced by a —(CH$_2$)$_{1-5}$— group and wherein one —(CH$_2$)— group of the —(CH$_2$)$_{1-5}$— group may be replaced by —O— or —N($R^6$)— and wherein above mentioned 4-11-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, heterocyclyl-O—, $(R^6)_2N$—;

wherein the directly above mentioned aryl and heteroaryl groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}$-alkyl$)_2N$—C(O)— and $C_{1-6}$-alkyl- which is optionally fluorinated with 1 to 13 fluorine atoms.

In a further embodiment of the present invention $R^4$, $R^5$ are selected independently of each other from the group $R^{4d}/R^{5d}$ consisting of H, $C_{1-6}$-alkyl-, $C_{3-7}$-cycloalkyl, $C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-, phenyl, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, triazinyl-$C_{1-3}$-alkyl-, wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl, 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl- or tetrahydropyranyl-$C_{1-3}$-alkyl-groups may optionally be substituted with 1 to 3 substituents independently selected from the group consisting of fluoro, HO—, oxo, HO—$C_{1-4}$-alkyl-, $C_{1-4}$-alkyl-O—$C_{1-4}$-alkyl-, oxetanyl, tetrahydrofuryl, tetrahydropyranyl, and $C_{1-6}$-alkyl- which is optionally fluorinated with 1 to 13 fluorine atoms, wherein above mentioned phenyl-, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-pyrimidinyl-$C_{1-3}$-alkyl- and triazinyl-$C_{1-3}$-alkyl-groups may optionally be substituted with 1 to 3 substituents independently selected from the group consisting of $C_{1-3}$-alkyl-, $F_3C$—, $C_{1-4}$-alkyl-O—, $F_3CO$—, $F_2HCO$—, $FH_2CO$—, cyano and halogen, or $R^{4d}$ and $R^{5d}$ form together with the nitrogen atom to which they are attached a ring system selected from the group consisting of,

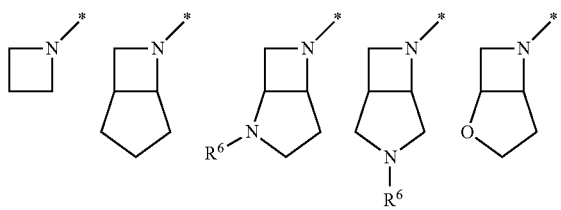

-continued
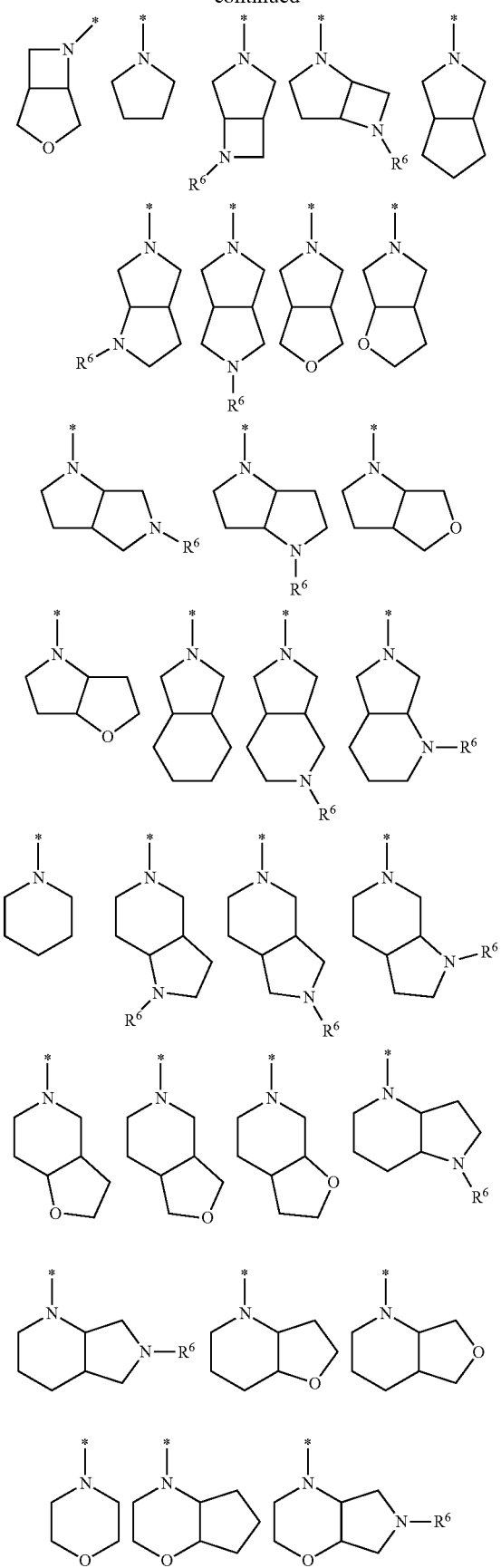
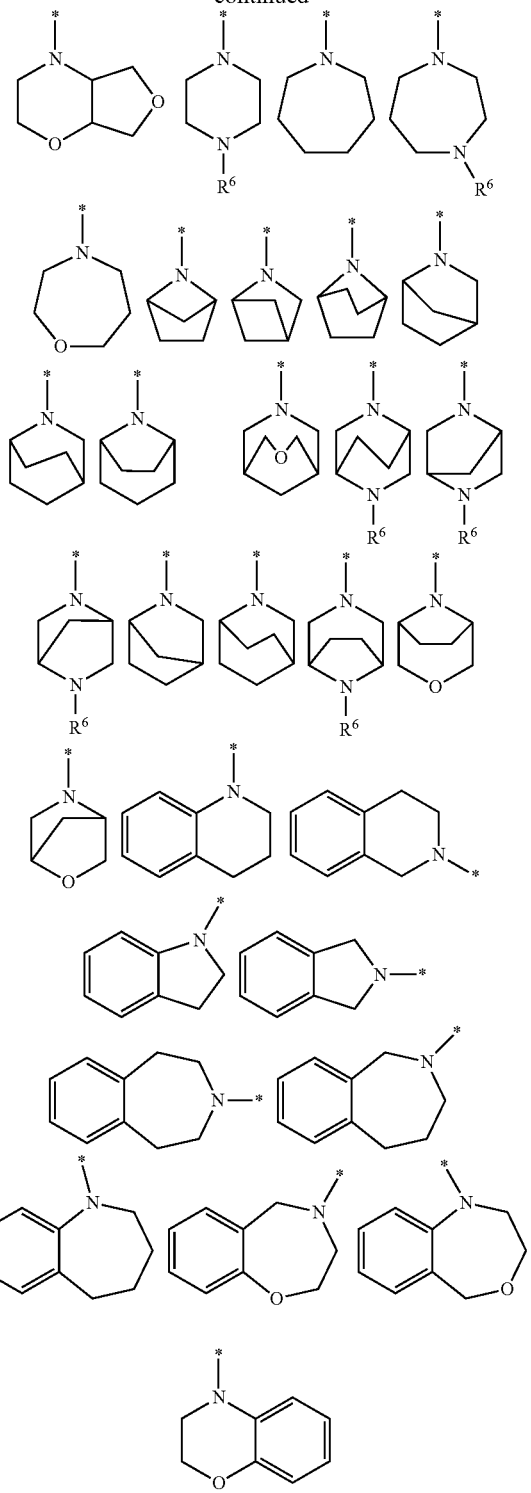
wherein 2 geminal hydrogen atoms of the above mentioned mono- or bicyclic ring may be replaced by a —(CH$_2$)$_{3-5}$— group and
wherein one —(CH$_2$)— group of the —(CH$_2$)$_{3-5}$— group may be replaced by —O— or —N(R$^6$)— and
wherein above mentioned mono- or bicyclic ring may optionally be substituted with 1 or 2 substituents independently selected from the group consisting of fluoro, phenyl, $C_{1-6}$-alkyl- which is optionally fluorinated with 1 to 13 fluorine atoms, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, oxetanyl-O—, tetrahydrofuryl-O—, tetrahydropyranyl-O— and $(R^6)_2N$— wherein the aforementioned phenyl groups may optionally be substituted with 1 to 3 substituents independently selected from the group consisting of $F_3C$—, $C_{1-4}$-alkyl-O—, $F_3CO$—, $F_2HCO$—, $FH_2CO$—, cyano, halogen, and $C_{1-3}$-alkyl-.

In a further embodiment of the present invention
$R^4$, $R^5$ are selected independently of each other from the group $R^{4e}/R^{5e}$ consisting of H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-,
wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl- and $C_{1-3}$-alkyl- which is optionally fluorinated with 1 to 7 fluorine atoms, or
$R^{4e}$ and $R^{5e}$ form together with the nitrogen atom to which they are attached a ring system selected from the group consisting of

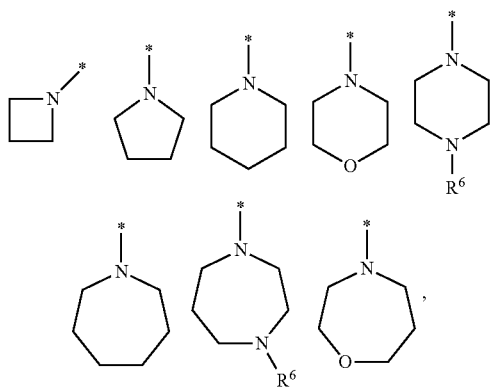

wherein above mentioned monocyclic rings may optionally be substituted with 1 or 2 substituents independently selected from the group consisting of fluoro, $C_{1-3}$-alkyl- which is optionally fluorinated with 1 to 7 fluorine atoms, HO—, oxo, $C_{1-6}$-alkyl-O—, $C_{3-6}$-cycloalkyl-O—, HO—$C_{1-4}$-alkyl- and $C_{1-4}$-alkyl-O—$C_{1-4}$-alkyl-.

In a further embodiment of the present invention
$R^4$, $R^5$ are selected independently of each other from the group $R^{4f}/R^{5f}$ consisting of H and $C_{1-5}$-alkyl- which is optionally fluorinated with 1 to 13 fluorine atoms.

In a further embodiment of the present invention
$R^6$ is selected independently of each other from the group $R^{6b}$ consisting of H, $C_{1-6}$-alkyl-, $C_{3-6}$-cycloalkyl, oxetanyl, tetrahydrofuryl, tetrahydropyranyl, pyridinyl, pyrimidinyl, pyridazinyl, pyrazinyl, triazinyl, thiazolyl, oxadiazolyl, oxazolyl, HC(O)—, $C_{1-6}$-alkyl-C(O)—, $C_{3-6}$-cycloalkyl-C(O)—, phenyl-O(O)—, $C_{1-4}$-alkyl-O—C(O)— and $(C_{1-4}$-alkyl$)_2N$—C(O)—,
wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms,
wherein the aforementioned phenyl-O(O)—, pyridinyl, pyrimidinyl, pyridazinyl, pyrazinyl, triazinyl, thiazolyl oxadiazolyl and oxazolyl groups may optionally be substituted with 1 to 3 substituents independently selected from the group consisting of $C_{1-4}$-alkyl-O—, $F_3C$—, $F_3CO$—, $F_2HCO$—, $FH_2CO$—, cyano, halogen, and $C_{1-3}$-alkyl-.

In a further embodiment of the present invention
$R^6$ is selected independently of each other from the group $R^{6c}$ consisting of H, $C_{1-3}$-alkyl-, $C_{1-4}$-alkyl-C(O)—, phenyl-C(O)— and $C_{1-4}$-alkyl-O—C(O)—
wherein above mentioned $C_{1-3}$-alkyl-, $C_{1-4}$-alkyl-C(O)—, and $C_{1-4}$-alkyl-O—C(O)— groups may optionally be substituted with 1-9 fluorine atoms,
wherein the above mentioned phenyl-C(O)— group may optionally be substituted with 1 to 3 substituents independently selected from the group consisting of $C_{1-4}$-alkyl-O—, $F_3C$—, $F_3CO$—, $F_2HCO$—, $FH_2CO$—, cyano, halogen, and $C_{1-3}$-alkyl-.

In a further embodiment of the present invention
$R^7$ is selected the group $R^{7b}$ consisting of H.

In a further embodiment of the present invention
$R^8$ is selected from the group $R^{8b}$ consisting of H, $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$— and $R^9O$—,
wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-, and
wherein above mentioned $C_{1-4}$-alkyl-O—, $C_{3-6}$-cycloalkyl-O—, heterocyclyl-O—, $(C_{1-4}$-alkyl$)_2N$—, $(C_{1-4}$-alkyl)-C(O)—, $(C_{1-4}$-alkyl)-O—C(O)—, $(C_{1-4}$-alkyl)-HN—C(O)—, $(C_{1-4}$- alkyl)$_2$N—C(O)—, C$_{1-4}$-alkyl-O—C$_{1-4}$-alkyl- and C$_{1-6}$-alkyl-groups may optionally be substituted with 1 to 13 fluorine atoms.

In a further embodiment of the present invention
R$^8$ is selected from the group R$^8$ consisting of
H, C$_{1-8}$-alkyl-, C$_{3-6}$-cycloalkyl-, C$_{3-6}$-cycloalkyl-C$_{1-3}$-alkyl-, C-linked heterocyclyl, aryl, heteroaryl, and R$^9$O—,
wherein above mentioned C$_{1-8}$-alkyl-, C$_{3-6}$-cycloalkyl-, C$_{3-6}$-cycloalkyl-C$_{1-3}$-alkyl-, C-linked heterocyclyl, aryl and heteroaryl groups may optionally be substituted with 1 to 3 substituents independently selected from the group consisting of oxo, C$_{1-4}$-alkyl-O—, C$_{3-6}$-cycloalkyl-O—, heterocyclyl-O—, cyano, halogen, C$_{1-4}$-alkyl-O—C$_{1-4}$-alkyl- and C$_{1-6}$-alkyl-, and
wherein above mentioned C$_{1-4}$-alkyl-O—, C$_{3-6}$-cycloalkyl-O—, heterocyclyl-O—, C$_{1-4}$-alkyl-O—C$_{1-4}$-alkyl- and C$_{1-6}$-alkyl-groups may optionally be substituted with 1 to 13 fluorine atoms.

In a further embodiment of the present invention
R$^{8d}$ is selected from the group R$^{8d}$ consisting of
H, C$_{1-6}$-alkyl-, C$_{3-6}$-cycloalkyl-, aryl and R$^9$O—,
wherein above mentioned C$_{1-6}$-alkyl-, C$_{3-6}$-cycloalkyl- and aryl groups may optionally be substituted with 1 to 3 substituents independently selected from the group consisting of C$_{1-3}$-alkyl-O—, cyano, halogen, and C$_{1-3}$-alkyl-, and
wherein above mentioned C$_{1-3}$-alkyl-O—, C$_{1-3}$-alkyl-groups may optionally be substituted with 1 to 7 fluorine atoms.

In a further embodiment of the present invention
R$^8$ is selected from the group R$^{8e}$ consisting of
H, aryl and C$_{1-3}$-alkyl-O—,
wherein above mentioned aryl group may optionally be substituted with 1 to 3 substituents independently selected from the group consisting of cyano, F$_3$C— and halogen.

In a further embodiment of the present invention
R$^8$ is selected from the group R$^{8f}$ consisting of
H, phenyl and C$_{1-3}$-alkyl-O—,
wherein above mentioned phenyl group may optionally be substituted with 1 to 3 substituents independently selected from the group consisting of cyano, F$_3$C— and fluoro.

In a further embodiment of the present invention
R$^9$ is selected from the group R$^{9b}$ consisting of
H, C$_{1-6}$-alkyl-, aryl, C$_{3-6}$-cycloalkyl-, C$_{3-6}$-cycloalkyl-C$_{1-3}$-alkyl- and C$_{3-6}$-cycloalkyl-O—C$_{2-3}$-alkyl-,
wherein above mentioned C$_{1-6}$-alkyl-, C$_{3-6}$-cycloalkyl-, C$_{3-6}$-cycloalkyl-C$_{1-3}$-alkyl- and C$_{3-6}$-cycloalkyl-O—C$_{2-3}$-alkyl-groups may optionally be substituted with 1 to 3 substituents independently selected from the group consisting of C$_{1-4}$-alkyl-O—, halogen, cyano, HO— and oxo, wherein above mentioned aryl group may optionally be substituted with 1 to 3 substituents independently selected from the group consisting of C$_{1-4}$-alkyl-O—, F$_3$CO—, F$_2$HCO—, FH$_2$CO—, cyano, halogen and C$_{1-3}$-alkyl- which is optionally fluorinated with 1 to 7 fluorine atoms.

In a further embodiment of the present invention
R$^9$ is selected from the group R$^{9c}$ consisting of
H, phenyl and C$_{1-3}$-alkyl-,
wherein above mentioned C$_{1-3}$-alkyl-group may optionally be substituted with 1 to 3 substituents independently selected from the group consisting of halogen and cyano,
wherein above mentioned phenyl group may optionally be substituted with 1 to 3 substituents independently selected from the group consisting of cyano, halogen and C$_{1-3}$-alkyl- which is optionally fluorinated with 1 to 7 fluorine atoms.

In a further embodiment of the present invention
n is 0, 1, 2 or 3.

In a further embodiment of the present invention
n is 0, 1 or 2.

In a further embodiment of the present invention
n is 0 or 1.

Each R$^{1x}$, R$^{2x}$, R$^{3x}$, R$^{4x/5x}$, R$^{6x}$, R$^{7x}$, R$^{8x}$, R$^{9x}$, A$^x$, B$^x$, D$^x$, and W$^x$ represents a characterized, individual embodiment for the corresponding substituent as described above. Thus given the above definitions, preferred individual embodiments of the first aspect of the invention are fully characterized by the term (R$^{1x}$, R$^{2x}$, R$^{3x}$, R$^{4x/5x}$, R$^{6x}$, R$^{7x}$, R$^{8x}$, R$^{9x}$, A$^x$, B$^x$, D$^x$, and W$^x$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows, exemplarily and in the order of increasing preference from the first line to the last line, such embodiments E-1 to E-38 of the invention that are considered preferred. This means that embodiment E-38, represented by the entries in the last row of Table 1, is the most preferred embodiment.

TABLE 1

Preferred embodiments E-1 to E-38 of the invention

| | A$^x$ | B$^x$ | D$^x$ | W$^x$ | R$^{1x}$ | R$^{2x}$ | R$^{3x}$ | R$^{4x}$/R$^{5x}$ | R$^{6x}$ | R$^{7x}$ | R$^{8x}$ | R$^{9x}$ | n |
|---|---|---|---|---|---|---|---|---|---|---|---|---|---|
| E-1 | A$^b$ | B$^b$ | D$^b$ | W$^a$ | R$^{1b}$ | R$^{2b}$ | R$^{3a}$ | R$^{4b}$/R$^{5b}$ | R$^{6b}$ | R$^{7a}$ | R$^{8b}$ | R$^{9b}$ | 0, 1, 2, 3 |
| E-2 | A$^b$ | B$^b$ | D$^c$ | W$^a$ | R$^{1b}$ | R$^{2b}$ | R$^{3a}$ | R$^{4b}$/R$^{5b}$ | R$^{6b}$ | R$^{7a}$ | R$^{8b}$ | R$^{9b}$ | 0, 1, 2, 3 |
| E-3 | A$^b$ | B$^b$ | D$^c$ | W$^b$ | R$^{1b}$ | R$^{2c}$ | R$^{3a}$ | R$^{4d}$/R$^{5d}$ | R$^{6c}$ | R$^{7b}$ | R$^{8b}$ | R$^{9b}$ | 0, 1, 2, 3 |
| E-4 | A$^b$ | B$^b$ | D$^c$ | W$^b$ | R$^{1b}$ | R$^{2c}$ | R$^{3a}$ | R$^{4e}$/R$^{5e}$ | R$^{6c}$ | R$^{7b}$ | R$^{8b}$ | R$^{9b}$ | 0, 1, 2, 3 |
| E-5 | A$^b$ | B$^b$ | D$^c$ | W$^b$ | R$^{1b}$ | R$^{2c}$ | R$^{3a}$ | R$^{4f}$/R$^{5f}$ | R$^{6c}$ | R$^{7b}$ | R$^{8b}$ | R$^{9b}$ | 0, 1, 2, 3 |
| E-6 | A$^c$ | B$^c$ | D$^c$ | W$^b$ | R$^{1b}$ | R$^{2b}$ | R$^{3a}$ | R$^{4e}$/R$^{5e}$ | R$^{6b}$ | R$^{7a}$ | R$^{8c}$ | R$^{9b}$ | 0, 1, 2, 3 |
| E-7 | A$^c$ | B$^c$ | D$^c$ | W$^b$ | R$^{1b}$ | R$^{2b}$ | R$^{3a}$ | R$^{4f}$/R$^{5f}$ | R$^{6c}$ | R$^{7b}$ | R$^{8c}$ | R$^{9b}$ | 0, 1, 2, 3 |
| E-8 | A$^c$ | B$^c$ | D$^c$ | W$^b$ | R$^{1c}$ | R$^{2c}$ | R$^{3a}$ | — | R$^{6c}$ | R$^{7a}$ | R$^{8c}$ | R$^{9b}$ | 0, 1, 2, 3 |
| E-9 | A$^c$ | B$^c$ | D$^c$ | W$^b$ | R$^{1c}$ | R$^{2c}$ | R$^{3a}$ | — | R$^{6c}$ | R$^{7b}$ | R$^{8c}$ | R$^{9b}$ | 0, 1, 2, 3 |
| E-10 | A$^d$ | B$^c$ | D$^d$ | W$^b$ | R$^{1c}$ | R$^{2c}$ | R$^{3b}$ | — | R$^{6c}$ | R$^{7b}$ | R$^{8d}$ | R$^{9b}$ | 0, 1, 2, 3 |
| E-11 | A$^d$ | B$^c$ | D$^e$ | W$^b$ | R$^{1c}$ | R$^{2c}$ | R$^{3b}$ | — | R$^{6c}$ | R$^{7b}$ | R$^{8d}$ | R$^{9b}$ | 0, 1, 2, 3 |
| E-12 | A$^d$ | B$^c$ | D$^f$ | W$^b$ | R$^{1c}$ | R$^{2c}$ | R$^{3b}$ | — | — | R$^{7b}$ | R$^{8d}$ | R$^{9b}$ | 0, 1, 2, 3 |
| E-13 | A$^d$ | B$^c$ | D$^d$ | W$^b$ | R$^{1d}$ | R$^{2c}$ | R$^{3b}$ | — | R$^{6c}$ | R$^{7b}$ | R$^{8d}$ | R$^{9b}$ | 0, 1, 2, 3 |

TABLE 1-continued

Preferred embodiments E-1 to E-38 of the invention

| | $A^x$ | $B^x$ | $D^x$ | $W^x$ | $R^{1x}$ | $R^{2x}$ | $R^{3x}$ | $R^{4x}/R^{5x}$ | $R^{6x}$ | $R^{7x}$ | $R^{8x}$ | $R^{9x}$ | n |
|---|---|---|---|---|---|---|---|---|---|---|---|---|---|
| E-14 | $A^d$ | $B^c$ | $D^e$ | $W^b$ | $R^{1e}$ | $R^{2d}$ | $R^{3c}$ | — | $R^{6c}$ | $R^{7b}$ | $R^{8d}$ | $R^{9b}$ | 0, 1, 2, 3 |
| E-15 | $A^d$ | $B^c$ | $D^f$ | $W^b$ | $R^{1f}$ | $R^{2e}$ | $R^{3c}$ | — | — | $R^{7b}$ | $R^{8d}$ | $R^{9b}$ | 0, 1, 2, 3 |
| E-16 | $A^e$ | $B^c$ | $D^d$ | $W^b$ | $R^{1c}$ | $R^{2c}$ | $R^{3b}$ | — | $R^{6c}$ | $R^{7b}$ | $R^{8d}$ | $R^{9c}$ | 0, 1, 2, 3 |
| E-17 | $A^e$ | $B^c$ | $D^e$ | $W^b$ | $R^{1c}$ | $R^{2c}$ | $R^{3b}$ | — | $R^{6c}$ | $R^{7b}$ | $R^{8d}$ | $R^{9c}$ | 0, 1, 2, 3 |
| E-18 | $A^e$ | $B^c$ | $D^f$ | $W^b$ | $R^{1c}$ | $R^{2c}$ | $R^{3b}$ | — | — | $R^{7b}$ | $R^{8d}$ | $R^{9c}$ | 0, 1, 2, 3 |
| E-19 | $A^e$ | $B^c$ | $D^d$ | $W^b$ | $R^{1d}$ | $R^{2c}$ | $R^{3b}$ | — | $R^{6c}$ | $R^{7b}$ | $R^{8d}$ | $R^{9c}$ | 0, 1, 2, 3 |
| E-20 | $A^e$ | $B^c$ | $D^e$ | $W^b$ | $R^{1d}$ | $R^{2c}$ | $R^{3b}$ | — | $R^{6c}$ | $R^{7b}$ | $R^{8d}$ | $R^{9c}$ | 0, 1, 2, 3 |
| E-21 | $A^e$ | $B^c$ | $D^f$ | $W^b$ | $R^{1d}$ | $R^{2c}$ | $R^{3b}$ | — | — | $R^{7b}$ | $R^{8d}$ | $R^{9c}$ | 0, 1, 2, 3 |
| E-22 | $A^e$ | $B^c$ | $D^d$ | $W^b$ | $R^{1e}$ | $R^{2c}$ | $R^{3b}$ | — | $R^{6c}$ | $R^{7b}$ | $R^{8d}$ | $R^{9c}$ | 0, 1, 2, 3 |
| E-23 | $A^e$ | $B^c$ | $D^e$ | $W^b$ | $R^{1e}$ | $R^{2c}$ | $R^{3b}$ | — | $R^{6c}$ | $R^{7b}$ | $R^{8d}$ | $R^{9c}$ | 0, 1, 2, 3 |
| E-24 | $A^e$ | $B^c$ | $D^f$ | $W^b$ | $R^{1e}$ | $R^{2c}$ | $R^{3b}$ | — | — | $R^{7b}$ | $R^{8d}$ | $R^{9c}$ | 0, 1, 2, 3 |
| E-25 | $A^e$ | $B^c$ | $D^d$ | $W^b$ | $R^{1f}$ | $R^{2c}$ | $R^{3b}$ | — | $R^{6c}$ | $R^{7b}$ | $R^{8d}$ | $R^{9c}$ | 0, 1, 2, 3 |
| E-26 | $A^e$ | $B^c$ | $D^e$ | $W^b$ | $R^{1f}$ | $R^{2c}$ | $R^{3b}$ | — | $R^{6c}$ | $R^{7b}$ | $R^{8d}$ | $R^{9c}$ | 0, 1, 2, 3 |
| E-27 | $A^e$ | $B^c$ | $D^f$ | $W^b$ | $R^{1f}$ | $R^{2c}$ | $R^{3b}$ | — | — | $R^{7b}$ | $R^{8d}$ | $R^{9c}$ | 0, 1, 2, 3 |
| E-28 | $A^e$ | $B^c$ | $D^d$ | $W^b$ | $R^{1f}$ | $R^{2d}$ | $R^{3b}$ | — | $R^{6c}$ | $R^{7b}$ | $R^{8d}$ | $R^{9c}$ | 0, 1, 2, 3 |
| E-29 | $A^e$ | $B^c$ | $D^e$ | $W^b$ | $R^{1f}$ | $R^{2d}$ | $R^{3b}$ | — | $R^{6c}$ | $R^{7b}$ | $R^{8d}$ | $R^{9c}$ | 0, 1, 2, 3 |
| E-30 | $A^e$ | $B^c$ | $D^f$ | $W^b$ | $R^{1f}$ | $R^{2d}$ | $R^{3b}$ | — | — | $R^{7b}$ | $R^{8d}$ | $R^{9c}$ | 0, 1, 2, 3 |
| E-31 | $A^e$ | $B^c$ | $D^d$ | $W^b$ | $R^{1f}$ | $R^{2e}$ | $R^{3b}$ | — | $R^{6c}$ | $R^{7b}$ | $R^{8d}$ | $R^{9c}$ | 0, 1, 2, 3 |
| E-32 | $A^e$ | $B^c$ | $D^d$ | $W^b$ | $R^{1f}$ | $R^{2e}$ | $R^{3c}$ | — | $R^{6c}$ | $R^{7b}$ | $R^{8d}$ | $R^{9c}$ | 0, 1, 2, 3 |
| E-33 | $A^e$ | $B^c$ | $D^e$ | $W^b$ | $R^{1f}$ | $R^{2e}$ | $R^{3b}$ | — | $R^{6c}$ | $R^{7b}$ | $R^{8d}$ | $R^{9c}$ | 0, 1, 2, 3 |
| E-34 | $A^e$ | $B^c$ | $D^e$ | $W^b$ | $R^{1f}$ | $R^{2e}$ | $R^{3c}$ | — | $R^{6c}$ | $R^{7b}$ | $R^{8d}$ | $R^{9c}$ | 0, 1, 2, 3 |
| E-35 | $A^e$ | $B^c$ | $D^f$ | $W^b$ | $R^{1f}$ | $R^{2e}$ | $R^{3b}$ | — | — | $R^{7b}$ | $R^{8e}$ | — | 0, 1, 2, 3 |
| E-36 | $A^e$ | $B^c$ | $D^f$ | $W^b$ | $R^{1f}$ | $R^{2e}$ | $R^{3c}$ | — | — | $R^{7b}$ | $R^{8f}$ | — | 0, 1, 2, 3 |
| E-37 | $A^e$ | $B^c$ | $D^f$ | $W^b$ | $R^{1f}$ | $R^{2e}$ | $R^{3c}$ | — | — | $R^{7b}$ | $R^{8f}$ | — | 0, 1, 2 |
| E-38 | $A^e$ | $B^c$ | $D^f$ | $W^b$ | $R^{1f}$ | $R^{2e}$ | $R^{3c}$ | — | — | $R^{7b}$ | $R^{8f}$ | — | 0, 1 | the tautomers thereof, the stereoisomers thereof, the mixtures thereof, and the salts thereof.

Accordingly, for example E-38 covers compounds of formula I, wherein

A is selected from the group $A^e$ consisting of

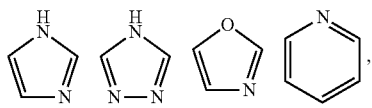

wherein above mentioned groups may optionally be substituted with 1 or 2 substituents independently selected from the group consisting of halogen and $C_{1-3}$-alkyl- which is optionally fluorinated with 1 to 7 fluorine atoms;

B is selected from the group $B^c$ consisting of

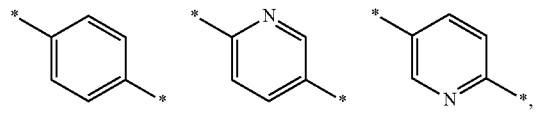

wherein above mentioned phenyl- and pyridinyl- groups may optionally be substituted with 1 or 2 substituents independently selected from the group consisting of halogen, cyano, $C_{1-3}$-alkyl- which is optionally fluorinated with 1 to 7 fluorine atoms, and $C_{1-3}$-alkyl-O— which is optionally fluorinated with 1 to 7 fluorine atoms;

D is selected from the group $D^f$ consisting of

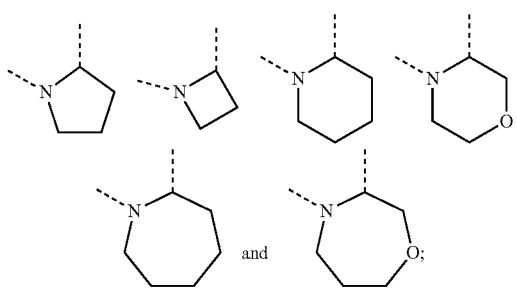

and

W is selected from the group $W^b$ consisting of
—($R^7$)N—;

$R^1$ is selected from the group $R^{1f}$ consisting of
H, $C_{1-4}$-alkyl-, $C_{3-6}$-cycloalkyl- and benzyl-,
wherein above mentioned $C_{1-4}$-alkyl- and $C_{3-6}$-cycloalkyl-groups may optionally be substituted with 1 to 11 fluorine atoms, and
wherein above mentioned benzyl- group may optionally be substituted with 1 to 3 substituents independently selected from the group consisting of $C_{1-3}$-alkyl-O—, cyano, halogen, and $C_{1-3}$-alkyl-, and
wherein above mentioned $C_{1-3}$-alkyl-O— and $C_{1-3}$-alkyl-groups may optionally be substituted with 1 to 7 fluorine atoms;

$R^2$ is selected from the group $R^{2e}$ consisting of
H, $C_{1-3}$-alkyl-O—$C_{1-3}$-alkyl- and $C_{1-3}$-alkyl-;

$R^3$ is selected from the group $R^{3c}$ consisting of
H and $H_3C$—;

$R^7$ is selected the group $R^{7b}$ consisting of
H;

$R^8$ is selected from the group $R^{8f}$ consisting of
H, phenyl and $C_{1-3}$-alkyl-O—,
wherein above mentioned phenyl group may optionally be substituted with 1 to 3 substituents independently selected from the group consisting of cyano, $F_3C$— and fluoro;

n is 0 or 1;

the tautomers thereof, the stereoisomers thereof, the mixtures thereof, and the salts thereof.

Further preferred are the following compounds listed in table 2:

| No. | Structure |
|---|---|
| I | 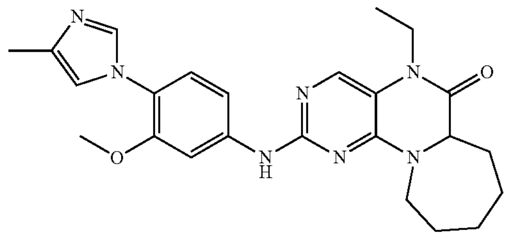 [SMILES: CCN1C(=O)C2CCCCCN2c2nc(Nc3ccc(-n4cnc(C)c4)c(OC)c3)ncc21] |
| II | 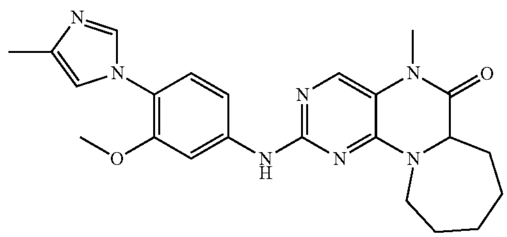 [SMILES: COc1cc(Nc2ncc3c(n2)N2CCCCCC2C(=O)N3C)ccc1-n1cnc(C)c1] |
| III | 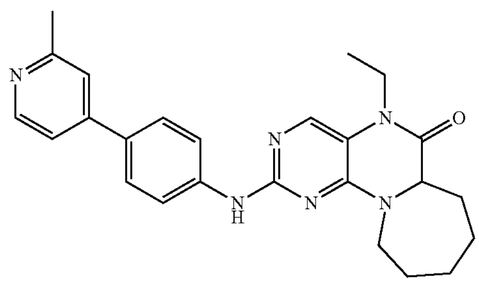 [SMILES: CCN1C(=O)C2CCCCCN2c2nc(Nc3ccc(-c4ccnc(C)c4)cc3)ncc21] |
| IV | 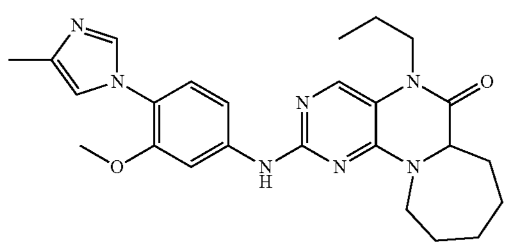 [SMILES: CCCN1C(=O)C2CCCCCN2c2nc(Nc3ccc(-n4cnc(C)c4)c(OC)c3)ncc21] |
| V | 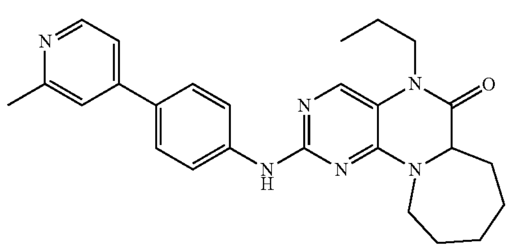 [SMILES: CCCN1C(=O)C2CCCCCN2c2nc(Nc3ccc(-c4ccnc(C)c4)cc3)ncc21] |
| VI | 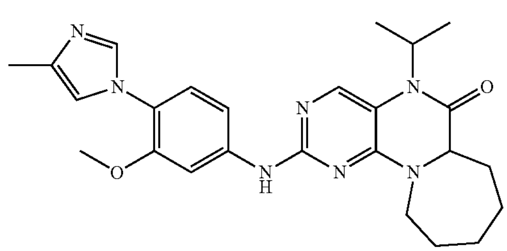 [SMILES: COc1cc(Nc2ncc3c(n2)N2CCCCCC2C(=O)N3C(C)C)ccc1-n1cnc(C)c1] |

-continued
| No. | Structure |
|---|---|
| VII | 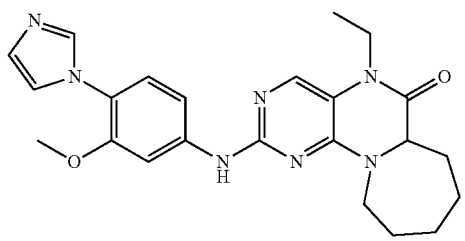 [SMILES: CCN1C(=O)C2CCCCCN2c2nc(Nc3ccc(-n4ccnc4)c(OC)c3)ncc21] |
| VIII | 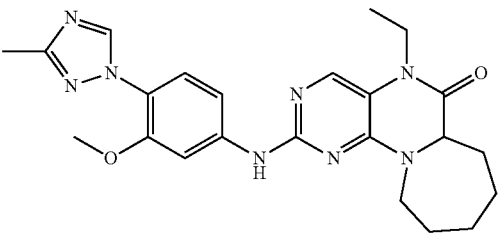 [SMILES: CCN1C(=O)C2CCCCCN2c2nc(Nc3ccc(-n4cnc(C)n4)c(OC)c3)ncc21] |
| IX | 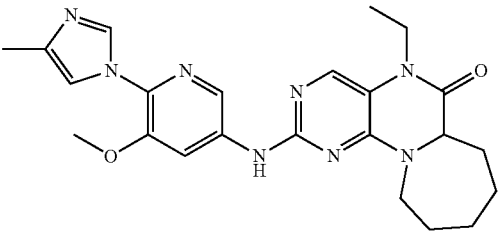 |
| X | 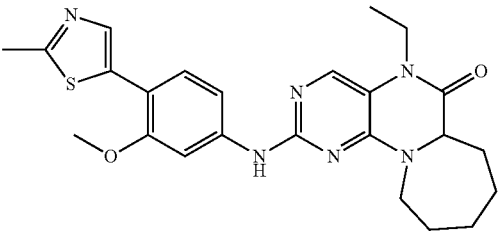 [SMILES: CCN1C(=O)C2CCCCCN2c2nc(Nc3ccc(-c4cnc(C)s4)c(OC)c3)ncc21] |
| XI | 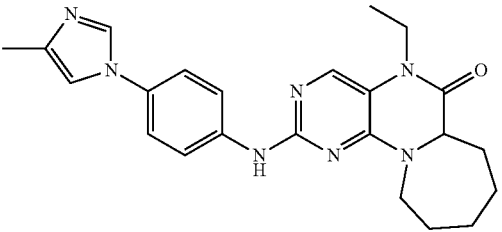 [SMILES: CCN1C(=O)C2CCCCCN2c2nc(Nc3ccc(-n4cnc(C)c4)cc3)ncc21] |
| XII | 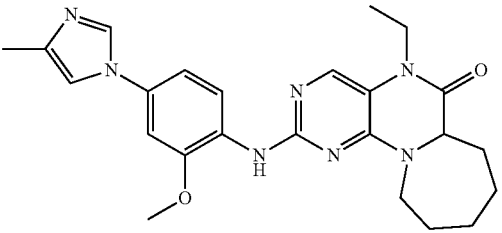 [SMILES: CCN1C(=O)C2CCCCCN2c2nc(Nc3ccc(-n4cnc(C)c4)cc3OC)ncc21] |

-continued
| No. | Structure |
|---|---|
| XIII | 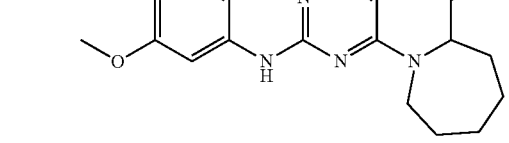 |
| XIV | 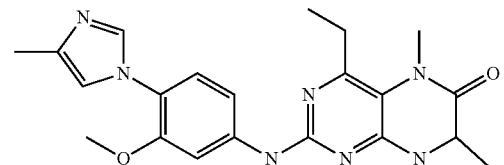 |
| XV | 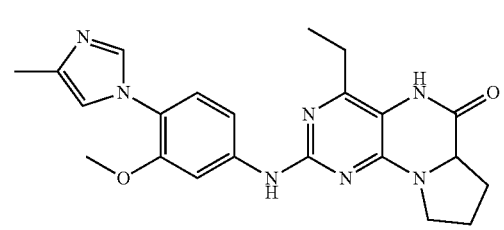 [SMILES: CCc1nc(Nc2ccc(-n3cnc(C)c3)c(OC)c2)nc2c1NC(=O)C1CCCN21] |
| XVI | 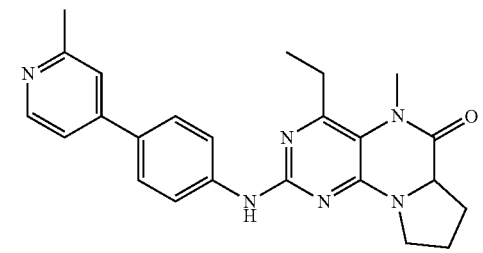 |
| XVII | 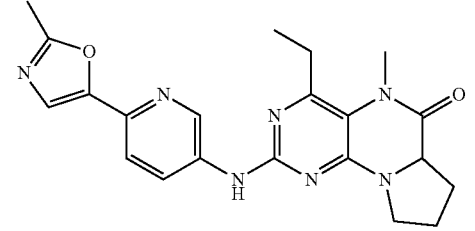 [SMILES: CCc1nc(Nc2ccc(-c3cnc(C)o3)nc2)nc2c1N(C)C(=O)C1CCCN21] |
| XVIII | 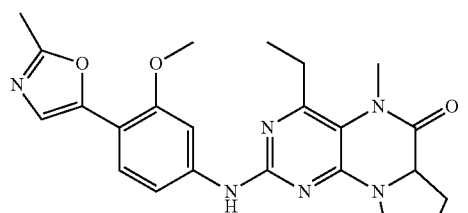 |

-continued
| No. | Structure |
|---|---|
| XIX | 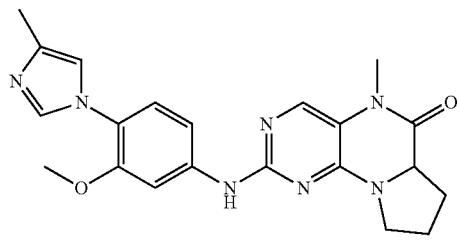 [SMILES: COc1cc(Nc2ncc3c(n2)N2CCCC2C(=O)N3C)ccc1-n1cnc(C)c1] |
| XX | 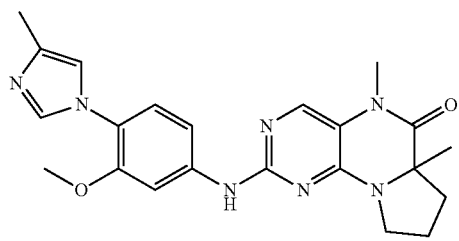 [SMILES: COc1cc(Nc2ncc3c(n2)N2CCCC2(C)C(=O)N3C)ccc1-n1cnc(C)c1] |
| XXI | 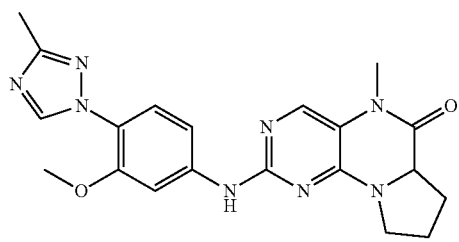 [SMILES: COc1cc(Nc2ncc3c(n2)N2CCCC2C(=O)N3C)ccc1-n1cnc(C)n1] |
| XXII | 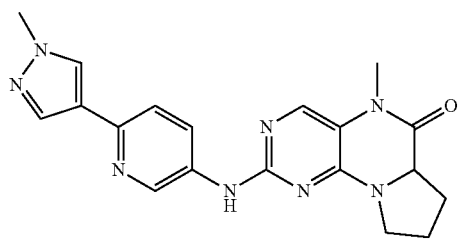 [SMILES: CN1C(=O)C2CCCN2c2nc(Nc3ccc(-c4cnn(C)c4)nc3)ncc21] |
| XXIII | 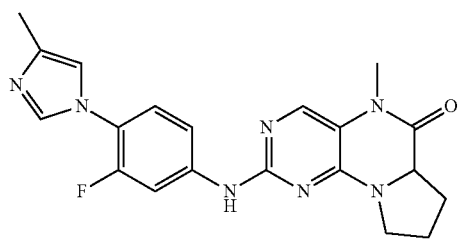 [SMILES: Cc1cn(-c2ccc(Nc3ncc4c(n3)N3CCCC3C(=O)N4C)cc2F)cn1] |
| XXIV | 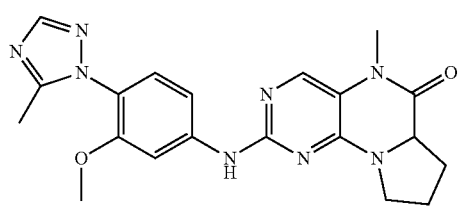 [SMILES: COc1cc(Nc2ncc3c(n2)N2CCCC2C(=O)N3C)ccc1-n1ncnc1C] |

-continued

| No. | Structure |
|---|---|
| XXV | 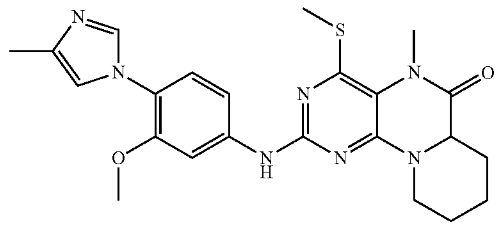 [SMILES: COc1cc(Nc2nc(SC)c3c(n2)N2CCCCC2C(=O)N3C)ccc1-n1cnc(C)c1] |
| XXVI | 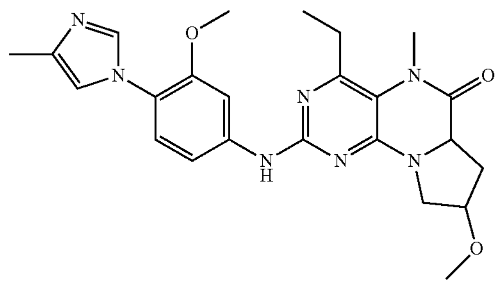 [SMILES: CCc1nc(Nc2ccc(-n3cnc(C)c3)c(OC)c2)nc2c1N(C)C(=O)C1CC(OC)CN21] |
| XXVII | 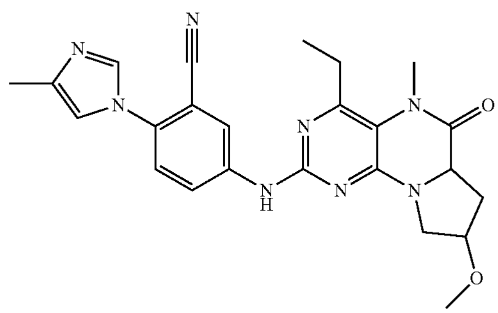 [SMILES: CCc1nc(Nc2ccc(-n3cnc(C)c3)c(C#N)c2)nc2c1N(C)C(=O)C1CC(OC)CN21] |
| XXVIII | 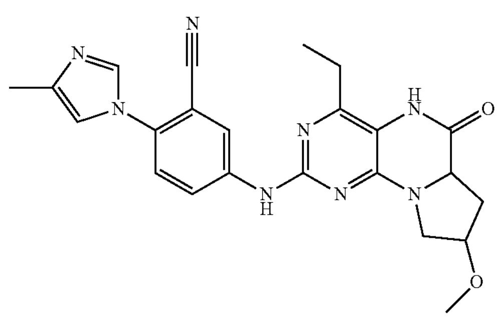 [SMILES: CCc1nc(Nc2ccc(-n3cnc(C)c3)c(C#N)c2)nc2c1NC(=O)C1CC(OC)CN21] |
| XXIX | 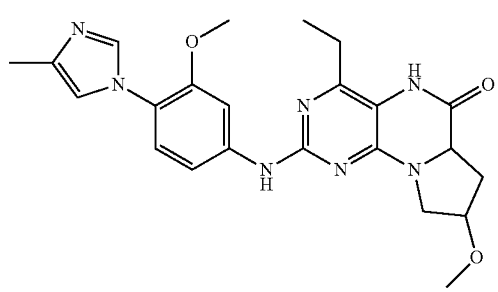 [SMILES: CCc1nc(Nc2ccc(-n3cnc(C)c3)c(OC)c2)nc2c1NC(=O)C1CC(OC)CN21] |

-continued
| No. | Structure |
|---|---|
| XXX | 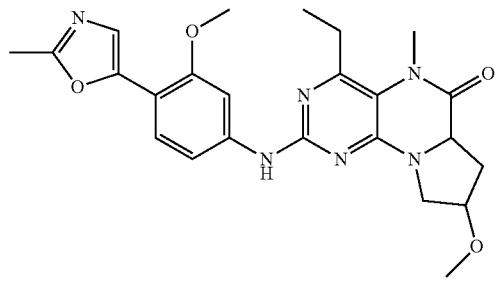 [SMILES: CCc1nc(Nc2ccc(-c3cnc(C)o3)c(OC)c2)nc2c1N(C)C(=O)C1CC(OC)CN21] |
| XXXI | 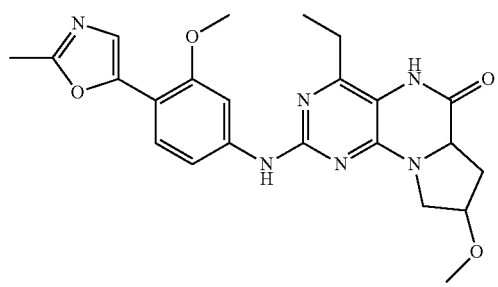 [SMILES: CCc1nc(Nc2ccc(-c3cnc(C)o3)c(OC)c2)nc2c1NC(=O)C1CC(OC)CN21] |
| XXXII | 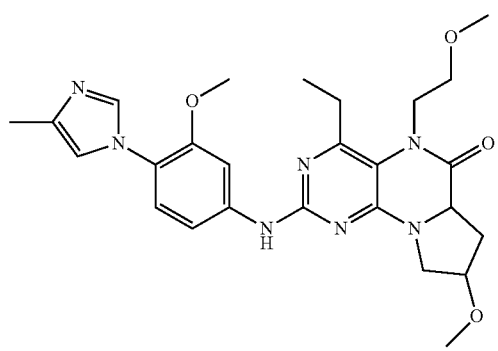 |
| XXXIII | 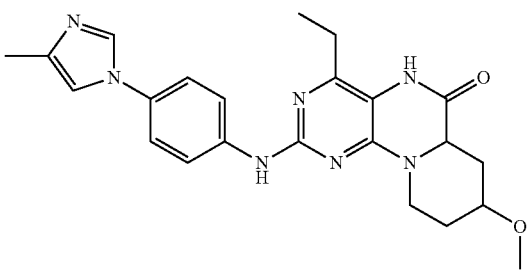 |
| XXXIV | 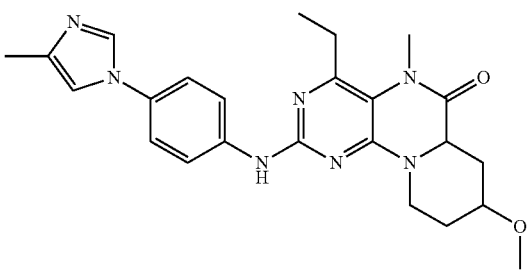 |

| No. | Structure |
|---|---|
| XXXV | 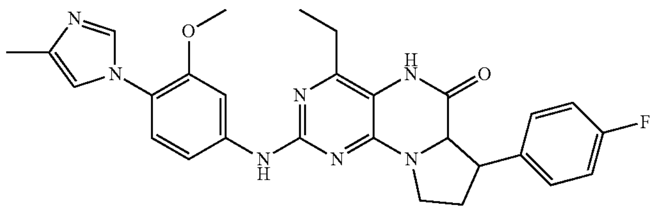 [SMILES: CCc1nc(Nc2ccc(-n3cnc(C)c3)c(OC)c2)nc2c1NC(=O)C1C(c3ccc(F)cc3)CCN21] |
| XXXVI | 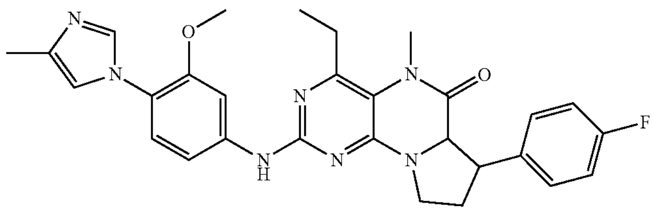 [SMILES: CCc1nc(Nc2ccc(-n3cnc(C)c3)c(OC)c2)nc2c1N(C)C(=O)C1C(c3ccc(F)cc3)CCN21] |
| XXXVII | 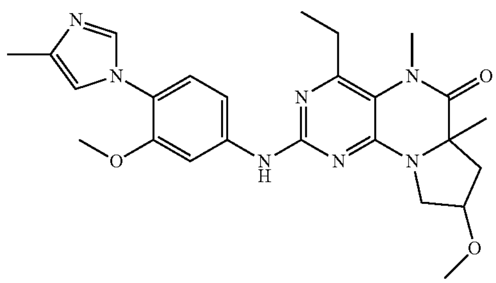 |
| XXXVIII | 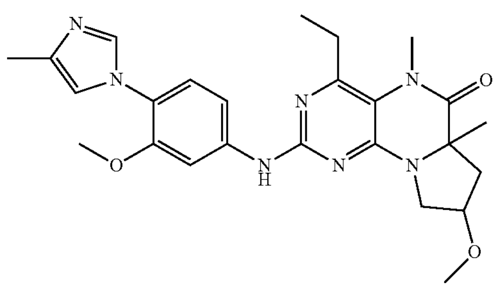 |
| XXXIX | 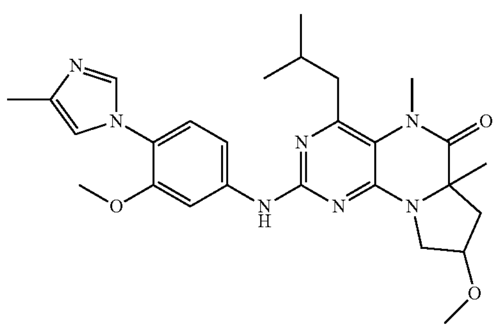 |
| XL | 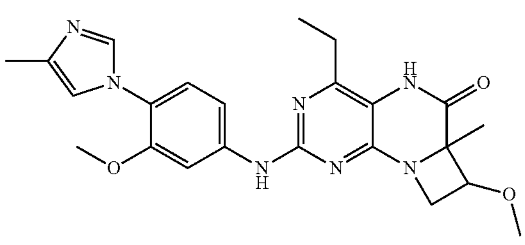 |

-continued
| No. | Structure |
|---|---|
| XLI | 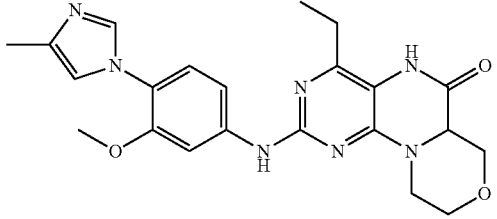 [SMILES: CCc1nc(Nc2ccc(-n3cnc(C)c3)c(OC)c2)nc2c1NC(=O)C1COCCN21] |
| XLII | 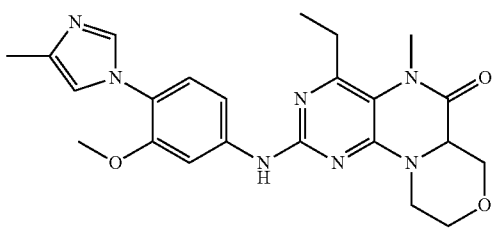 [SMILES: CCc1nc(Nc2ccc(-n3cnc(C)c3)c(OC)c2)nc2c1N(C)C(=O)C1COCCN21] |
| XLIII | 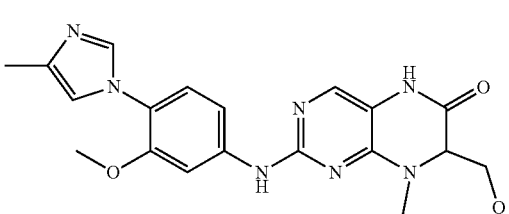 |
| XLIV | 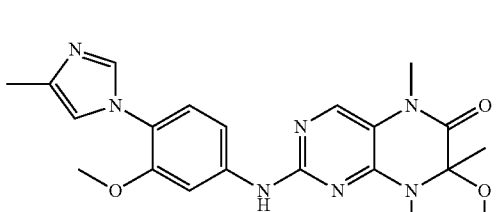 |
| XLV | 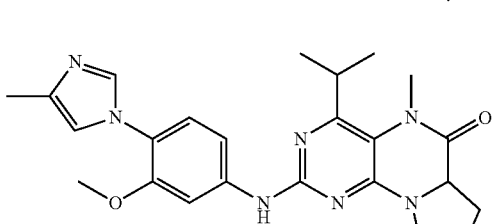 |
| XLVI | 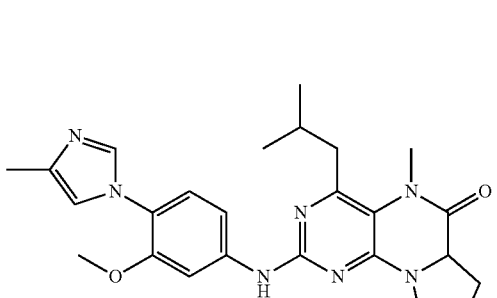 |

| No. | Structure |
|---|---|
| XLVII | 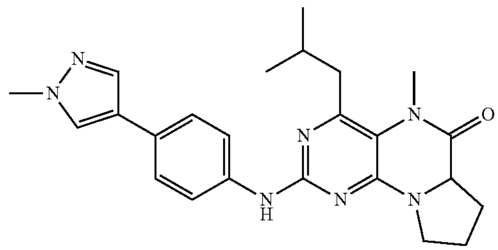 [SMILES: CC(C)Cc1nc(Nc2ccc(-c3cnn(C)c3)cc2)nc2c1N(C)C(=O)C1CCCN21] |
| XLVIII | 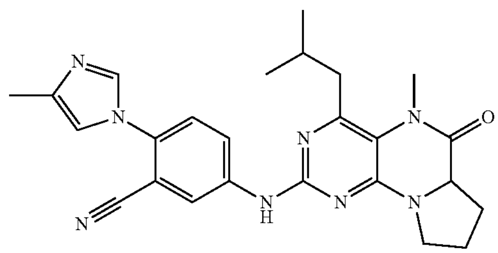 [SMILES: Cc1cn(-c2ccc(Nc3nc(CC(C)C)c4c(n3)N3CCCC3C(=O)N4C)cc2C#N)cn1] |
| IL | 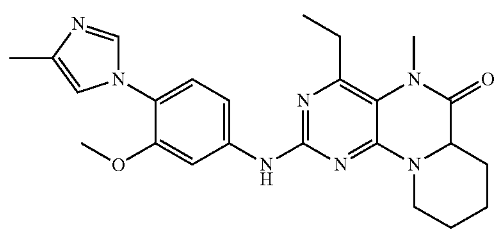 [SMILES: CCc1nc(Nc2ccc(-n3cnc(C)c3)c(OC)c2)nc2c1N(C)C(=O)C1CCCCN21] |
| L | 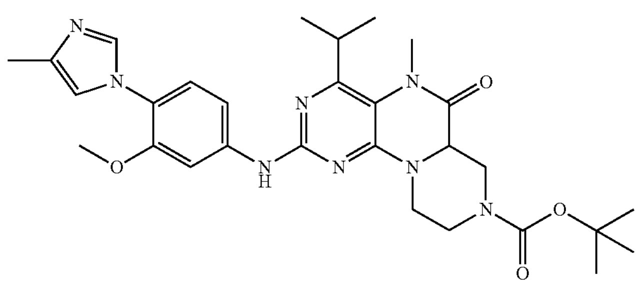 [SMILES: COc1cc(Nc2nc(C(C)C)c3c(n2)N2CCN(C(=O)OC(C)(C)C)CC2C(=O)N3C)ccc1-n1cnc(C)c1] |

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core molecule or to the group to which the substituent is attached.

Within the present invention, the term "core molecule" is defined by the following structure:

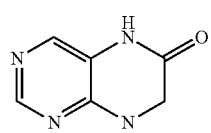

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

An asterisk may be used in sub-formulas to indicate the bond which is connected to the core molecule as defined.

The dotted lines in sub-formulas of substituent D indicate the atoms being part of the core molecule and the substituent D. For example, the substructure

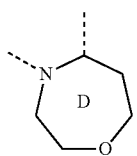

of substituent D means that the nitrogen and the carbon atoms to which the dotted lines are attached belong to the core molecule as well as to ring D resulting in the following structure:

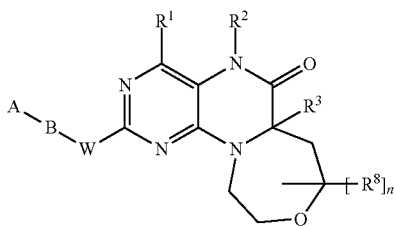

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

The term "C-linked heterocyclyl" as used herein means that the heterocyclyl group is connected to the core molecule according to formula I by a bond from a C-atom of the heterocyclyl ring.

The term "halogen" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. The term $C_{2-5}$-alkenyl includes for example the radicals $H_2C$=$CH$—, $H_2C$=$CH$—$CH_2$—, $H_3C$—$CH$=$CH$—, $H_2C$=$CH$—$CH_2$—$CH_2$—, $H_3C$—$CH$=$CH$—$CH_2$—, $H_3C$—$CH_2$—$CH$=$CH$—, $(H_3C)_2C$=$CH$—, $H_2C$=$CH$—$CH_2$—$CH_2$—$CH_2$—, $H_3C$—$CH$=$CH$—$CH_2$—$CH_2$—, $H_3C$—$CH_2$—$CH$=$CH$—

CH$_2$—, H$_3$C—CH$_2$—CH$_2$—CH=CH—, H$_2$C=CH—CH=CH—CH$_2$— and (H$_3$C)$_2$C=CH—CH$_2$—.

The term "C$_{2-n}$-alkynyl", is used for a group as defined in the definition for "C$_{1-n}$-alkyl" with at least two carbon atoms, if at least two of those carbon atoms of said group are bonded to each other by a triple bond. The term C$_{2-5}$-alkinyl includes for example the radicals HC≡C—, HC≡C—CH$_2$—, H$_3$C—C≡C—, HC≡C—CH$_2$—CH$_2$—, H$_3$C—C≡C—CH$_2$—, H$_3$C—CH$_2$—C≡C—, HC≡C—CH$_2$—CH$_2$—CH$_2$—, H$_3$C—C≡C—CH$_2$—CH$_2$—, H$_3$C—CH$_2$—C≡C—CH$_2$—, H$_3$C—CH$_2$—CH$_2$—C≡C— and (H$_3$C)$_2$CH—C≡C—.

The terms "carbocyclyl" and "carbocycle" as used either alone or in combination with another radical, mean, if not mentioned otherwise, a mono- bi- or tricyclic ring structure consisting of 3 to 14 carbon atoms. The terms, if not mentioned otherwise, refers to fully saturated, partially saturated and aromatic ring systems. The terms encompass fused, bridged and spirocyclic systems.

Thus, the terms include the following exemplary structures which are not depicted as radicals as each form may be attached through a covalent bond to any atom so long as appropriate valences are maintained:

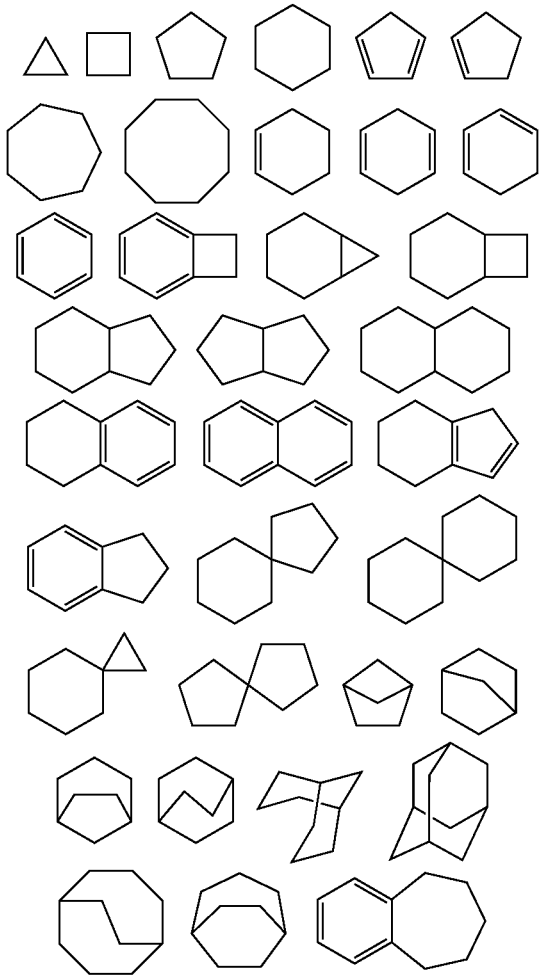

The term "C$_{3-n}$-cycloalkyl", wherein n is an integer from 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

The terms "heterocyclyl" and "heterocycle" as used either alone or in combination with another radical, mean a saturated or unsaturated mono- or polycyclic ring system containing one or more heteroatoms selected from N, O or S(O)$_r$, wherein r=0, 1 or 2, which may contain aromatic rings consisting of, if not mentioned otherwise, 3 to 14 ring atoms wherein none of the heteroatoms is part of an aromatic ring. The terms encompass fused, bridged and spirocyclic systems. The terms are intended to include all the possible isomeric forms.

Thus, the terms include the following exemplary structures which are not depicted as radicals as each form may be attached through a covalent bond to any atom so long as appropriate valences are maintained:

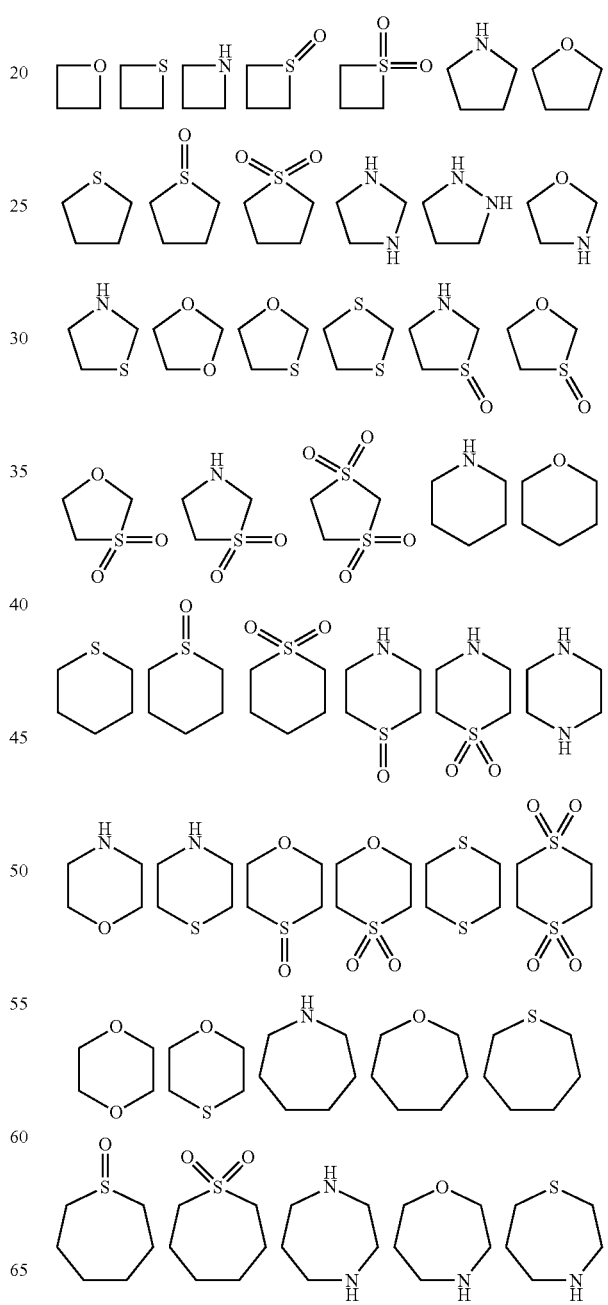

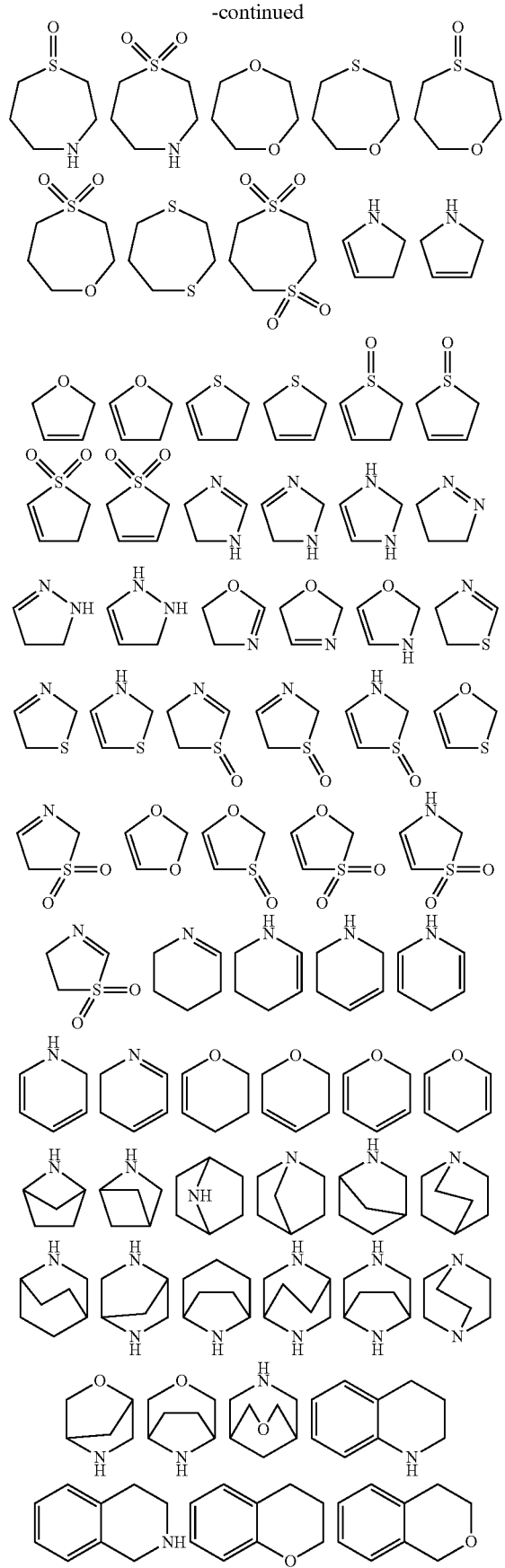
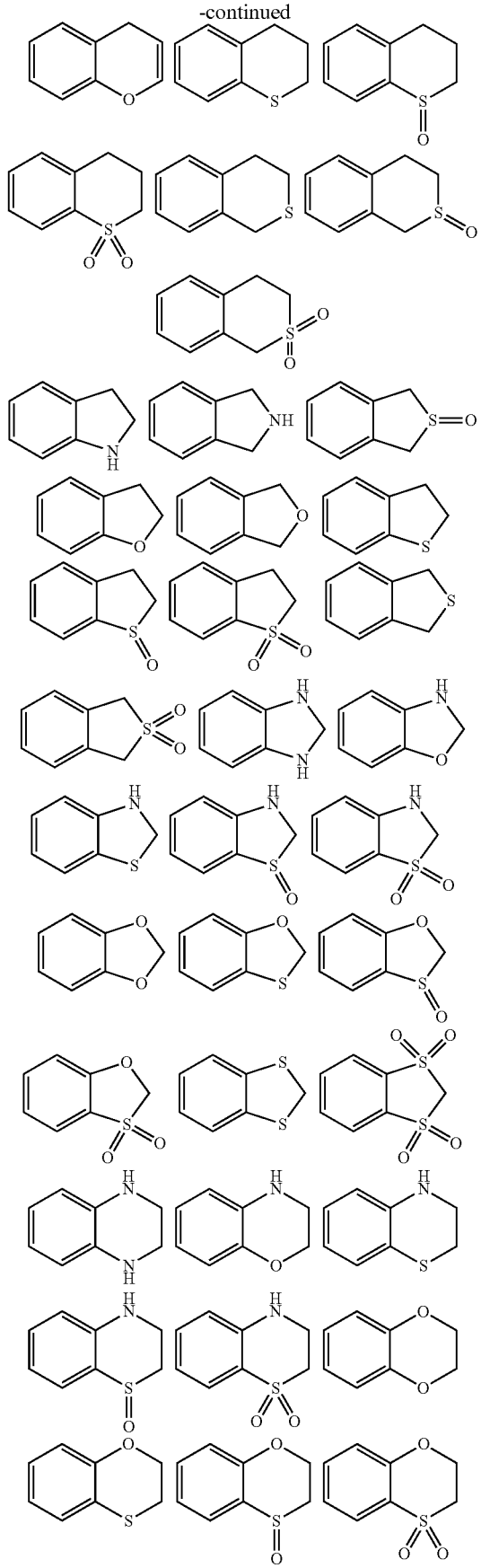

-continued

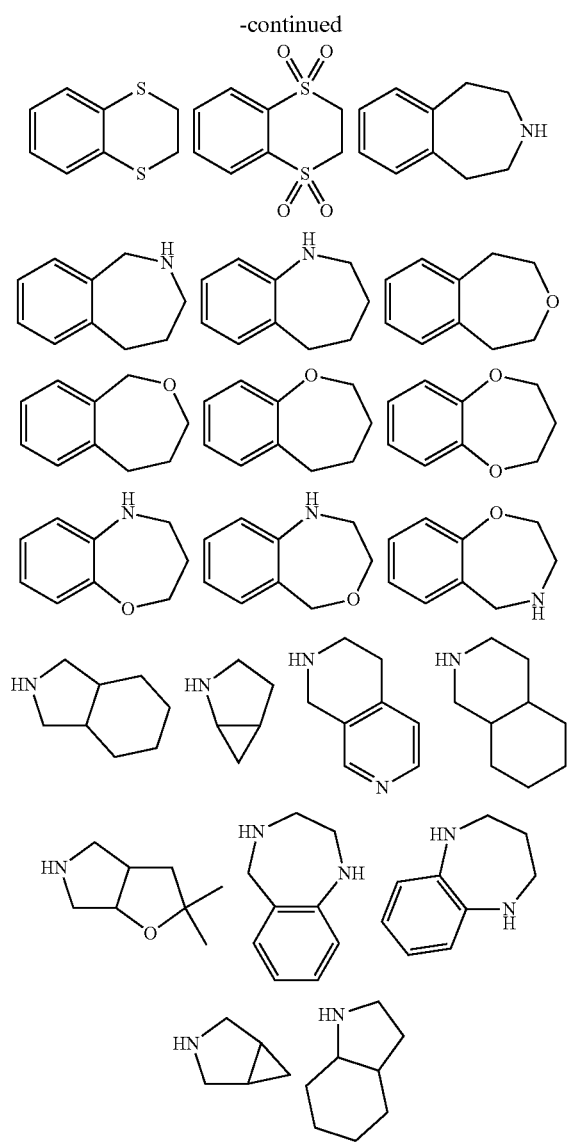

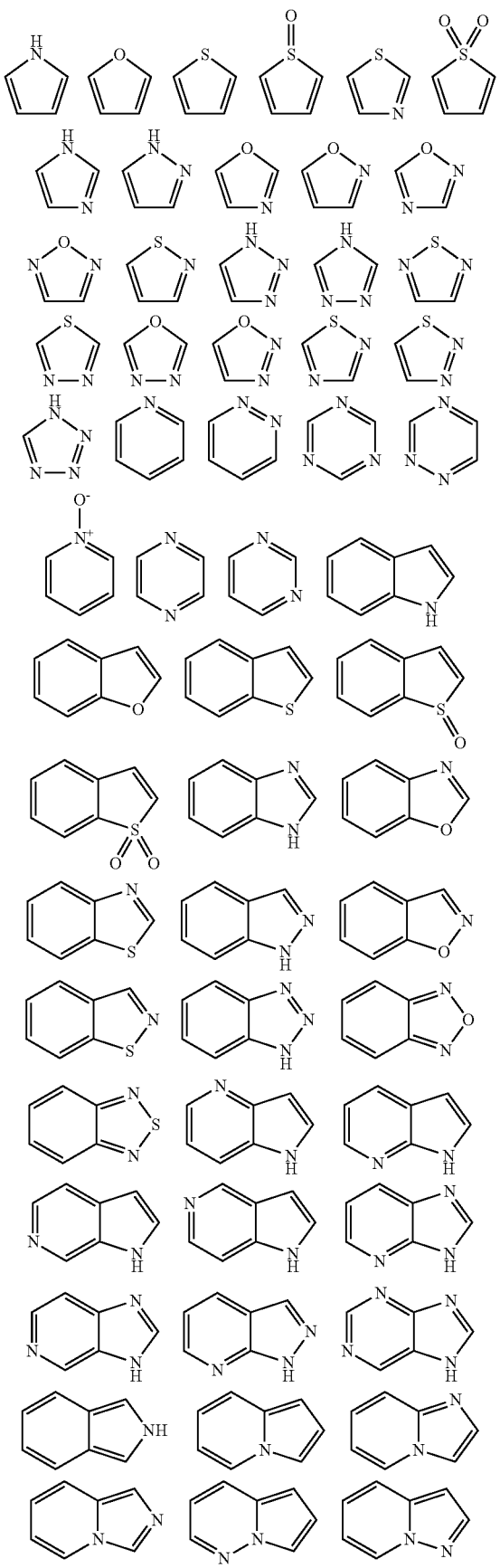

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

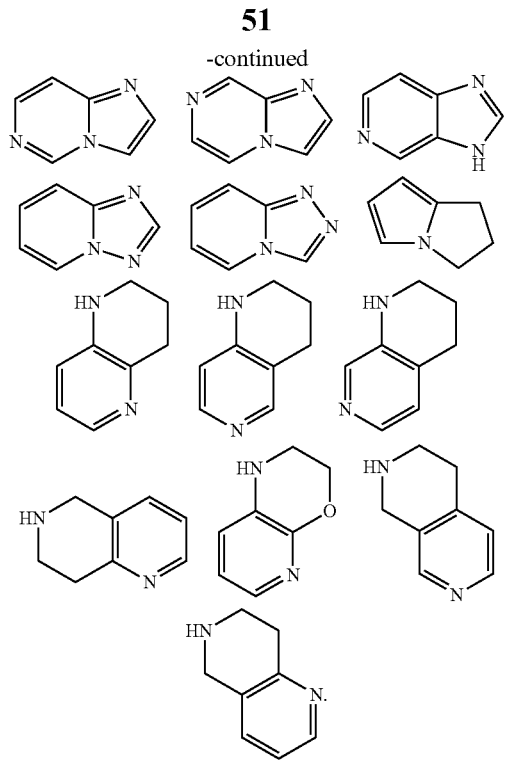

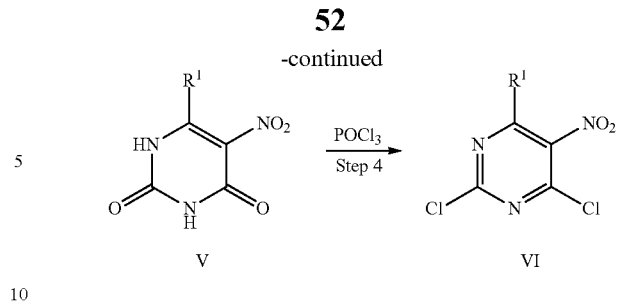

Scheme 1 illustrates the synthesis of 6-substituted 2,4-dichloro-5-nitro-pyrimidines (VI) als intermediates for the synthesis of dihydropteridinones (I):

In a first step 2,4,6-trichloro-pyrimidine (II) is reacted with Grignard reagents $R^1$—Mg—X (with X=Cl, Br, I, $R^1$) in an appropriate solvent like tetrahydrofurane in the presence of a Copper catalyst (e.g. Cu(I) iodide) to form 6-substituted 2,4-dichloro-pyrimidine derivatives (III). These compounds are converted in a second step to the corresponding 1H-pyrimidine-2,4-diones (IV) by heating with aqueous mineral acid (e.g. hydrochloric acid). In a third step, nitration, e.g. by using a mixture of sulfuric acid and nitric acid, leads to the corresponding 5-nitro-1H-pyrimidine-2,4-diones (V).

In a fourth step, these compounds are heated with phosphorus oxychloride resulting in the formation of 6-substituted 2,4-dichloro-5-nitro-pyrimidines (VI).

Many of the terms given above may be used repeatedly in the definition of a formula or group and in each case have one of the meanings given above, independently of one another.

The compounds according to the invention may be obtained using methods of synthesis known in principle. Preferably, the compounds are obtained by the following methods according to the invention which are described in more detail hereinafter.

The following schemes shall illustrate a process to manufacture the compounds of the present invention by way of example:

Scheme 1

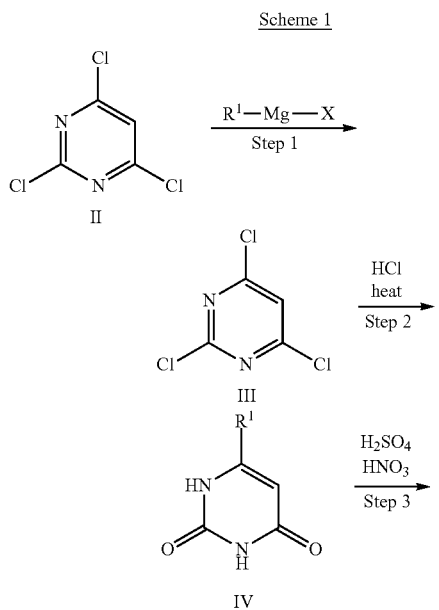

Scheme 2

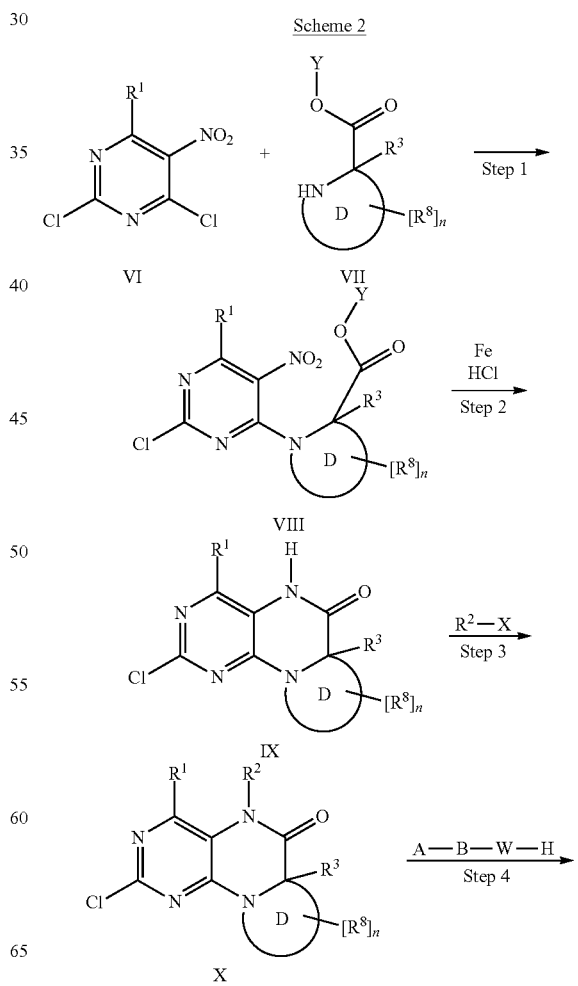

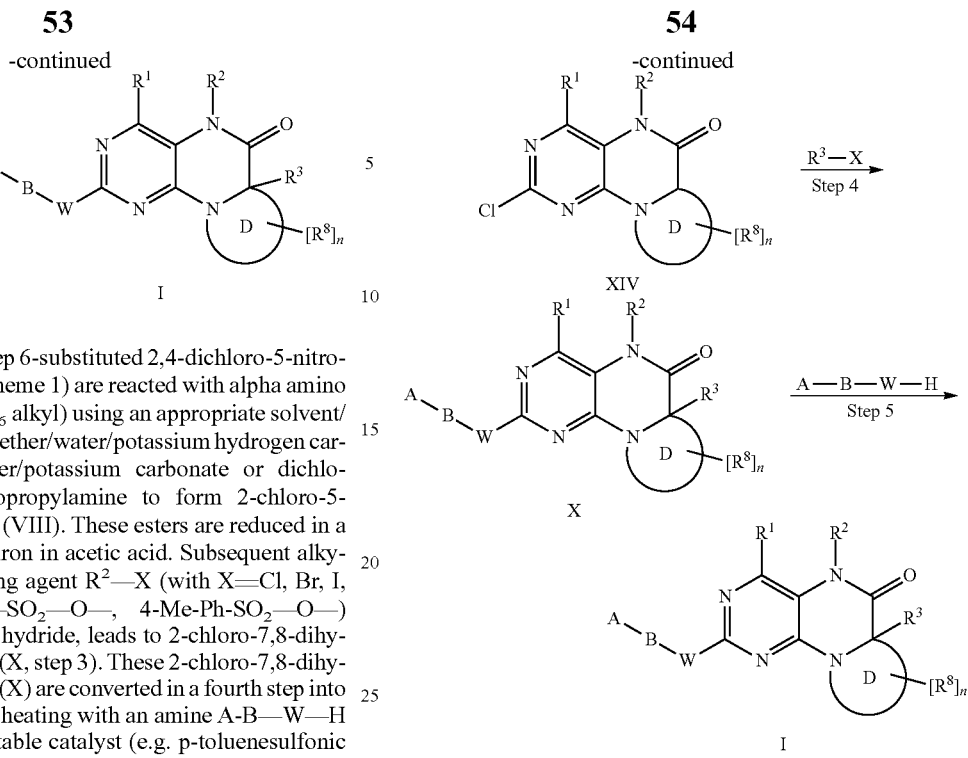

Scheme 2: In a first step 6-substituted 2,4-dichloro-5-nitro-pyrimidines (VI, see Scheme 1) are reacted with alpha amino acid esters (VII, Y=$C_{1-6}$ alkyl) using an appropriate solvent/base system like diethyl ether/water/potassium hydrogen carbonate or acetone/water/potassium carbonate or dichloromethane/N-ethyl-diisopropylamine to form 2-chloro-5-nitro-pyrimidinyl esters (VIII). These esters are reduced in a second step, e.g. using iron in acetic acid. Subsequent alkylation using an alkylating agent $R^2$—X (with X=Cl, Br, I, Me-$SO_2$—O—, $CF_3$—$SO_2$—O—, 4-Me-Ph-$SO_2$—O—) and a base, e.g. sodium hydride, leads to 2-chloro-7,8-dihydro-5H-pteridin-6-ones (X, step 3). These 2-chloro-7,8-dihydro-5H-pteridin-6-ones (X) are converted in a fourth step into the final products (I) by heating with an amine A-B—W—H in the presence of a suitable catalyst (e.g. p-toluenesulfonic acid in acetic acid) in a suitable solvent like 4-methyl-2-pentanol or N-methylpyrrolidone or dimethylsulfoxide to form the final dihydropteridinones (I). Alternatively, dihydropteridinones (I) can be obtained by heating 2-chloro-7,8-dihydro-5H-pteridin-6-ones (X) with an amine A-B—W—H in the presence of a suitable catalyst (e.g. Pd(OAc)$_2$ or Pd$_2$(dba)$_3$), a ligand (e.g. BINAP, dppf or Xantphos) and a base (e.g. cesium carbonate or potassium tert.-butoxide) in a suitable solvent like tetrahydrofurane, 1,4-dioxane.

Scheme 3: In a first step 6-substituted 2,4-dichloro-5-nitro-pyrimidines (VI, see Scheme 1) are reacted with alpha amino acid esters (XI, Y=$C_{1-6}$ alkyl) using an appropriate solvent/base system like diethyl ether/water/potassium hydrogen carbonate or acetone/water/potassium carbonate or dichloromethane/N-ethyl-diisopropylamine to form 2-chloro-5-nitro-pyrimidinyl esters (XII). These esters are reduced in a second step, e.g. using iron in acetic acid. Subsequent alkylation using an alkylating agent $R^2$—X (with X=Cl, Br, I, Me-$SO_2$—O—, $CF_3$—$SO_2$—O—, 4-Me-Ph-$SO_2$—O—) and a base, e.g. sodium hydride, leads to pteridinones (XIV, step 3). These pteridinones (XIV) are alkylated in the 7-position in a fourth step using an alkylating agent $R^3$—X (with X=Cl, Br, I, Me-$SO_2$—O—, $CF_3$—$SO_2$—O—, 4-Me-Ph-$SO_2$—O—) and a base, e.g. lithium diisopropyl amide in tetrahydrofurane leading to 2-chloro-7,8-dihydro-5H-pteridin-6-ones (X) that are converted in a fifth step into the final products (I) as described in scheme 2 (last step).

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly as modulators of γ-secretase.

BIOLOGICAL EXAMPLES

Screening for compounds which preferentially inhibit production of Aβ 42 vs. total Aβ was performed using H4 neuroglioma cells stably expressing the human APP695 isoform grown in Dulbecco's Modified Eagles medium (DMEM) GlutaMAX supplemented with 10% Fetal Bovine Serum and 250 µg/mL Zeocine. Cells were plated out to near confluency. The compounds to be tested were received as 10 mM stocks in 100% DMSO. A dilution series was initially generated in 100% DMSO and then diluted 200-fold in cell culture media such that the tested concentration range was 30 µM to 0.1 nM and the final DMSO concentration was 0.5%. The diluted compounds were incubated with the cells for 22 hours in an incubator at 37° C. and 5% $CO_2$. Aβ42 as well as Aβ total levels were then measured post-incubation from the supernatant of the cells. Aβ42 levels were determined using a specific electrochemiluminescence assay provided by Meso Scale Discovery (Catalog #L21CA-1) according to the manufacturer's protocol. Aβ total levels were likewise determined using a specific electrochemiluminescence assay provided by Meso Scale Discovery (Catalog #L21ZA-1) according to the manufacturer's protocol. To identify compounds which preferentially inhibited Aβ42, the ratio Aβ total $IC_{50}$/Aβ42 $IC_{50}$ was determined, where the higher the ratio, the more specific the inhibition of Aβ42 over Aβ total.

The compounds of general formula I according to the invention for example have $IC_{50}$ values below 30000 nM, particularly below 1000 nM, most preferably below 500 nM.

TABLE 3

Activity of the examples (Ex) compiled in the experimental part, based on Aβ$_{42}$ cellular $IC_{50}$ values in H4 neuroglioma cells (see above).

| Ex | $IC_{50}$ [µM] | Ratio Aβ(total)/ Aβ$_{42}$ | Ex | $IC_{50}$ [µM] | Ratio Aβ(total)/ Aβ$_{42}$ |
|---|---|---|---|---|---|
| 1 | 0.048 | 127 | 2 | 0.097 | 59 |
| 3 | 0.398 | 17 | 4 | 0.113 | 44 |
| 5 | 0.72 | 14 | 5-1 | 0.072 | 109 |
| 5-2 | 0.175 | 64 | 5-3 | 0.265 | 101 |
| 5-4 | 0.172 | >175 | 5-5 | 0.711 | 13 |
| 5-6 | 0.704 | 43 | 5-7 | 11.4 | 3 |
| 6 | 0.084 | 96 | 7 | 0.096 | 98 |
| 8 | 0.293 | 62 | 9 | 1.23 | >24 |
| 10 | 0.149 | 189 | 11 | 0.097 | >310 |
| 12 | 0.16 | 147 | 12-1 | 2.94 | >10 |
| 12-2 | 5.75 | >5 | 12-3 | 1.1 | >27 |
| 12-4 | 0.754 | >39 | 13 | 0.420 | 14 |
| 14 | 0.097 | 67 | 15 | 0.145 | 36 |
| 16 | 0.222 | 33 | 17 | 0.299 | 68 |
| 18 | 0.140 | 215 | 19 | 0.364 | 82 |
| 19-1 | 0.201 | 131 | 20 | 0.223 | 30 |
| 21 | 0.105 | 98 | 22 | 0.818 | 71 |
| 23 | 0.070 | 90 | 24 | 0.166 | 181 |
| 25 | 0.145 | 73 | 26 | 0.063 | 253 |
| 27 | 0.36 | 70 | 28 | 0.272 | 29 |
| 29 | 0.231 | 76 | 30 | 0.312 | 96 |
| 31 | 0.54 | 55 | 32 | 0.134 | 66 |
| 33 | 0.076 | 171 | 34 | 0.928 | 30 |
| 35 | 0.126 | 71 | 36 | 0.064 | 86 |
| 37 | 0.320 | 12 | | | |

Whereas γ-Secretase inhibitors simultaneously inhibit production of all Aβ species, γ-Secretase modulators preferentially inhibit the production of the neurotoxic Aβ42 species. In order to absolutely define the described compounds as modulators of γ-Secretase as opposed to simply inhibitors of γ-Secretase, measurements of not only Aβ42 but also Aβ total are performed. When the ratio of Aβ total $IC_{50}$/Aβ 42 $IC_{50}$ is >1, the compound preferentially inhibits Aβ42 production, thereby demonstrating that the compound is in fact a γ-Secretase modulator.

In view of their ability to modulate the activity of γ-secretase, the compounds of general formula I according to the invention are suitable for the treatment and/or preventative treatment of all those conditions or diseases which may be affected by the formation of Aβ peptides. Therefore, compounds according to the invention are particularly suitable for the prevention or treatment of diseases, particularly Down's syndrome, Abeta-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, dementia associated with Parkinson's disease, progressive supranuclear palsy or cortical basal degeneration, the dry form of age-related macular degeneration and glaucoma.

Preferably the compounds according to the invention, including the physiologically acceptable salts thereof, are suitable for the prevention or treatment of Alzheimer's Disease, the dry form of age-related macular degeneration and/or MCI.

In particular, the compounds according to the invention, including the physiologically acceptable salts thereof, are suitable for the prevention or treatment of Alzheimer's Disease and/or MCI.

In a further aspect of the present invention the present invention relates to methods for the treatment or prevention of above mentioned diseases and conditions, which method comprises the administration of an effective amount of a compound of general formula I to a human being.

The dose range of the compounds of general formula I applicable per day is usually from 0.1 to 1000 mg, preferably from 1 to 500 mg by oral route, in each case administered 1 to 4 times a day.

Each dosage unit may conveniently contain from 0.1 to 500 mg, preferably 1 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, BACE inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine); NMDA receptor antagonists (e.g. memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, glycine transporter 1 inhibitors, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt thereof combined with at least one of the active substances described above as a combination partner, for preparing a pharmaceutical composition which is suitable for the treatment or prevention of diseases or conditions which can be affected by modulation of γ-secretase. These are preferably Aβ-related pathologies, particularly one of the diseases or conditions listed above, most particularly Alzheimer's Disease and/or MCI.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

Examples

The following examples are intended to illustrate the invention, without restricting its scope.

As a rule, melting points, IR, $^1$H-NMR and/or mass spectra have been obtained for the compounds prepared. Unless otherwise stated, Rf values were obtained using ready-made silica gel 60 F254 TLC plates (E. Merck, Darmstadt, item no. 1.05714) without chamber saturation. The ratios given for the eluents refer to units by volume of the solvents in question. Chromatographic purification was done using silica gel supplied by E. Merck, Darmstadt (Silica gel 60, 0.040-0.063 mm, item no. 1.09385.2500).

The following abbreviations are used in the examples:
CH Cyclohexane
DAD Diode array detection
DCM Dichloromethane
DIPEA N-Ethyl-diisopropylamine
DMA N,N-Dimethylacetamide
DMSO Dimethylsulphoxide
DMF N,N-Dimethylformamide
EA Ethyl acetate
ESI Electrospray ionisation
Exp. Example
h Hour(s)
HPLC High performance liquid chromatography
M Molar
MeOH Methanol
min Minute(s)
mL Milliliters
µL Microliters
mmol Millimoles
µmol Micromoles
MPLC Medium pressure liquid chromatography
MS Mass spectrometry
NMP N-Methyl-pyrrolidinone
PE Petroleum ether
Rf Retention factor
Rt Retention time
sat. saturated
tert. tertiary
TFA Trifluoroacetic acid
THF Tetrahydrofurane
UPLC Ultra performance liquid chromatography All references to brine refer to a saturated aqueous solution of sodium chloride. Unless otherwise indicated, all temperatures are expressed in ° C. (degrees Centigrade). All reactions are conducted without the application of inert atmosphere at room temperature unless otherwise noted.

HPLC/UPLC Methods:
Method A:

Device:
Waters Acquity with DAD and ESI-MS detector
Column:
Waters XBridge C18, 2.1 × 20 mm, 2.5 µm -continued

| Time [min] | % Solvent A [H$_2$O, 0.10% TFA] | % Solvent B [MeOH] | Flow rate [mL/min] | Temperature [° C.] |
|---|---|---|---|---|
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

Method B:

Device:
Waters Acquity with DAD and ESI-MS detector
Column:
Waters Sunfire C18, 2.1 × 20 mm, 2.5 μm

| Time [min] | % Solvent A [H$_2$O, 0.10% TFA] | % Solvent B [MeOH] | Flow rate [mL/min] | Temperature [° C.] |
|---|---|---|---|---|
| 0.00 | 99 | 1 | 1.3 | 60 |
| 0.15 | 99 | 1 | 1.3 | 60 |
| 1.10 | 0 | 100 | 1.3 | 60 |
| 1.25 | 0 | 100 | 1.3 | 60 |

Method C:

Device:
Waters Alliance with DAD and ESI-MS detector
Column:
Waters SunFire C18, 4.6 × 30 mm, 3.5 μm

| Time [min] | % Solvent A [H$_2$O, 0.10% TFA] | % Solvent B [MeOH] | Flow rate [mL/min] | Temperature [° C.] |
|---|---|---|---|---|
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

Method D

Device:
Waters Alliance with DAD and ESI-MS detector
Column:
Waters XBridge C18, 4.6 × 30 mm, 3.5 μm

| Time [min] | % Solvent A [H$_2$O, 0.10% NH$_3$] | % Solvent B [MeOH] | Flow rate [mL/min] | Temperature [° C.] |
|---|---|---|---|---|
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

Method E:

Device:
Agilent 1200 with DA and MS detector
Column:
XBridge C18, 3 × 30 mm, 2.5 μm

| Time [min] | % Solvent A [H$_2$O, 0.10% NH$_3$] | % Solvent B [acetonitrile] | Flow rate [mL/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method F:

Device:
Agilent 1200 with DA- and MS-Detector
Column:
Sunfire C18, 3 × 30 mm, 2.5 μm

| Time [min] | % Solvent A [H$_2$O, 0.10% TFA] | % Solvent B [Methanol] | Flow rate [mL/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method G:

Device:
Agilent 1200 with DA and MS detector
Column:
XBridge C18, 3 × 30 mm, 2.5 μm

| Time [min] | % Solvent A [H$_2$O, 0.10% TFA] | % Solvent B [Methanol] | Flow rate [mL/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method H:

Device:
Agilent 1200 with DA- and MS-Detector
Column:
XBridge C18, 3 × 30 mm, 2.5 μm

| Time [min] | % Solvent A [H$_2$O, 0.10% NH$_3$] | % Solvent B [Methanol] | Flow rate [mL/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method I:

Device:
Waters Alliance with DA- and MS-Detector
Column:
Xbridge C18, 4.6 × 30 mm, 3.5 μm

| Time [min] | % Solvent A [H$_2$O, 0.10% TFA] | % Solvent B [Methanol] | Flow rate [mL/min] | Temperature [° C.] |
|---|---|---|---|---|
| 0.0 | 50 | 50 | 4 | 60 |
| 1.6 | 0 | 100 | 4 | 60 |
| 1.85 | 0 | 100 | 4 | 60 |
| 1.9 | 95 | 5 | 4 | 60 |

Method J:

| Device: Waters Alliance with DA- and MS-Detector Column: Sunfire C18, 4.6 × 30 mm, 3.5 µm | | | | |
|---|---|---|---|---|
| Time [min] | % Solvent A [H₂O, 0.10% TFA] | % Solvent B [Acetonitrile] | Flow rate [mL/min] | Temperature [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Microwave Heating:

Biotage Initiator Sixty.

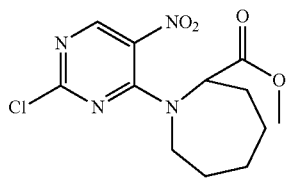 [SMILES: COC(=O)C1CCCCCN1c1nc(Cl)ncc1[N+](=O)[O-]]

Intermediate 1a

Hexahydro-1H-azepine-2-carboxylic acid methyl ester hydrochloride (1.30 g, 6.69 mmol) is mixed with 60 mL water. At 0° C. a solution of 2,4-dichloro-5-nitro-pyrimidine (1.30 g, 6.69 mmol) in diethyl-ether (60 mL) is added. Potassium hydrogen carbonate (1.42 g, 14.0 mmol) is added in portions. The reaction mixture is heated to room temperature and stirred for 48 h. The phases are separated and the aqueous phase is extracted with diethyl-ether. The organic phases are combined, dried and concentrated in vacuo to give the product that is used for the next step without further purification.

MS (ESI⁺): m/z=315/317 (Cl) [M+H]⁺

HPLC (Method A): Rt=0.754 min.

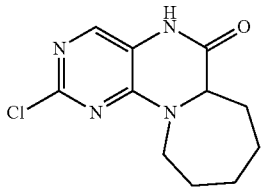 [SMILES: O=C1Nc2cnc(Cl)nc2N2CCCCCC12]

Intermediate 2a

Intermediate 1a (2.50 g, 5.96 mmol) is mixed with acetic acid (65 mL). At 80° C. Iron powder (2.95 g, 52.9 mmol) is added in portions. After stirring for 0.5 h the hot reaction mixture is filtered and the filtrate is concentrated in vacuo. Water is added to the residue and the mixture is extracted with DCM. The aqueous phase is adjusted to an alkaline pH with conc. ammonia (30 mL). The precipitate is filtered off and the aqueous phase is extracted with DCM. The organic phases and the precipitate are combined and purified by column chromatography (silica, DCM/MeOH 98/2->95/5) to yield the product.

MS (ESI⁺): m/z=253/255 (Cl) [M+H]⁺

HPLC (Method A): Rt=0.631 min.

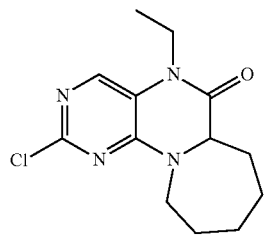 [SMILES: CCN1C(=O)C2CCCCCN2c2nc(Cl)ncc21]

Intermediate 3a

Intermediate 2a (252.7 mg, 1.00 mmol) is mixed under argon with NMP (1 mL) and acetonitrile (3 mL). At 0° C. Iodo-ethane (105 µL, 1.30 mmol) and sodium hydride (44.0 mg, 1.10 mmol, 60% in mineral oil) are added and the reaction mixture is stirred for 48 h. MeOH is added and the mixture is acidified with TFA and purified by preparative HPLC (eluent A: water+0.13% TFA, eluent B: MeOH) to give the product.

MS (ESI⁺): m/z=281/283 (Cl) [M+H]⁺

HPLC (Method A): Rt=0.710 min.

In analogy to the preparation of intermediate 3a the following intermediates are obtained:

| Nr. | Structure | Educt | Mass signal(s) | R_t |
|---|---|---|---|---|
| 3b | 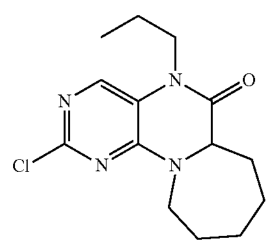 [SMILES: CCCN1C(=O)C2CCCCCN2c2nc(Cl)ncc21] | 1-iodo-propane | (M + H)⁺ = 295/297 (Cl) | 0.760 min. (method A) |
| 3c | 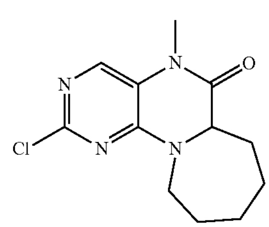 [SMILES: CN1C(=O)C2CCCCCN2c2nc(Cl)ncc21] | methyl iodide | (M + H)⁺ = 267/269 (Cl) | 0.665 min. (method A) |
| 3d | 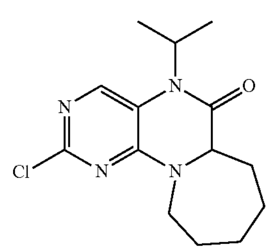 [SMILES: CC(C)N1C(=O)C2CCCCCN2c2nc(Cl)ncc21] | 2-iodo-propane | (M + H)⁺ = 295 | 1.36 min. (method B) |

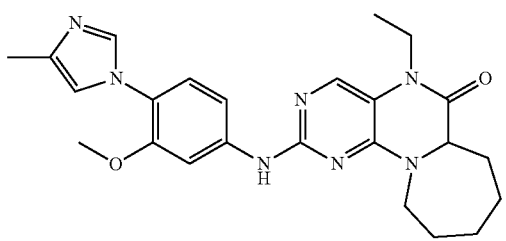 [SMILES: CCN1C(=O)C2CCCCCN2c2nc(Nc3ccc(-n4cnc(C)c4)c(OC)c3)ncc21]

Example 1

Intermediate 3a (95.0 mg, 0.241 mmol), 3-methoxy-4-(4-methyl-imidazol-1-yl)-phenylamine (48.9 mg, 0.241 mmol), p-toluenesulfonic acid (12% in acetic acid, 0.775 mL, 0.578 mmol) and 4-methyl-2-pentanol (1.34 mL, 10.4 mmol) are mixed and heated for 1.5 h to 145° C. using a microwave oven. The reaction mixture is poured into ice water, adjusted to an alkaline pH with aqueous sodium hydroxide solution and extracted with EA. The organic phase is dried and concentrated in vacuo. The residue is purified by preparative HPLC (eluent A: water+0.1% $NH_3$, eluent B: MeOH) to yield the product.

MS (ESI$^+$): m/z=448 [M+H]$^+$

HPLC (Method A): Rt=0.522 min.

In analogy to the preparation of example 1 the following examples are obtained:

| Exp. | Structure | Educt 1 | Educt 2 | Mass signal(s) | $R_t$ |
|---|---|---|---|---|---|
| 2 | 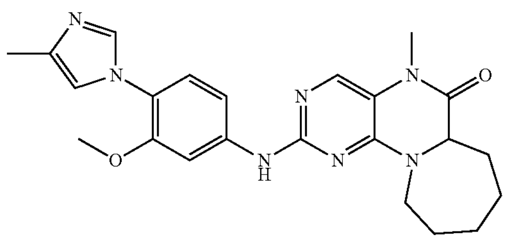 [SMILES: COc1cc(Nc2ncc3c(n2)N2CCCCCC2C(=O)N3C)ccc1-n1cnc(C)c1] | Intermediate 3c | | (M + H)$^+$ = 434 | 0.488 (method A) |
| 3 | 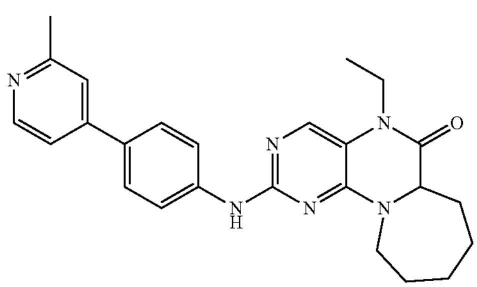 [SMILES: CCN1C(=O)C2CCCCCN2c2nc(Nc3ccc(-c4ccnc(C)c4)cc3)ncc21] | Intermediate 3a | | (M + H)$^+$ = 429 | 0.510 min (method A) |
| | | (see WO 09-075874) | | | |
| 4 | 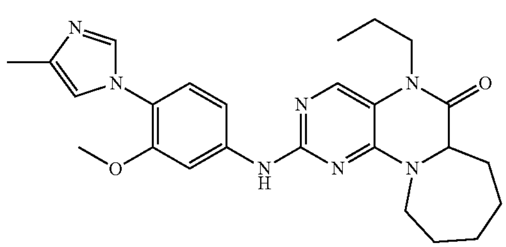 [SMILES: CCCN1C(=O)C2CCCCCN2c2nc(Nc3ccc(-n4cnc(C)c4)c(OC)c3)ncc21] | Intermediate 3b | | (M + H)$^+$ = 462 | 0.545 (method A) |

-continued

| Exp. | Structure | Educt 1 | Educt 2 | Mass signal(s) | $R_t$ |
|---|---|---|---|---|---|
| 5 | 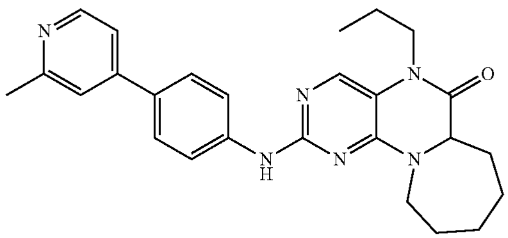 [SMILES: CCCN1C(=O)C2CCCCCN2c2nc(Nc3ccc(-c4ccnc(C)c4)cc3)ncc21] | Intermediate 3b | | $(M + H)^+ = 443$ | 0.552 min (method A) |

In analogy to the preparation of example 9 the following examples are obtained:

| Exp. | Structure | Educt 1 | Educt 2 | Mass signal(s) | $R_t$ |
|---|---|---|---|---|---|
| 5-1 | 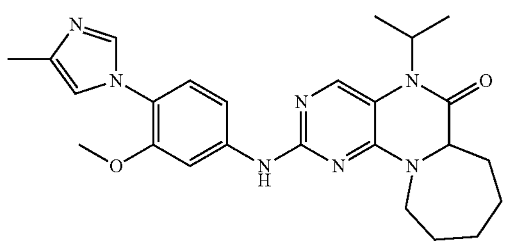 [SMILES: COc1cc(Nc2ncc3c(n2)N2CCCCCC2C(=O)N3C(C)C)ccc1-n1cnc(C)c1] | Intermediate 3d | | $(M + H)^+ = 462$ | 0.97 (method C) |
| 5-2 | 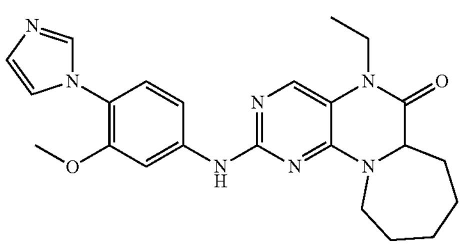 [SMILES: CCN1C(=O)C2CCCCCN2c2nc(Nc3ccc(-n4ccnc4)c(OC)c3)ncc21] | Intermediate 3a | | $(M + H)^+ = 434$ | 0.85 (method C) |
| 5-3 | 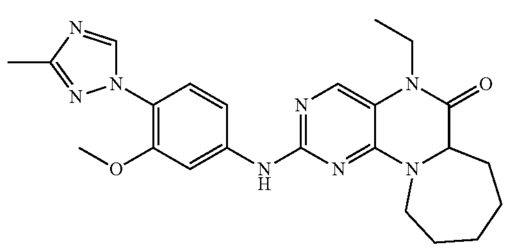 [SMILES: CCN1C(=O)C2CCCCCN2c2nc(Nc3ccc(-n4cnc(C)n4)c(OC)c3)ncc21] | Intermediate 3a | (prepared according to WO 2011/014535) | $(M + H)^+ = 449$ | 1.08 (method C) |

-continued

| Exp. | Structure | Educt 1 | Educt 2 | Mass signal(s) | $R_t$ |
|---|---|---|---|---|---|
| 5-4 | 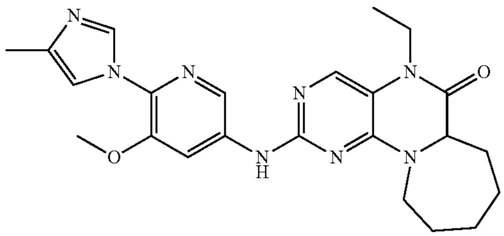 [SMILES: CCN1C(=O)C2CCCCCN2c2nc(Nc3cnc(-n4cnc(C)c4)c(OC)c3)ncc21] | Intermediate 3a | | | |
| 5-5 | 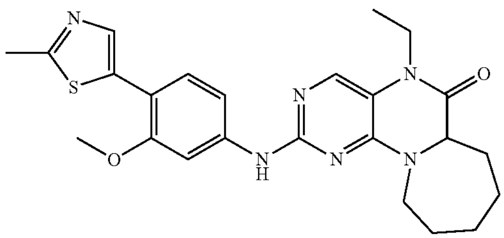 [SMILES: CCN1C(=O)C2CCCCCN2c2nc(Nc3ccc(-c4cnc(C)s4)c(OC)c3)ncc21] | Intermediate 3a | (see Luebbers, T. et al., Bioorg. Med. Chem. Lett. 2011, 21(21), 6554) | $(M + H)^+ =$ 465 | 0.76 (method B) |
| 5-6 | 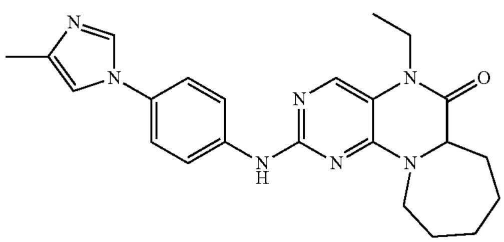 [SMILES: CCN1C(=O)C2CCCCCN2c2nc(Nc3ccc(-n4cnc(C)c4)cc3)ncc21] | Intermediate 3a | | $(M + H)^+ =$ 418 | 0.57 (method B) |
| 5-7 | 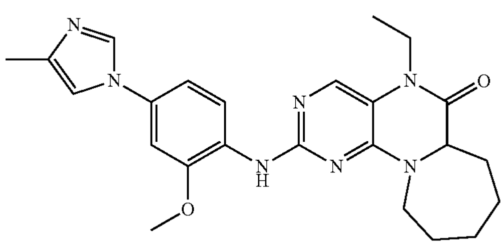 [SMILES: CCN1C(=O)C2CCCCCN2c2nc(Nc3ccc(-n4cnc(C)c4)cc3OC)ncc21] | Intermediate 3a | Intermediate 66a | $(M + H)^+ =$ 448 | |
| 5-8 | 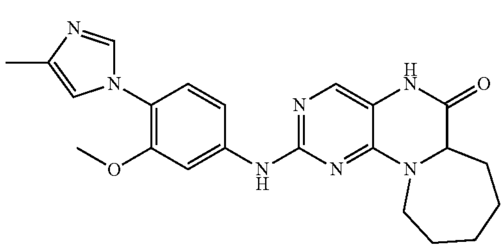 [SMILES: COc1cc(Nc2ncc3c(n2)N2CCCCCC2C(=O)N3)ccc1-n1cnc(C)c1] | Intermediate 2a | | $(M + H)^+ =$ 420 | 0.83 (method C) |

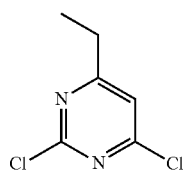

Intermediate 4a 2,4,6-trichloropyrimidine (14.0 mL, 116 mmol) and copper (I) iodide (2.21 g, 11.6 mmol) are mixed under argon with THF (200 mL). At 0° C. ethylmagnesium bromide (116 mL, 116 mmol, 1M in THF) is added slowly and the reaction mixture is stirred for 2 h at 0° C., heated to room temperature and stirred for further 12 h. The reaction mixture is quenched with sat. ammonium chloride solution and extracted with tert.-butylmethyl-ether. The organic phase is dried and concentrated in vacuo. The product is obtained after purification by column chromatography (silica, CH/EA 97:3).

MS (ESI$^+$): m/z=177/179/181 (2Cl) [M+H]$^+$

HPLC (Method B): Rt=1.15 min.

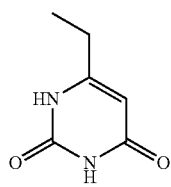

Intermediate 5a

Intermediate 4a (19.22 g, 108.6 mmol) is mixed with HCl (75.0 mL, 32% in water) and heated to reflux for 2 h. The reaction mixture is concentrated in vacuo and freeze dried to yield the product that is used for the next step without further purification.

MS (ESI$^+$): m/Z=141 [M+H]$^+$

HPLC (Method B): Rt=0.38 min

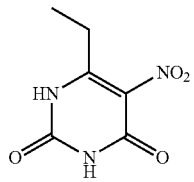

Intermediate 6a

Intermediate 5a (14.5 g, 103 mmol) is mixed with concentrated sulphuric acid (150 mL) at 0° C. Nitric acid (9.88 mL, 155 mmol; 65% in water) is added slowly and the reaction mixture is stirred for 1 h at 0° C. and for 12 h at room temperature. The reaction mixture is poured on ice and stirred for 2 h. The precipitate is filtered off and washed with water to yield the product that is used for the next step without further purification.

MS (ESI$^+$): m/z=186 [M+H]$^+$

HPLC (Method B): Rt=0.52 min.

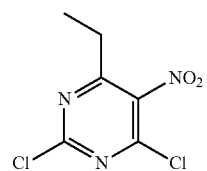

Intermediate 7a

Phosphorus oxychloride (50 mL) is mixed with N,N-diethylaniline (12.8 mL, 81 mmol). Intermediate 6a (11.5 g, 62.1 mmol) is added at room temperature and stirred for 20 min, followed by heating to reflux for 2 h. After cooling to room temperature the reaction mixture is poured into ice water. The precipitate is filtered off and purified by column chromatography (silica, DCM/MeOH 99:1) to yield the product.

MS (ESI$^-$): m/z=220/222/224 (2Cl) [M−H]$^-$

HPLC (Method B): Rt=1.43 min.

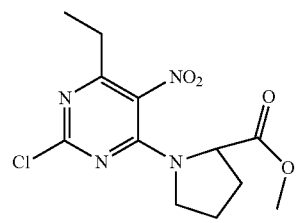 [SMILES: CCc1nc(Cl)nc(N2CCCC2C(=O)OC)c1[N+](=O)[O-]]

Intermediate 8a

Intermediate 8a is prepared in analogy to the preparation of intermediate 1a using intermediate 7a and pyrrolidine-2-carboxylic acid methyl ester.

MS (ESI$^+$): m/z=315/317 (Cl) [M+H]$^+$

HPLC (Method C): Rt=1.40. min.

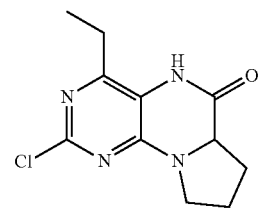 [SMILES: CCc1nc(Cl)nc2c1NC(=O)C1CCCN21]

Intermediate 9a

Intermediate 9a is prepared in analogy to the preparation of intermediate 2a using intermediate 8a.

MS (ESI$^+$): m/z=253/255 (Cl) [M+H]$^+$

HPLC (Method C): Rt=0.98 min.

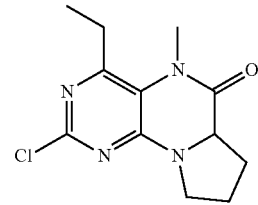 [SMILES: CCc1nc(Cl)nc2c1N(C)C(=O)C1CCCN21]

Intermediate 10a

Intermediate 10a is prepared in analogy to the preparation of intermediate 3a using intermediate 9a and methyl iodide.

MS (ESI$^+$): m/z=267/269 (Cl) [M+H]$^+$

HPLC (Method C): Rt=1.07 min.

In analogy to the preparation of example 1 the following examples are obtained:

| Exp. | Structure | Educt 1 | Educt 2 | Mass signal(s) | $R_t$ |
|---|---|---|---|---|---|
| 6 | 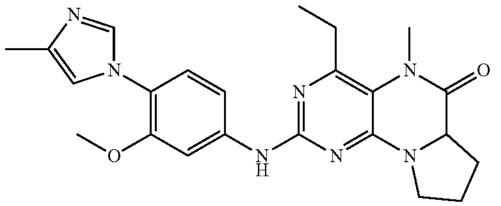 [SMILES: CCc1nc(Nc2ccc(-n3cnc(C)c3)c(OC)c2)nc2c1N(C)C(=O)C1CCCN21] | Intermediate 10a | | $(M+H)^+ = 434$ | 0.84 min (method B) |
| 7 | 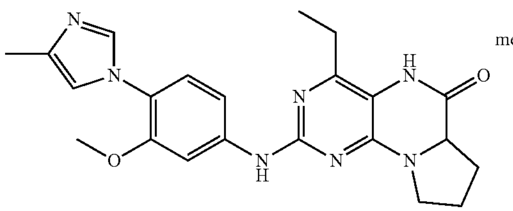 | Intermediate 9a | | $(M+H)^+ = 420$ | 0.83 min (method B) |
| 8 | 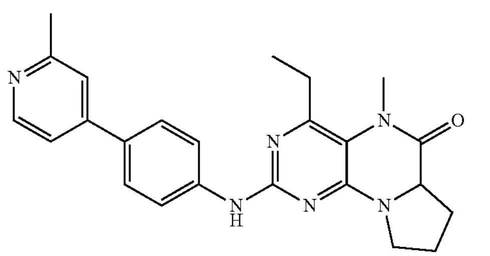 [SMILES: CCc1nc(Nc2ccc(-c3ccnc(C)c3)cc2)nc2c1N(C)C(=O)C1CCCN21] | Intermediate 10a | | $(M+H)^+ = 415$ | 0.85 min (method B) |

Example 9

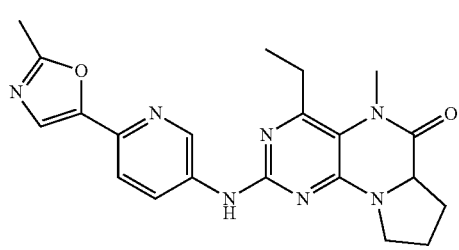 [SMILES: CCc1nc(Nc2ccc(-c3cnc(C)o3)nc2)nc2c1N(C)C(=O)C1CCCN21]

Intermediate 10a (60.0 mg, 0.225 mmol), 6-(2-methyl-oxazol-5-yl)-pyridin-3-ylamine (51.2 mg, 0.292 mmol, prepared according to WO 2010/089292), caesium carbonate (52.3 mg, 0.405 mmol), palladium acetate (5.05 mg, 0.022 mmol), xantphos (26.0 mg, 0.045 mmol) and dioxane (2.0 mL) are mixed and stirred for 12 h at 120° C. The reaction mixture is acidified with TFA, diluted with DMSO and filtered off. The residue is purified by preparative HPLC (eluent A: water+0.13% TFA, eluent B: MeOH) to give the product as a TFA salt.

MS (ESI⁻): m/z=404 [M−H]⁻
HPLC (Method A): Rt=0.527 min.

In analogy to the preparation of example 9 the following example is obtained as TFA salt:

| Exp. | Structure | Educt 1 | Educt 2 | Mass signal(s) | $R_t$ |
|---|---|---|---|---|---|
| 10 | 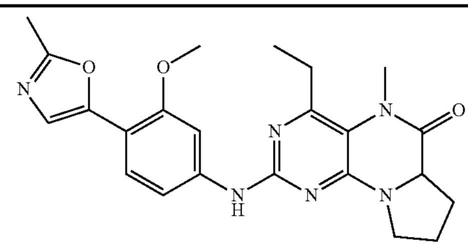 | Intermediate 10a | (see Iwanowicz, E.J. et al., Bioorg. & Med. Chem. Lett. 2003, 13(12), 2059) | $(M + H)^+ =$ 435 | 0.611 min (method A) |

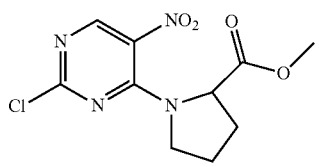 [SMILES: COC(=O)C1CCCN1c1nc(Cl)ncc1[N+](=O)[O-]]

Intermediate 11a

Pyrrolidine-2-carboxylic acid methyl ester hydrochloride (25 g, 151 mmol), 2,4-dichloro-5-nitro-pyrimidine (31.3 g, 162 mmol) and potassium carbonate (49.1 g, 355 mmol) are mixed with 270 mL acetone. At 0° C. water (27 mL) is added slowly. After 1 h at 0° C. the reaction mixture is heated to room temperature and stirred for 2 h. The mixture is concentrated in vacuo. Water is added and the mixture is extracted with EA twice. The organic phases are combined, dried over sodium sulfate, filtered and concentrated in vacuo to give the product that is used for the next step without further purification.

Rf (EA/CH 1:3)=0.5

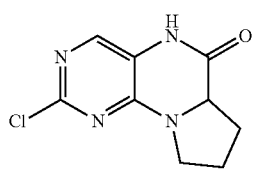 [SMILES: O=C1Nc2cnc(Cl)nc2N2CCCC12]

Intermediate 12a

Intermediate 12a is prepared in analogy to the preparation of intermediate 2a using intermediate 11a.

Rf (DCM/MeOH 9:1)=0.4

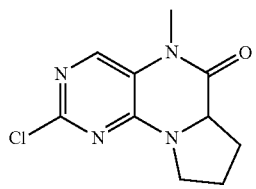 [SMILES: CN1C(=O)C2CCCN2c2nc(Cl)ncc21]

Intermediate 13a

Intermediate 12a (250 mg, 1.12 mmol) is dissolved in DMF at 0° C. and potassium carbonate (308 mg, 2.23 mmol) is added. Methyl iodide (111 μL, 1.78 mmol) is added. After 5 min. the reaction mixture is heated to room temperature and stirred for 12 h. A second portion of methyl iodide (34.6 μL, 0.556 mmol) is added and the reaction mixture is stirred for another 2.5 h. EA is added and the mixture is neutralised with 1M HCl, washed with water and brine. The organic phase is concentrated in vacuo to give the product as a solid.

MS (ESI$^+$): m/z=239/241 [M+H]$^+$

HPLC (Method A): Rt=0.53 min

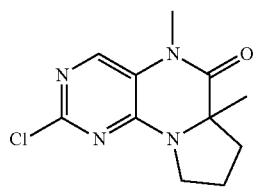 [SMILES: CN1C(=O)C2(C)CCCN2c2nc(Cl)ncc21]

Intermediate 14a

Intermediate 13a (145 mg, 0.608 mmol) is added at −78° C. to a solution of lithium diisopropyl amide (0.759 mL, 2.0 M in THF/heptane/ethylbenzene, 1.52 mmol) in anhydrous THF (8 mL). The reaction mixture is stirred for 25 min. and a solution of methyl iodide (83.2 μL, 1.34 mmol) in THF (6 mL) is added. The mixture is stirred for 25 min. at −78° C., for 1 h at −50° C., for 4.5 h at 0° C. and for 1.5 h at room temperature. The mixture is quenched with sat. aqueous ammonium chloride solution and evaporated to dryness. DCM is added to the residue and the mixture is washed with sat. aqueous sodium carbonate solution. The organic phase is concentrated in vacuo and purified by preparative HPLC (eluent A: water+0.1% NH$_3$, eluent B: MeOH) to give the product.

MS (ESI$^+$): m/z=253/255 (Cl) [M+H]$^+$

HPLC (Method B): Rt=0.64 min

In analogy to the preparation of example 1 the following examples are obtained:

| Exp. | Structure | Educt | | Mass signal(s) | R$_t$ |
|---|---|---|---|---|---|
| 11 | 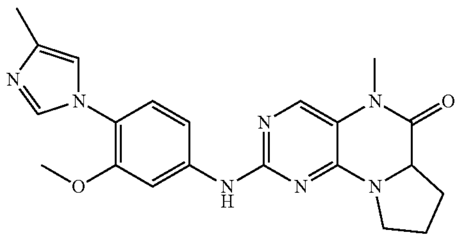 [SMILES: COc1cc(Nc2ncc3c(n2)N2CCCC2C(=O)N3C)ccc1-n1cnc(C)c1] | Intermediate 13a | NH$_2$ structure | (M + H)$^+$ = 406 | 0.46 min (method A) |
| 12 | 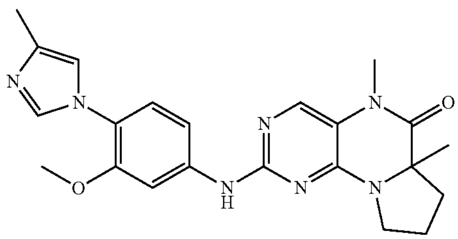 [SMILES: COc1cc(Nc2ncc3c(n2)N2CCCC2(C)C(=O)N3C)ccc1-n1cnc(C)c1] | Intermediate 14a | NH$_2$ structure | (M + H)$^+$ = 420 | 0.54 min (method B) |

In analogy to the preparation of example 9 the following examples are obtained:

| Exp. | Structure | Educt | | Mass signal(s) | R$_t$ |
|---|---|---|---|---|---|
| 12-1 | 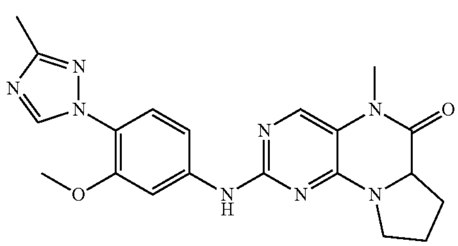 [SMILES: COc1cc(Nc2ncc3c(n2)N2CCCC2C(=O)N3C)ccc1-n1cnc(C)n1] | Intermediate 13a | NH$_2$ structure | (M + H)$^+$ = 407 | 1.25 min (method D) |
| 12-2 | 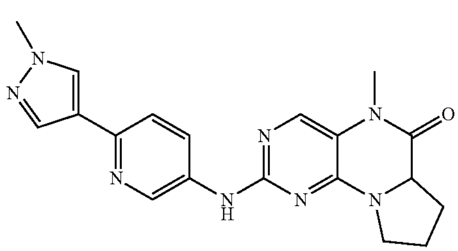 [SMILES: CN1C(=O)C2CCCN2c2nc(Nc3ccc(-c4cnn(C)c4)nc3)ncc21] | Intermediate 14a | NH$_2$ structure (prepared according to WO 2010/089292) | (M + H)$^+$ = 377 | 1.19 min (method D) |

-continued

| Exp. | Structure | Educt | Mass signal(s) | $R_t$ |
|---|---|---|---|---|
| 12-3 | 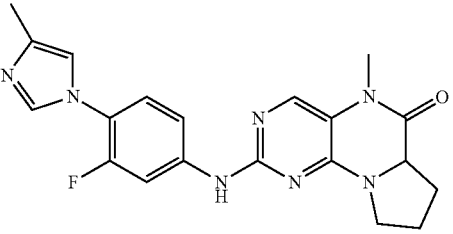 | Intermediate 14a | 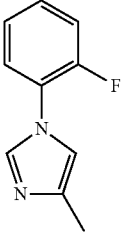 | $(M + H)^+ =$ 394 | 1.27 min (method D) |
| 12-4 | 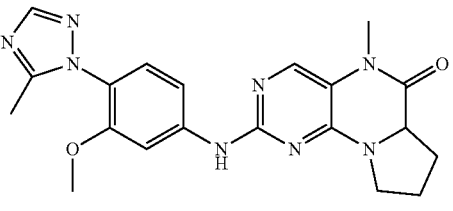 [SMILES: COc1cc(Nc2ncc3c(n2)N2CCCC2C(=O)N3C)ccc1-n1ncnc1C] | Intermediate 14a | 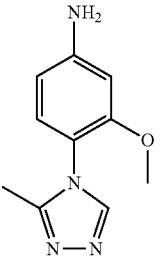 (prepared in analogy to WO 2010/094647) | $(M + H)^+ =$ 407 | 1.10 min (method D) |

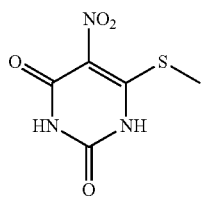

Intermediate 15a

6-Chloro-5-nitro-1H-pyrimidine-2,4-dione (25.6 g, 134 mmol) is mixed with THF (300 mL) and cooled to 0° C. Sodium thiomethylate (25.0 g, 357 mmol) is added in portions (temperature<5° C.). The reaction mixture is stirred for 16 h, poured into hydrochloric acid (1 M in $H_2O$; 1000 mL) at 0° C. and stirred for 1 h. The precipitate is filtered off, washed with ice-water and EA and dried to yield the product that is taken to the next step without further purification.

Rf (EA/MeOH 8:2)=0.28

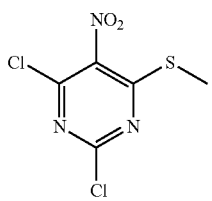

Intermediate 16a

Phosphorous oxychloride (600 mL) is cooled to 0° C. under nitrogen. DIPEA (25.4 mL, 154 mmol) is added. Intermediate 15a (15.6 g, 76.8 mmol) is added slowly and the reaction mixture is suspended using an ultrasound bath. DIPEA (19.6 mL, 119 mmol) is added carefully at 0° C. The reaction mixture is stirred for 1 h at 0-5° C. and it is allowed to reach room temperature. The reaction mixture is concentrated in vacuo to 200 mL and poured into ice-water (1 L). The residue is extracted with diethyl ether. The organic phase is dried and concentrated in vacuo. The residue is taken up in DCM, magnesium sulfate is added, filtered over silica gel and washed with DCM. The DCM phases are concentrated in vacuo to yield the product, that is used for the next reaction without further purification.

Rf (CH/DCM 2:1)=0.48

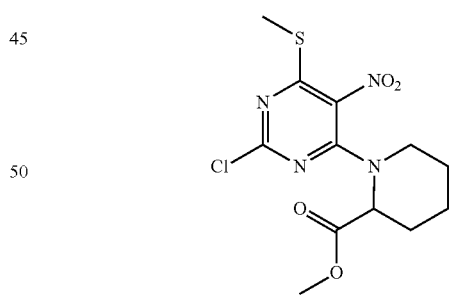

Intermediate 17a

Intermediate 16a (1.00 g, 4.165 mmol) is mixed with DCM (60 mL) under nitrogen. The reaction mixture is cooled to −70° C. and a mixture of piperidine-2-carboxylic acid methyl ester hydrochloride (0.760 g, 4.23 mmol) and DIPEA (0.712 mL, 4.16 mmol) in DCM (20 mL) is added slowly. The reaction mixture is allowed to reach room temperature slowly followed by addition of aqueous potassium hydrogensulfate solution (80 mL) and stirring for 15 min. The phases are separated and the organic phase is concentrated in vacuo to give the product as an oil that is used for the next step without further purification.

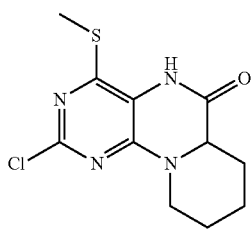

Intermediate 18a

Intermediate 17a (1.40 g, 4.00 mmol) is mixed with acetic acid (20 mL) and heated to 80° C. Iron powder (0.50 g, 8.95 mmol) is added in portions. The reaction mixture is stirred for 1 h and filtered over celite and activated carbon and washed with acetic acid and EA. The filtrate is concentrated in vacuo and MeOH is added to the residue. The formed precipitate is filtered off and washed consecutively with MeOH, EA and tert.-butylmethyl-ether. The product is obtained after drying in vacuo as a solid and taken to the next step without further purification.

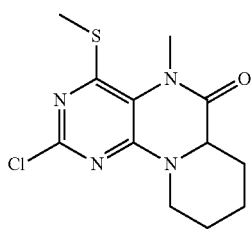 [SMILES: CSc1nc(Cl)nc2c1N(C)C(=O)C1CCCCN21]

Intermediate 19a

Intermediate 18a (0.20 g, 0.702 mmol) is mixed with DMA (2 mL) and sodium hydride (60% in mineral oil, 0.028 g, 0.700 mmol) and stirred for 10 min. The reaction mixture is cooled to 0° C. and methyl iodide (0.044 mL, 0.701 mmol) is added. The reaction mixture is stirred for 1.5 h at 0° C. Water is added and the precipitate is filtered off and washed with PE. The product is obtained after drying in vacuo as a solid and taken to the next step without further purification.

MS (ESI$^+$): m/z=299/301 (Cl) [M+H]$^+$
HPLC (Method C): Rt=1.51 Min

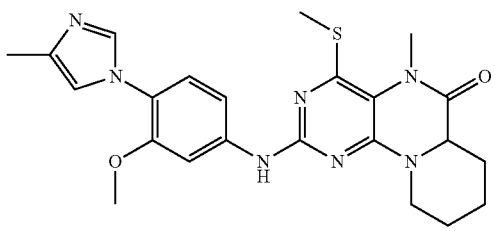 [SMILES: COc1cc(Nc2nc(SC)c3c(n2)N2CCCCC2C(=O)N3C)ccc1-n1cnc(C)c1]

Example 13

Intermediate 19a (40.0 mg, 0.134 mmol) and 3-methoxy-4-(4-methyl-1H-imidazol-1-yl)aniline (40.8 mg, 0.201 mmol) are mixed with dioxane (1 mL) and nitrogen gas is bubbled through the mixture for 5 min. (2-Dicyclohexylphosphino-2',4',6'-thisopropyl-1,1'-biphenyl)[2-(2-aminoethyl)phenyl]palladium(11) chloride (10.0 mg, 0.014 mmol, CAS-number: 1028206-56-5) is added and caesium carbonate (129 mg, 0.396 mmol) is added and the reaction mixture is heated to 145° C. for 2 h using a microwave oven. The reaction mixture is filtered through celite and washed with DCM. The filtrate is concentrated in vacuo and the residue is purified by preparative HPLC (eluent A: water+0.13% TFA, eluent B: MeOH) to give the product as a TFA salt. The free base of the product is obtained as a solid after liquid/liquid extraction using DCM and aqueous sodium carbonate.

MS (ESI$^+$): m/z=466 [M+H]$^+$
HPLC (Method B): Rt=0.76 Min

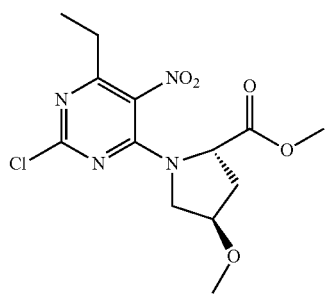 [SMILES: CCc1nc(Cl)nc(N2C[C@H](OC)C[C@H]2C(=O)OC)c1[N+](=O)[O-]]

Intermediate 20a

Intermediate 20a is prepared in analogy to the preparation of intermediate 1a using intermediate 7a and (2S,4R)-4-methoxypyrrolidine-2-carboxylic acid methyl ester.

MS (ESI$^+$): m/z=345/347 (Cl) [M+H]$^+$
HPLC (Method C): Rt=1.41 min.

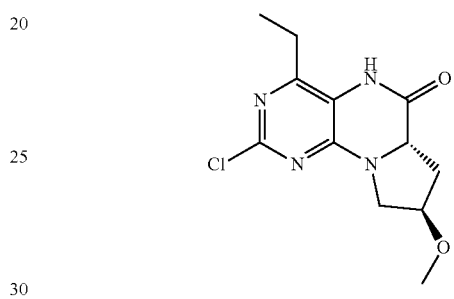

Intermediate 21a

Intermediate 21a is prepared in analogy to the preparation of intermediate 2a using intermediate 20a.

MS (ESI$^+$): m/z=283/285 (Cl) [M+H]$^+$
HPLC (Method C): Rt=1.03 min.

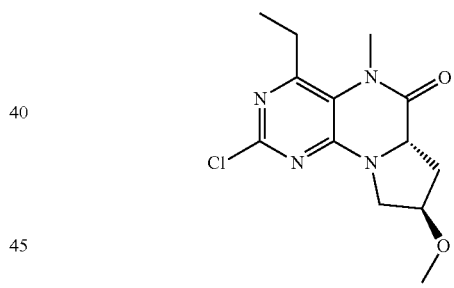

Intermediate 22a

Intermediate 22a is prepared in analogy to the preparation of intermediate 3a using intermediate 21a and methyl iodide.

MS (ESI$^+$): m/z=297/299 (Cl) [M+H]$^+$
HPLC (Method B): Rt=0.69 min.

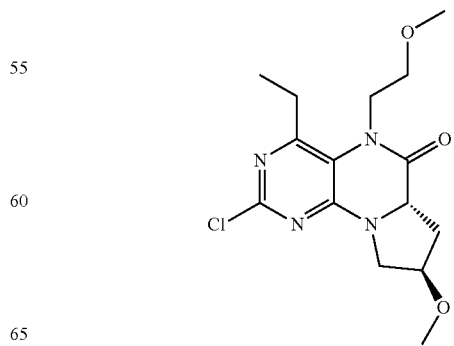

Intermediate 22a-1

Intermediate 22a-1 is prepared in analogy to the preparation of intermediate 3a using intermediate 21a and 2-bromo-ethyl-methylether.

MS (ESI⁺): m/z=341/343 (Cl) [M+H]⁺
HPLC (Method C): Rt=0.76 min.

In analogy to the preparation of example 9 the following examples are obtained:

| Exp. | Structure | Educt | Mass signal(s) | R_t |
|---|---|---|---|---|
| 14 | 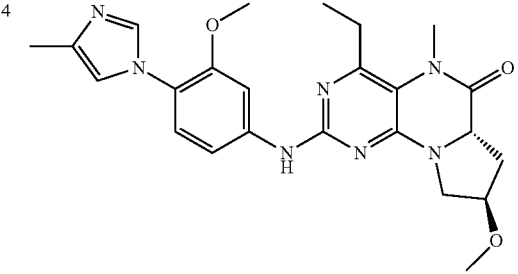 | Intermediate 21a | (M + H)⁺ = 464 | 1.42 min (method D) |
| 15 | 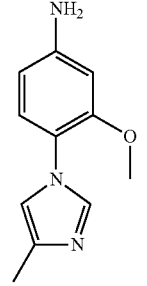 | Intermediate 21a | (M + H)⁺ = 459 | 1.31 min (method D) |
| 16 | 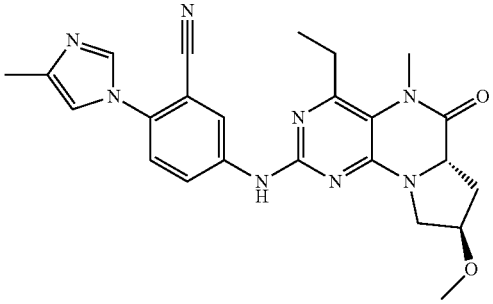 (see WO2011092272) | Intermediate 20a | (M + H)⁺ = 445 | 1.24 min (method D) |
| 17 | 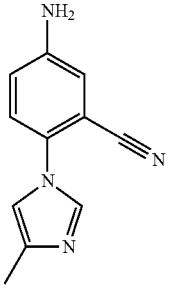 | Intermediate 20a | (M + H)⁺ = 450 | 1.29 min (method D) |

| Exp. | Structure | Educt | Mass signal(s) | $R_t$ |
|---|---|---|---|---|
| 18 | 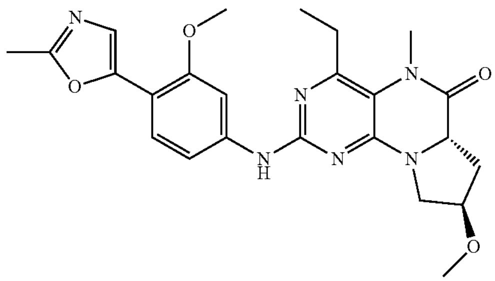 [SMILES: CCc1nc(Nc2ccc(-c3cnc(C)o3)c(OC)c2)nc2c1N(C)C(=O)[C@@H]1C[C@@H](OC)CN21] | Intermediate 21a | $(M + H)^+$ = 465 | 1.38 min (method D) |
| 19 | 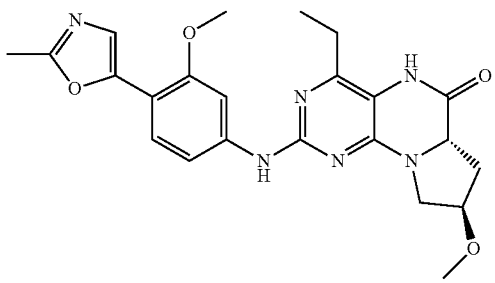 [SMILES: CCc1nc(Nc2ccc(-c3cnc(C)o3)c(OC)c2)nc2c1NC(=O)[C@@H]1C[C@@H](OC)CN21] | Intermediate 20a | $(M + H)^+$ = 451 | 1.32 min (method D) |
| 19-1 | 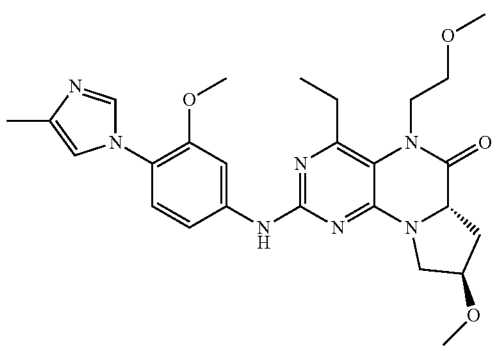 | Intermediate 22a-1 | $(M + H)^+$ = 508 | 1.36 min (method D) |

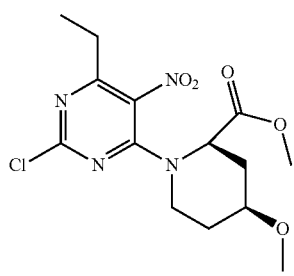

Racemic. Only one isomer is shown.

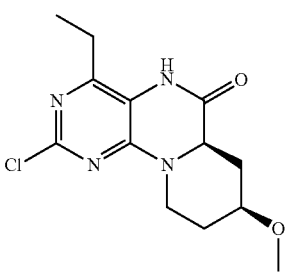

Racemic. Only one isomer is shown.

Intermediate 23a

Intermediate 23a is prepared in analogy to the preparation of intermediate 1a using intermediate 7a and racemic cis-4-methoxypiperidine-2-carboxylic acid methyl ester (prepared in analogy to *J. Org. Chem.* 1990, 55, 738-741).

MS (ESI$^+$): m/z=359/361 (Cl) [M+H]$^+$

HPLC (Method B): Rt=0.91 min.

Intermediate 24a

Intermediate 24a is prepared in analogy to the preparation of intermediate 2a using intermediate 23a.

MS (ESI$^+$): m/z=297/299 (Cl) [M+H]$^+$

HPLC (Method D): Rt=1.09 min.

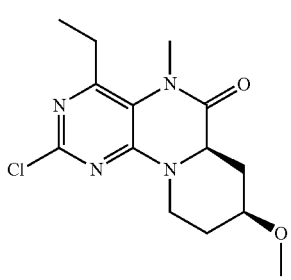

Racemic. Only one isomer is shown.

Intermediate 25a

Intermediate 25a is prepared in analogy to the preparation of intermediate 3a using intermediate 24a and methyl iodide.

MS (ESI$^+$): m/z=311/313 (Cl) [M+H]$^+$
HPLC (Method B): Rt=0.76 min.

In analogy to the preparation of example 9 the following examples are obtained:

residue is dissolved in DCM and is filtered through a plug of basic Alox. The filtrate is concentrated in vacuo and the crude material is taken to next step without any further purification.

MS (ESI$^+$): m/z=224 [m+H]$^+$
HPLC (Method A): Rt=0.36 min.

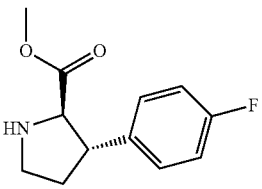

Racemic. Only one isomer is shown.

Intermediate 26b

Intermediate 26b is prepared in analogy to the preparation of intermediate 26a using intermediate trans-3-(4-fluorophenyl)pyrrolidine-2-carboxylic acid.

MS (ESI$^+$): m/z=224 [M+H]$^+$
HPLC (Method A): Rt=0.38 min.

| Exp. | Structure | Educt | Mass signal(s) | R$_t$ |
|---|---|---|---|---|
| 20 | 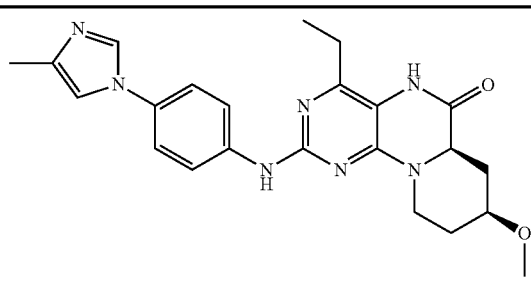 Racemic. Only one isomer is shown. | Intermediate 24a 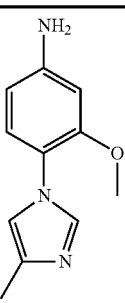 | (M + H)$^+$ = 464 | 1.37 min (method D) |
| 21 | 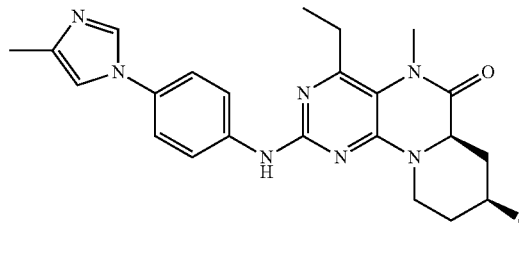 Racemic. Only one isomer is shown.. | Intermediate 25a 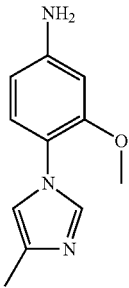 | (M + H)$^+$ = 478 | 1.45 min (method D) |

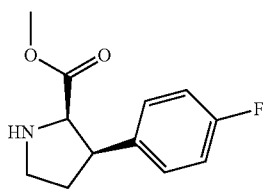

Racemic. Only one isomer is shown.

Intermediate 26a

To a solution of cis-3-(4-fluorophenyl)pyrrolidine-2-carboxylic acid (2.00 g, 9.56 mmol) in methanol (50 mL) at 0° C. is added thionyl chloride (0.83 mL, 11 mmol). The cooling is was removed and the reaction mixture is stirred at room temperature for 2 h and then concentrated in vacuo. The

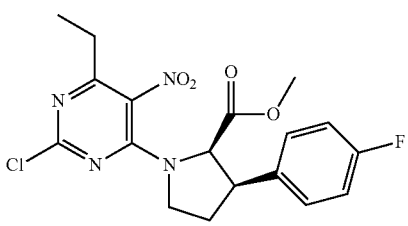

Racemic. Only one isomer is shown.

Intermediate 27a

Intermediate 7a (2.00 g, 9.01 mmol) and Intermediate 26a (1.84 g, 8.24 mmol) is mixed with DMF (7 mL). Potassium carbonate (2.49 g, 18.0 mmol) is added. The reaction mixture is stirred at room temperature for 2 h, whereupon it is concentrated in vacuo. The residue is diluted with water and extracted with DCM. The combined organic extracts are dried, concentrated in vacuo and purified by preparative HPLC (eluent A: water+0.13% TFA, eluent B: MeOH).

MS (ESI$^+$): m/z=409 [m+H]$^+$

HPLC (Method A): Rt=0.84 min.

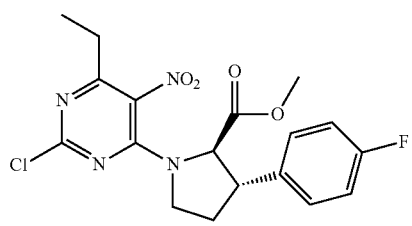

Racemic. Only one isomer is shown.

Intermediate 27b

Intermediate 27b was prepared in analogy to intermediate 27a using intermediate 7a and intermediate 26b.

MS (ESI$^+$): m/z=409 [M+H]$^+$

HPLC (Method A): Rt=0.84 min.

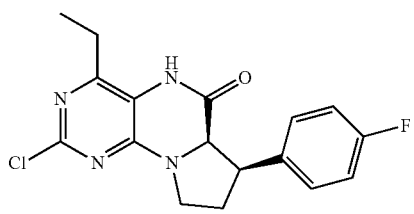

Racemic. Only one isomer is shown.

Intermediate 28a

Intermediate 28a is prepared in analogy to the preparation of intermediate 2a using intermediate 27a.

MS (ESI$^+$): m/z=347 [M+H]$^+$

HPLC (Method A): Rt=0.68 min.

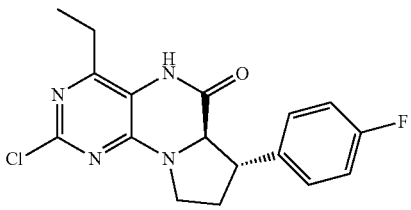

Racemic. Only one isomer is shown.

Intermediate 28b

Intermediate 28a is prepared in analogy to the preparation of intermediate 2a using intermediate 27b.

MS (ESI$^+$): m/z=347 [M+H]$^+$

HPLC (Method A): Rt=0.68 min.

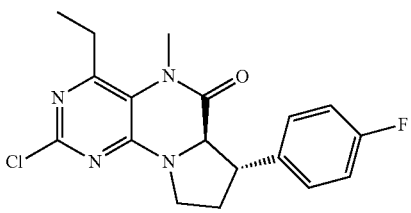

Racemic. Only one isomer is shown.

Intermediate 29a

Intermediate 28b (400 mg, 1.15 mmol) is mixed with DMA (5 mL). At 0° C. methyl iodide (209 µL, 3.35 mmol) and sodium hydride (212 mg, 5.30 mmol, 60% in mineral oil) are added in 3 portions. The reaction mixture is stirred for 3 d, whereupon water is added. The starting material is separated by precipitation and the mother liquor is purified by preparative HPLC (eluent A: water+0.13% TFA, eluent B: MeOH).

MS (ESI$^+$): m/z=361 [M+H]$^+$

HPLC (Method D): Rt=1.40 min.

In analogy to the preparation of example 13 the following examples are obtained:

| Exp. | Structure | Educt | Mass signal(s) | R$_t$ |
|---|---|---|---|---|
| 22 | (racemic, only one isomer is shown) | Intermediate 28a + NH$_2$-aryl | (M + H)$^+$ = 514 | 1.03 min (method E) |

| Exp. | Structure | Educt | Mass signal(s) | $R_t$ |
|---|---|---|---|---|
| 23 | 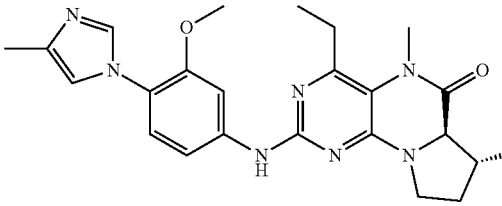 Racemic. Only one isomer is shown. | Intermediate 29a | $(M + H)^+$ = 528 | 0.68 min (method A) |

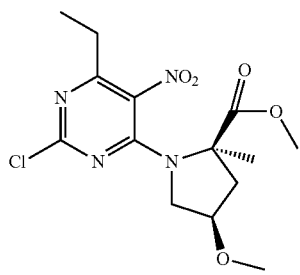 [SMILES: CCc1nc(Cl)nc(N2C[C@H](OC)C[C@]2(C)C(=O)OC)c1[N+](=O)[O-]]

Intermediate 30a

Intermediate 30a is prepared in analogy to the preparation of intermediate 1a using intermediate 7a and (2R,4R)-4-methoxypyrrolidine-2-methyl-2-carboxylic acid methyl ester (prepared in analogy to WO2007131982).

MS (ESI$^+$): m/z=359 [M+H]$^+$

HPLC (Method C): Rt=1.44 min.

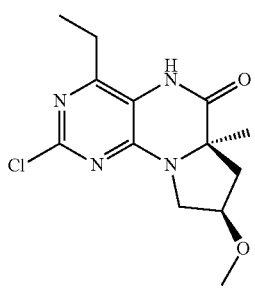 [SMILES: CCc1nc(Cl)nc2c1NC(=O)[C@@]1(C)C[C@@H](OC)CN21]

Intermediate 31a

Intermediate 31a is prepared in analogy to the preparation of intermediate 2a using intermediate 30a.

MS (ESI$^+$): m/z=297 [M+H]$^+$

HPLC (Method C): Rt=1.05 min.

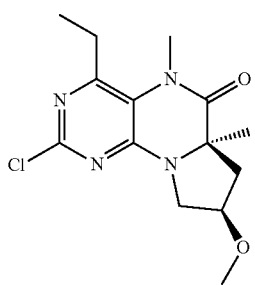 [SMILES: CCc1nc(Cl)nc2c1N(C)C(=O)[C@@]1(C)C[C@@H](OC)CN21]

Intermediate 32a

Intermediate 32a is prepared in analogy to the preparation of intermediate 3a using intermediate 31a and methyl iodide.

MS (ESI$^+$): m/z=311 [M+H]$^+$

HPLC (Method C): Rt=1.13 min.

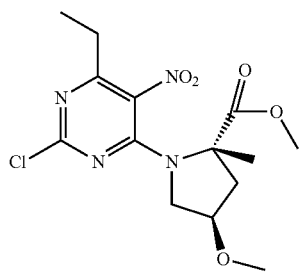 [SMILES: CCc1nc(Cl)nc(N2C[C@H](OC)C[C@@]2(C)C(=O)OC)c1[N+](=O)[O-]]

Intermediate 33a

Intermediate 33a is prepared in analogy to the preparation of intermediate 1a using intermediate 7a and (2S,4R)-4-methoxypyrrolidine-2-methyl-2-carboxylic acid methyl ester (prepared in analogy to WO2007131982).

MS (ESI$^+$): m/z=359 [M+H]$^+$

HPLC (Method A): Rt=0.77 min.

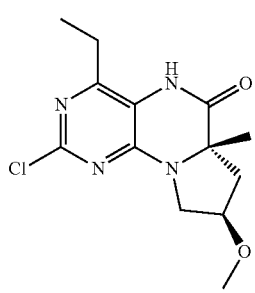 [SMILES: CCc1nc(Cl)nc2c1NC(=O)[C@]1(C)C[C@@H](OC)CN21]

Intermediate 34a

Intermediate 34a is prepared in analogy to the preparation of intermediate 2a using intermediate 33a.

MS (ESI$^+$): m/z=297 [M+H]$^+$

HPLC (Method F): Rt=1.09 min.

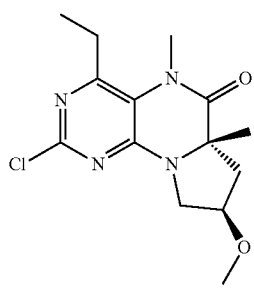 [SMILES: CCc1nc(Cl)nc2c1N(C)C(=O)[C@]1(C)C[C@@H](OC)CN21]

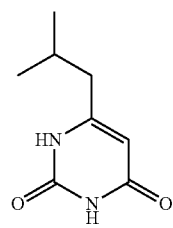

Intermediate 35a

Intermediate 35a is prepared in analogy to the preparation of intermediate 3a using intermediate 34a and methyl iodide.

MS (ESI$^+$): m/z=311 [M+H]$^+$

HPLC (Method F): Rt=1.15 min.

In analogy to the preparation of example 9 the following examples are obtained:

Intermediate 37a

Intermediate 37a is prepared in analogy to the preparation of intermediate 5a. TLC (Silica gel, DCM/methanol 10:1): Rf=0.6

| Exp. | Structure | Educt | | Mass signal(s) | $R_t$ |
|---|---|---|---|---|---|
| 24 | 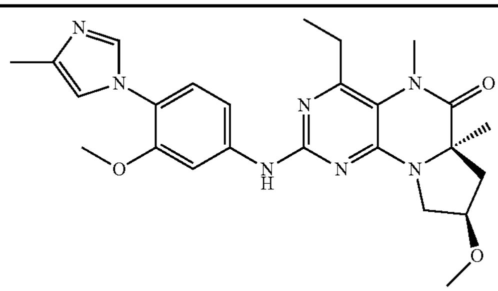 | Intermediate 32a | NH$_2$ | (M + H)$^+$ = 478 | 0.90 min (method C) |
| 25 | 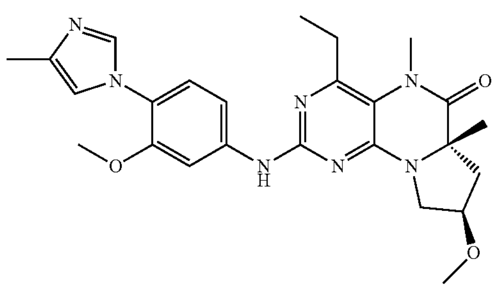 | Intermediate 35a | NH$_2$ | (M + H)$^+$ = 478 | 0.90 min (method C) |

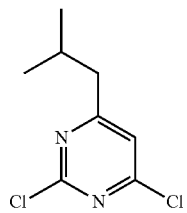

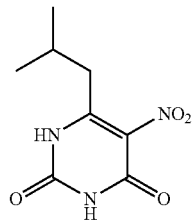

Intermediate 36a

Intermediate 36a is prepared in analogy to the preparation of intermediate 4a using 2,4,6-trichloropyrimidine and isobutyl magnesium bromide.

TLC (Silica gel, PE/ethyl acetate 15:1): Rf=0.6

Intermediate 38a

Intermediate 38a is prepared in analogy to the preparation of intermediate 6a. TLC (Silica gel, DCM/methanol 10:1): Rf=0.6

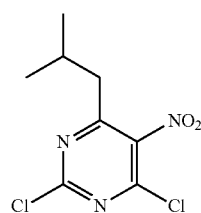

Intermediate 39a

Intermediate 38a (2.0 g, 9.4 mmol) is added at room temperature to phosphorus oxychloride (10 mL) and heated by microwave irradiation (30 min at 145° C.). After cooling to room temperature the reaction mixture is poured into water and extracted with DCM. The organic phase is separated and concentrated in vacuo to yield the product.

MS (ESI⁻): m/z=250 [M+H]⁺
HPLC (Method D): Rt=1.56 min.

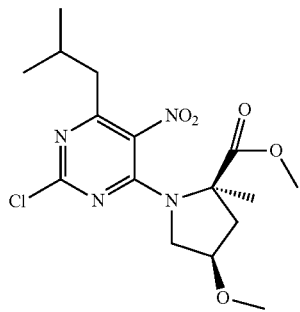 [SMILES: COC(=O)[C@@]1(C)C[C@@H](OC)CN1c1nc(Cl)nc(CC(C)C)c1[N+](=O)[O-]]

Intermediate 40a (2R,4R)-4-Methoxypyrrolidine-2-methyl-2-carboxylic acid methyl ester (HCl salt, 132 mg, 629 μmol, prepared in analogy to WO2007131982), potassium carbonate (217 mg, 1.57 mmol) and intermediate 39a (185 mg, 629 μmol) are stirred in DMF (2.6 mL) at room temperature for 1 h. The reaction mixture is diluted with methanol, filtered and purified by preparative HPLC to yield the product.

MS (ESI⁺): m/z=387 [M+H]⁺
HPLC (Method C): Rt=1.56 min.

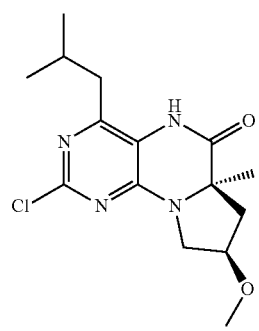 [SMILES: CO[C@H]1CN2c3nc(Cl)nc(CC(C)C)c3NC(=O)[C@@]2(C)C1]

Intermediate 41a

Intermediate 41a is prepared in analogy to the preparation of intermediate 2a using intermediate 40a.

MS (ESI⁺): m/z=325 [M+H]⁺
HPLC (Method C): Rt=0.99 min.

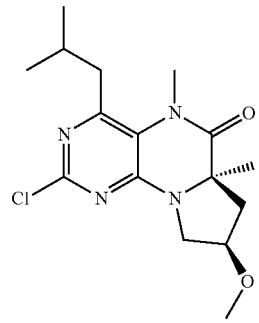 [SMILES: CO[C@H]1CN2c3nc(Cl)nc(CC(C)C)c3N(C)C(=O)[C@@]2(C)C1]

Intermediate 42a

Intermediate 42a is prepared in analogy to the preparation of intermediate 3a using intermediate 41a and methyl iodide.

MS (ESI⁺): m/z=339 [M+H]⁺
HPLC (Method C): Rt=1.30 min.

In analogy to the preparation of example 9 the following examples are obtained:

| Exp. | Structure | Educt | Mass signal(s) | $R_t$ |
|---|---|---|---|---|
| 26 | ![structure] | Intermediate 42a ![NH2 structure] | (M + H)⁺ = 506 | 0.95 min (Method C) |

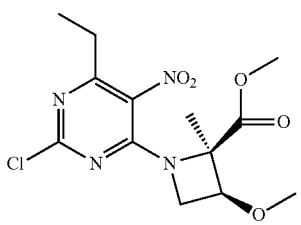

Racemic. Only one is isomer is shown.

Intermediate 43a

Intermediate 43a is prepared in analogy to the preparation of intermediate 1a using intermediate 7a and cis-(2RS,3RS)-3-methoxy-2-methyl-azetine-2-carboxylic acid methyl ester (prepared in analogy to WO2008135525).
MS (ESI$^+$): m/z=345 [M+H]$^+$
HPLC (Method C): Rt=1.43 min.

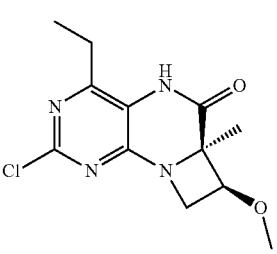

Racemic. Only one is isomer is shown.

Intermediate 44a

Intermediate 44a is prepared in analogy to the preparation of intermediate 2a using intermediate 43a.
MS (ESI$^+$): m/z=283 [M+H]$^+$
HPLC (Method C): Rt=1.00 min.
In analogy to the preparation of example 9 the following examples are obtained:

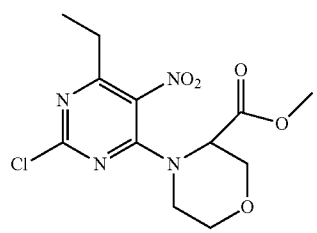 [SMILES: CCc1nc(Cl)nc(N2CCOCC2C(=O)OC)c1[N+](=O)[O-]]

Intermediate 45a

Intermediate 45a is prepared in analogy to the preparation of intermediate 1a using intermediate 7a and morpholine-3-carboxylic acid methyl ester.
MS (ESI$^+$): m/z=331 [M+H]$^+$
HPLC (Method D): Rt=1.37 min.

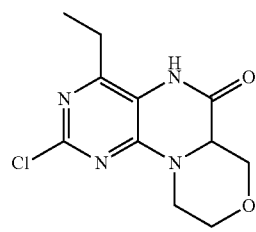 [SMILES: CCc1nc(Cl)nc2c1NC(=O)C1COCCN21]

Intermediate 46a

Intermediate 45a (730.0 mg, 2.2 mmol) is hydrogenated over Raney nickel (300 mg) in ethyl acetate (98 mL) for 1d (1 bar H$_2$ atmosphere, room temperature). The reaction mixture is filtered and concentrated in vacuo to yield the product.
MS (ESI$^+$): m/z=269 [M+H]$^+$
HPLC (Method B): Rt=0.62 min.

| Exp. | Structure | Educt | Mass signal(s) | R$_t$ |
|---|---|---|---|---|
| 27 | ![structure] Racemic. Only one isomer is shown. | Intermediate 44a, ![NH2 structure] | (M + H)$^+$ = 450 | 0.83 min (Method C) |

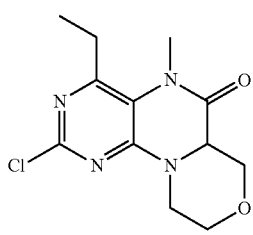 [SMILES: CCc1nc(Cl)nc2c1N(C)C(=O)C1COCCN21]

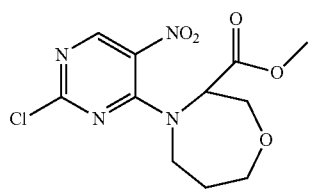

Intermediate 47a

Intermediate 47a is prepared in analogy to the preparation of intermediate 3a using intermediate 46a and methyl iodide.

MS (ESI⁺): m/z=283 [M+H]⁺

HPLC (Method D): Rt=1.11 min.

In analogy to the preparation of example 9 the following examples are obtained:

Intermediate 49a

Intermediate 49a is prepared in analogy to the preparation of intermediate 1a using intermediate 48a.

MS (ESI⁺): m/z=317 [M+H]⁺

HPLC (Method C): Rt=1.11 min.

| Exp. | Structure | Educt | Mass signal(s) | $R_t$ |
|---|---|---|---|---|
| 28 | | Intermediate 46a | $NH_2$ | $(M + H)^+ = 436$ | 0.80 min (method C) |
| 29 | | Intermediate 47a | $NH_2$ | $(M + H)^+ = 450$ | 0.80 min (method C) |

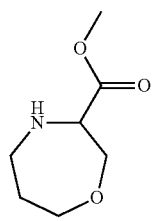

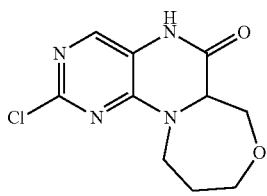 [SMILES: O=C1Nc2cnc(Cl)nc2N2CCCOCC12]

Intermediate 48a

[1,4]Oxazepane-3,4-dicarboxylic acid-4-tert.-butyl ester-3-methyl ester (1.0 g, 3.9 mmol) is stirred in a solution of HCl in 1,4-dioxane (10 mL, 4N) for 1 h. The reaction mixture is concentrated in vacuo to give the product as HCl salt.

MS (ESI⁺): m/z=260 [M+H]⁺

Intermediate 50a

Intermediate 50a is prepared in analogy to the preparation of intermediate 2a using intermediate 49a.

MS (ESI⁺): m/z=255 [M+H]⁺

HPLC (method C): Rt=0.89 min.

In analogy to the preparation of example 9 the following examples are obtained:

| Exp. | Structure | Educt | Mass signal(s) | $R_t$ |
|---|---|---|---|---|
| 30 | 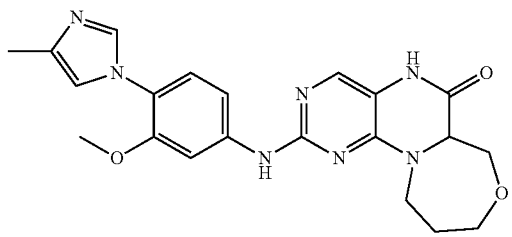 [SMILES: COc1cc(Nc2ncc3c(n2)N2CCCOCC2C(=O)N3)ccc1-n1cnc(C)c1] | Intermediate 50a | $(M + H)^+ = 422$ | 0.51 min (method B) |

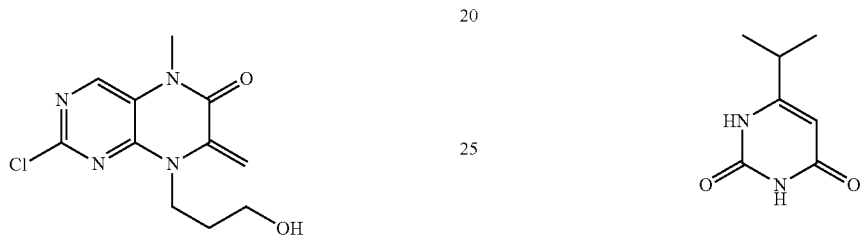

Intermediate 51a

Intermediate 51a is prepared in analogy to the preparation of intermediate 13a using intermediate 50a.

MS (ESI$^+$): m/z=269 [M+H]$^+$

HPLC (Method C): Rt=0.93 min.

In analogy to the preparation of example 9 the following examples are obtained:

| Exp. | Structure | Educt | Mass signal(s) | $R_t$ |
|---|---|---|---|---|
| 31 | 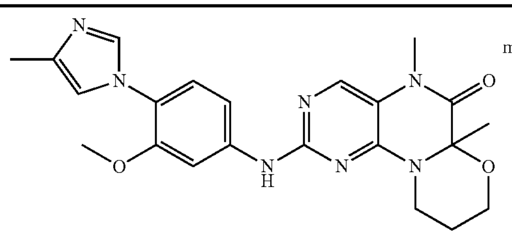 | Intermediate 51a | $(M + H)^+ = 436$ | 0.75 min (Method C) |

Intermediate 52a

Intermediate 52a is prepared in analogy to the preparation of intermediate 4a using 2,4,6-trichloropyrimidine and isopropyl magnesium bromide.

TLC (Silica gel, PE/ethyl acetate 15:1): Rf=0.6

Intermediate 53a

Intermediate 53a is prepared in analogy to the preparation of intermediate 5a.

TLC (Silica gel, PE/ethyl acetate 1:1): Rf=0.1

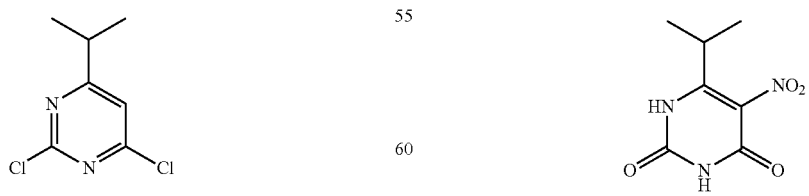

Intermediate 54a

Intermediate 54a is prepared in analogy to the preparation of intermediate 6a.

TLC (Silica gel, DCM/methanol 10:1): Rf=0.5

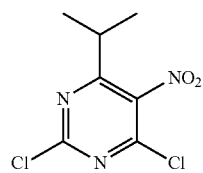

Intermediate 55a

Intermediate 55a is prepared in analogy to the preparation of intermediate 39a using intermediate 54a (microwave irradiation for 30 min at 160° C.).

HPLC (Method C): Rt=1.54 min.

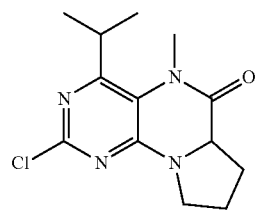

Intermediate 58a

Intermediate 58a is prepared in analogy to the preparation of intermediate 3a using intermediate 57a and methyl iodide.

MS (ESI$^+$): m/z=281 [M+H]$^+$

HPLC (Method C): Rt=1.23 min.

In analogy to the preparation of example 9 the following examples are obtained:

| Exp. | Structure | Educt | Mass signal(s) | R$_t$ |
|---|---|---|---|---|
| 32 | 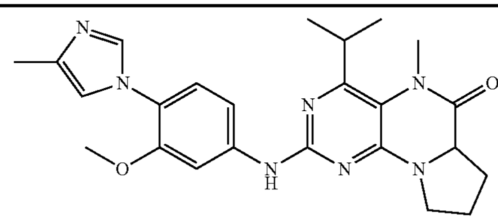 | Intermediate 58a | NH$_2$ (M + H)$^+$ = 448 | 0.93 min (Method C) |

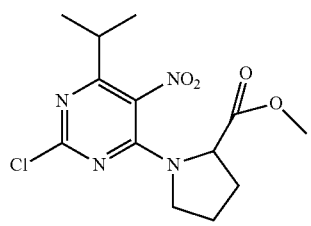 [SMILES: COC(=O)C1CCCN1c1nc(Cl)nc(C(C)C)c1[N+](=O)[O-]]

Intermediate 56a

Intermediate 56a is prepared in analogy to the preparation of intermediate 11a using intermediate 55a.

MS (ESI$^+$): m/z=329 [M+H]$^+$

HPLC (Method C): Rt=1.51 min.

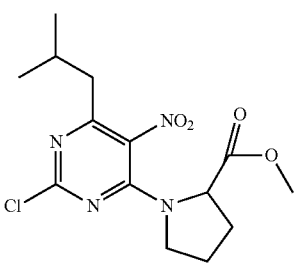 [SMILES: COC(=O)C1CCCN1c1nc(Cl)nc(CC(C)C)c1[N+](=O)[O-]]

Intermediate 59a

Intermediate 59a is prepared in analogy to the preparation of intermediate 11a using intermediate 39a.

MS (ESI$^+$): m/z=343 [M+H]$^+$

HPLC (Method D): Rt=1.49 min.

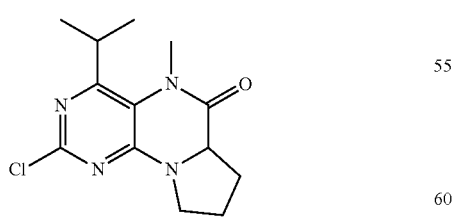

Intermediate 57a

Intermediate 57a is prepared in analogy to the preparation of intermediate 2a using intermediate 56a.

MS (ESI$^+$): m/z=267 [M+H]$^+$

HPLC (Method C): Rt=1.13 min.

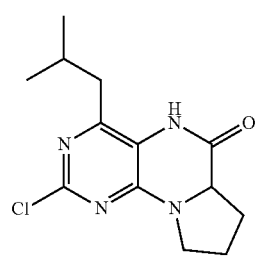 [SMILES: CC(C)Cc1nc(Cl)nc2c1NC(=O)C1CCCN21]

Intermediate 60a

Intermediate 60a is prepared in analogy to the preparation of intermediate 2a using intermediate 59a.
    MS (ESI⁺): m/z=281 [M+H]⁺
    HPLC (Method D): Rt=1.22 min.

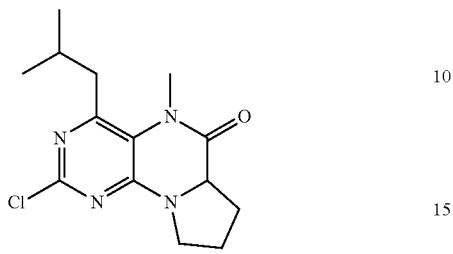

Intermediate 61a

Intermediate 61a is prepared in analogy to the preparation of intermediate 3a using intermediate 60a and methyl iodide.
    MS (ESI⁺): m/z=295 [M+H]⁺
    HPLC (Method C): Rt=1.30 min.

In analogy to the preparation of example 9 the following examples are obtained:

Intermediate 62a

Intermediate 62a is prepared in analogy to the preparation of intermediate 1a using intermediate 7a and methyl pipecolinate.
    MS (ESI⁺): m/z=329 [M+H]⁺
    HPLC (Method G): Rt=1.36 min.

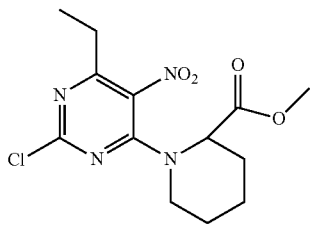 [SMILES: CCc1nc(Cl)nc(N2CCCCC2C(=O)OC)c1[N+](=O)[O-]]

| Exp. | Structure | Educt | | Mass signal(s) | $R_t$ |
|---|---|---|---|---|---|
| 33 | 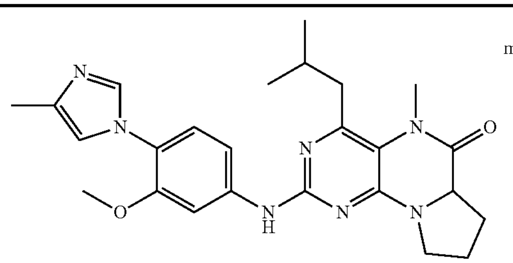 | Intermediate 61a | NH₂ | (M + H)⁺ = 462 | 0.95 min (Method C) |
| 34 | 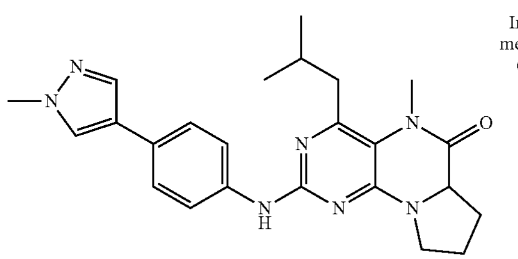 | Intermediate 61a | NH₂ | (M + H)⁺ = 432 | 1.12 min (Method C) |
| 35 | 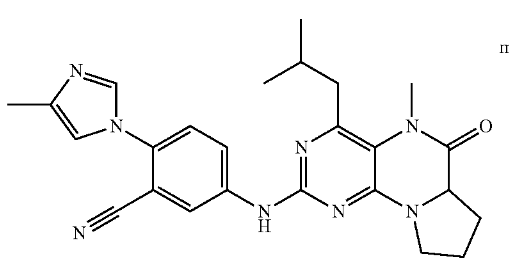 | Intermediate 61a | NH₂ | (M + H)⁺ = 457 | 0.91 min (Method C) |

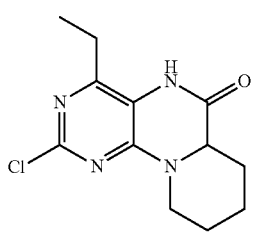

Intermediate 63a

Intermediate 63a is prepared in analogy to the preparation of intermediate 2a using intermediate 62a.
MS (ESI$^+$): m/z=267 [M+H]$^+$
HPLC (Method F): Rt=1.14 min.

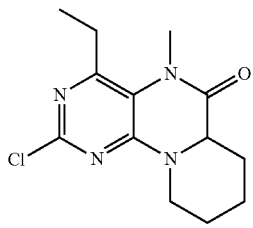

Intermediate 64a

Intermediate 64a is prepared in analogy to the preparation of intermediate 3a using intermediate 63a.
MS (ESI$^+$): m/z=281 [M+H]$^+$
HPLC (Method F): Rt=1.22 min.

In analogy to the preparation of example 9 the following examples are obtained:

The crude product is purified by silica gel chromatography (gradient ethyl acetate/CH 95:5 ethyl acetate/ethanol 9:1) to give the product.
MS (ESI$^+$): m/z=234 [M+H]$^+$
HPLC (Method H): Rt=0.97 min.

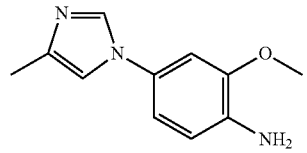

Intermediate 66a

Intermediate 65a (0.55 g, 2.36 mmol) is hydrogenated (4 bar H$_2$ atmosphere) over palladium/charcoal (50 mg) in methanol (20 mL) at 60° C. After cooling to room temperature the reaction mixture is concentrated in vacuo. The residue is triturated with diethyl ether and hydrochloric acid in 1,4-dioxane (4N) to give the product as HCl salt.
MS (ESI$^+$): m/z=204 [M+H]$^+$

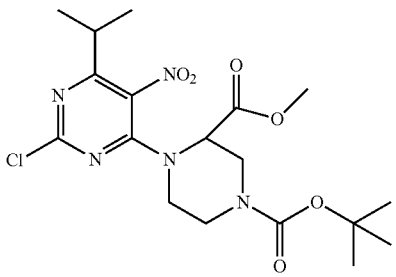 [SMILES: COC(=O)C1CN(C(=O)OC(C)(C)C)CCN1c1nc(Cl)nc(C(C)C)c1[N+](=O)[O-]]

Intermediate 67a

Intermediate 67a is prepared in analogy to the preparation of intermediate 1a using intermediate 55a and piperazine-1,3-dicarboxylic acid-1-tert.-butyl ester-3-methyl ester.
MS (ESI$^+$): m/z=444 [M+H]$^+$
HPLC (Method D): Rt=1.53 min.

| Exp. | Structure | Educt | Mass signal(s) | R$_t$ |
|---|---|---|---|---|
| 36 | 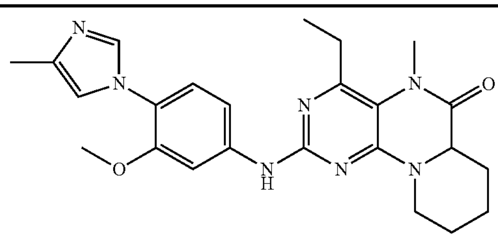 | Intermediate 64a / NH$_2$ | (M + H)$^+$ = 448 | 0.87 min (method C) |

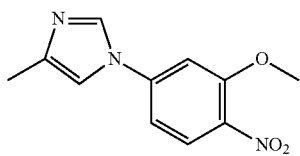

Intermediate 65a

4-Methyl imidazole (1.1 g, 13.4 mmol), 4-fluoro-2-methoxy-1-nitro-benzene (2.1 g, 12.2 mmol) and potassium carbonate (1.7 g, 12.2 mmol) are stirred in DMF (30 mL) for 16 h at 85° C. After cooling to room temperature water is added and the precipitated crude product is collected by filtration.

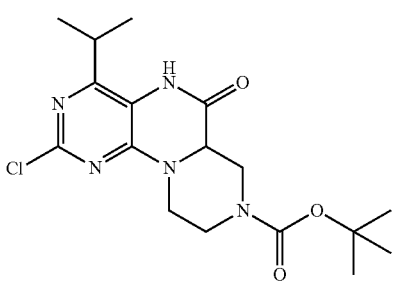 [SMILES: CC(C)c1nc(Cl)nc2c1NC(=O)C1CN(C(=O)OC(C)(C)C)CCN21]

Intermediate 68a

Intermediate 68a is prepared in analogy to the preparation of intermediate 46a using intermediate 67a.
MS (ESI+): m/z=382 [M+H]+
HPLC (Method A): Rt=0.77 min.

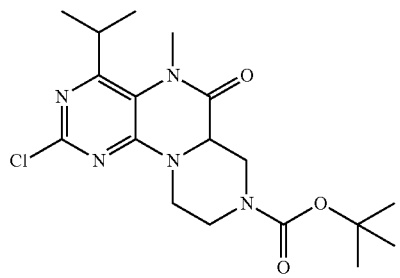 [SMILES: CC(C)c1nc(Cl)nc2c1N(C)C(=O)C1CN(C(=O)OC(C)(C)C)CCN21]

Intermediate 69a

Intermediate 69a is prepared in analogy to the preparation of intermediate 3a using intermediate 68a.
MS (ESI+): m/z=396 [M+H]+
HPLC (Method I): Rt=1.00 min.
In analogy to the preparation of example 9 the following examples are obtained:

| Exp. | Structure | Educt | Mass signal(s) | R$_t$ |
|---|---|---|---|---|
| 37 | 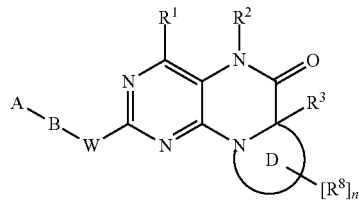 | Intermediate 69a 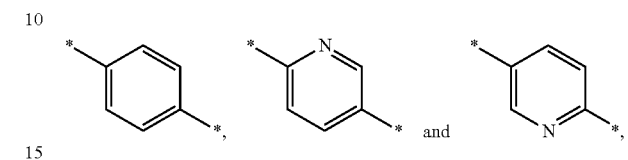 | (M + H)+ = 563 | 0.91 min (method J) |

The invention claimed is:

1. A compound of the formula I

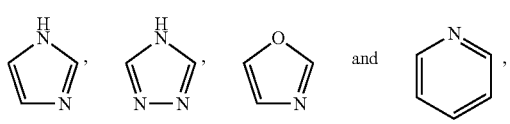

wherein

A is selected from the group A$^e$ consisting of

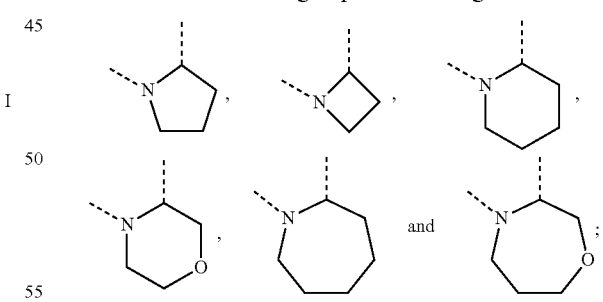

wherein the above mentioned groups may optionally be substituted with 1 or 2 substituents independently selected from the group consisting of halogen and $C_{1-3}$-alkyl- which is optionally fluorinated with 1 to 7 fluorine atoms;

B is selected from the group B$^c$ consisting of wherein above mentioned phenyl- and pyridinyl- groups may optionally be substituted with 1 or 2 substituents independently selected from the group consisting of halogen, cyano, $C_{1-3}$-alkyl- which is optionally fluorinated with 1 to 7 fluorine atoms, and $C_{1-3}$-alkyl-O— which is optionally fluorinated with 1 to 7 fluorine atoms;

D is selected from the group D$^f$ consisting of

W is selected from the group W$^b$ consisting of
—(R$^7$)N—;
R$^1$ is selected from the group R$^{1f}$ consisting of
H, $C_{1-4}$-alkyl-, $C_{3-6}$-cycloalkyl- and benzyl-,
wherein above mentioned $C_{1-4}$-alkyl- and $C_{3-6}$-cycloalkyl-groups may optionally be substituted with 1 to 11 fluorine atoms, and
wherein above mentioned benzyl- group may optionally be substituted with 1 to 3 substituents independently selected from the group consisting of $C_{1-3}$-alkyl-O—, cyano, halogen, and $C_{1-3}$-alkyl-, and wherein above mentioned C$_{1-3}$-alkyl-O— and C$_{1-3}$-alkyl-groups may optionally be substituted with 1 to 7 fluorine atoms;

R$^2$ is selected from the group R$^{2e}$ consisting of
H, C$_{1-3}$-alkyl-O—C$_{1-3}$-alkyl- and C$_{1-3}$-alkyl-;

R$^3$ is selected from the group R$^{3c}$ consisting of
H and H$_3$C—;

R$^7$ is selected the group R$^{7b}$ consisting of
H;

R$^8$ is selected from the group R$^{8f}$ consisting of
H, phenyl and C$_{1-3}$-alkyl-O—,
wherein above mentioned phenyl group may optionally be substituted with 1 to 3 substituents independently selected from the group consisting of cyano, F$_3$C— and fluoro;

n is 0 or 1;

or a tautomer or salt thereof.

2. A compound according to claim 1, selected from the group consisting of:

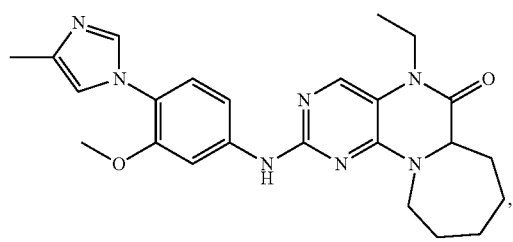

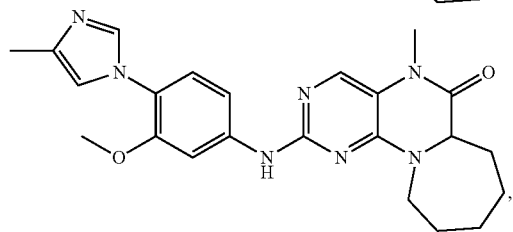

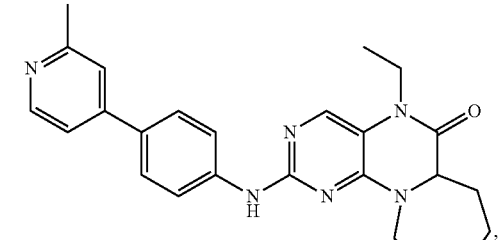

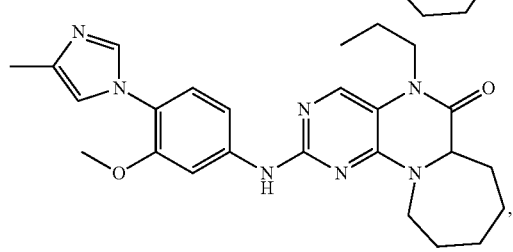

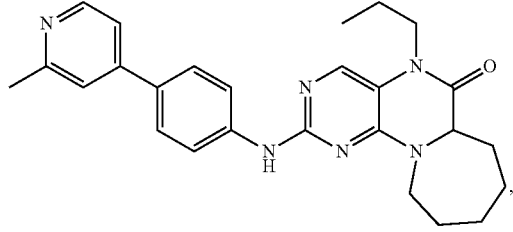

-continued

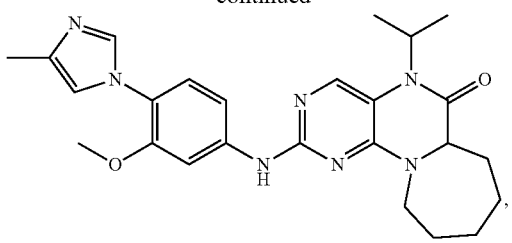

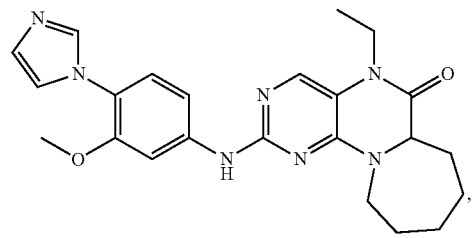

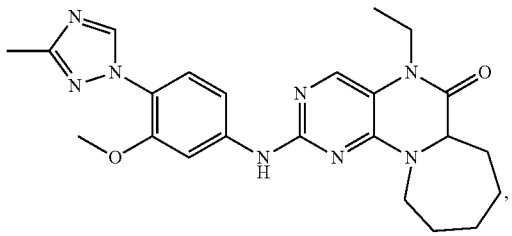

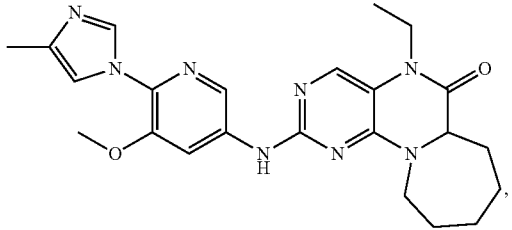

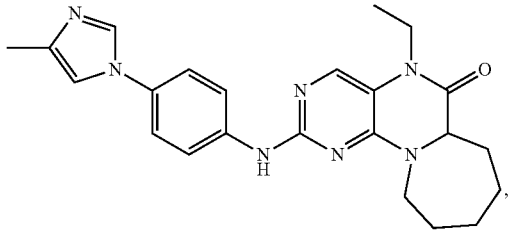

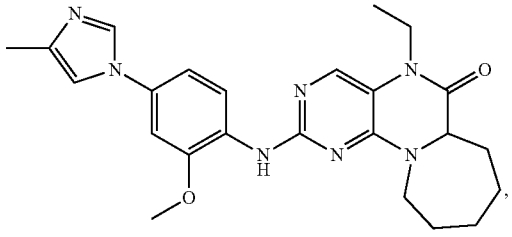

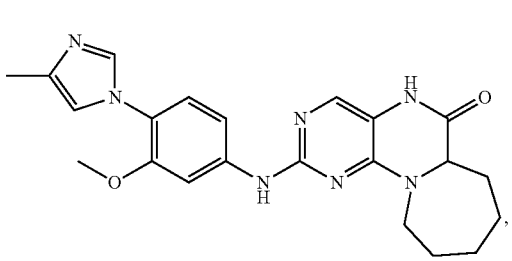

111
-continued
112
-continued
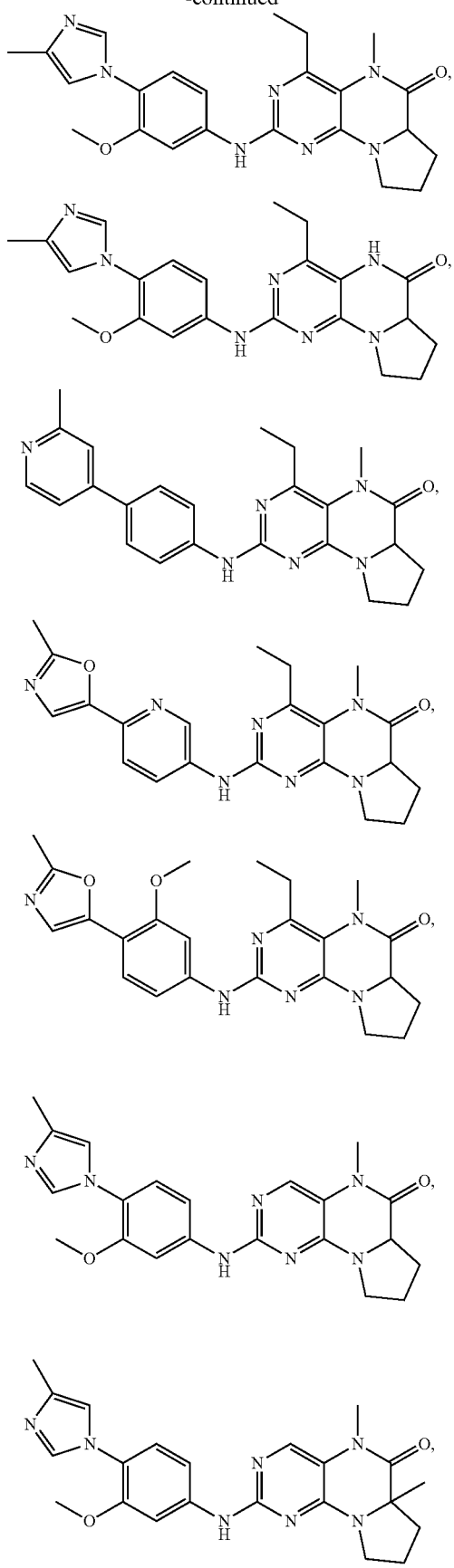
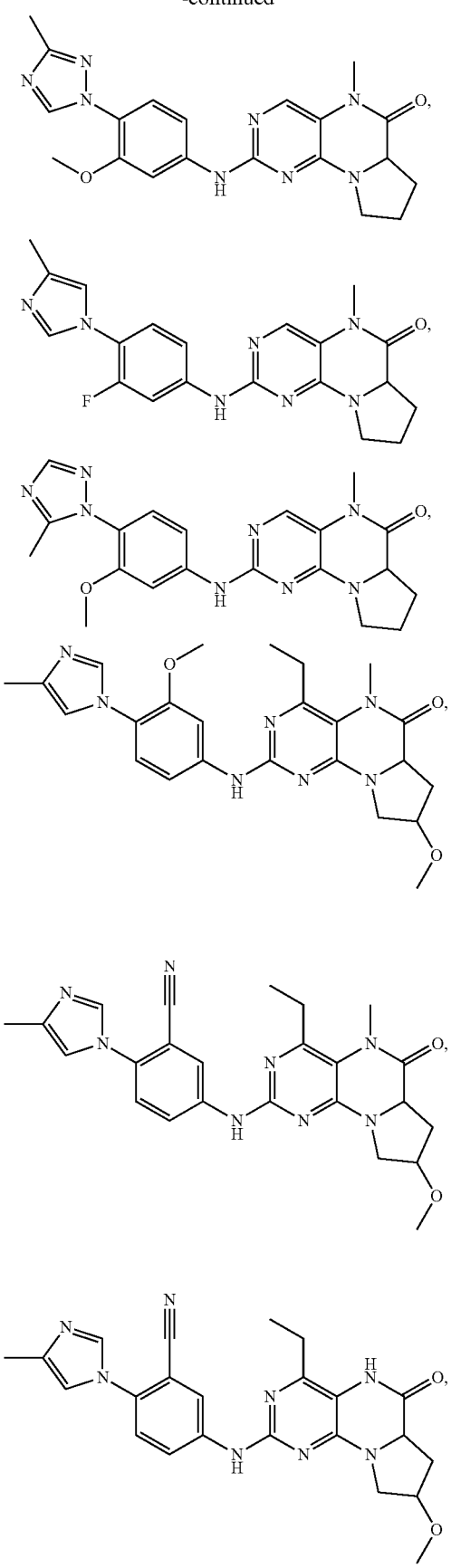

113
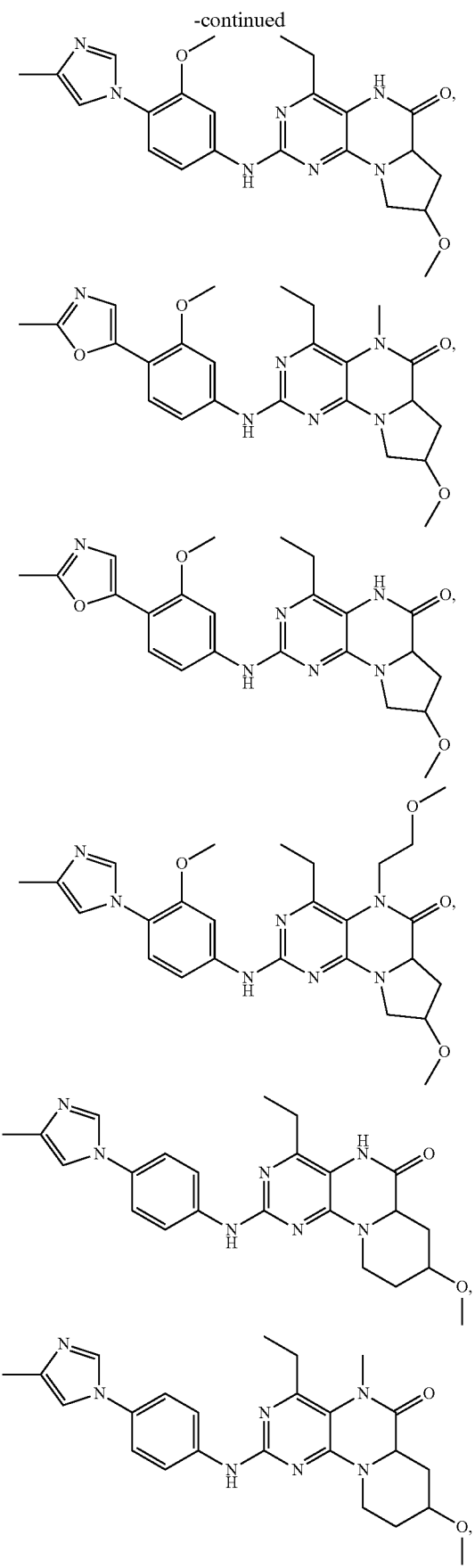
114
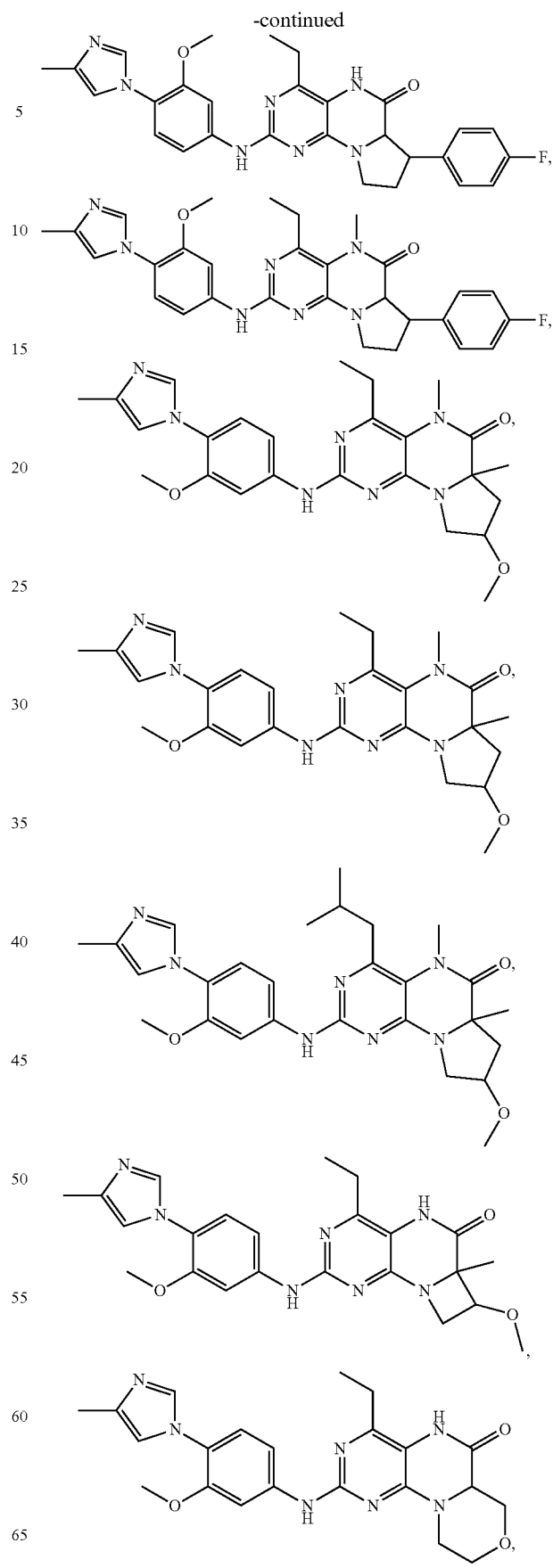

115
-continued
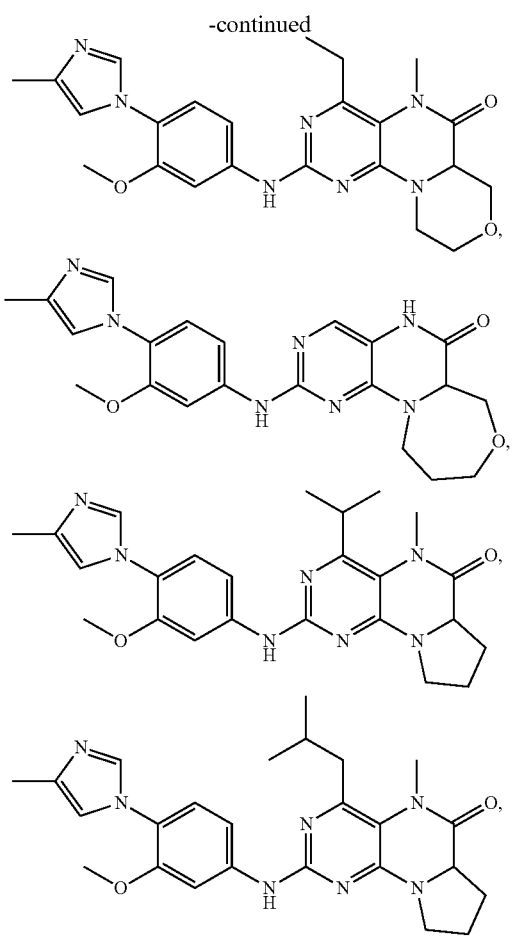
116
-continued
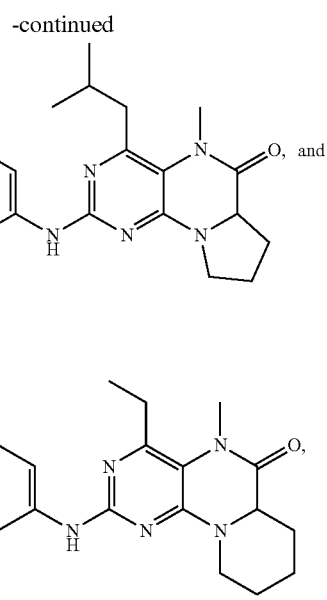
or a salt thereof.
3. A pharmaceutically acceptable salt of a compound according to claim 1 or 2.
4. A pharmaceutical composition comprising a compound according to claim 1 and a pharmaceutically acceptable carrier.
* * * * *